United States Patent [19]

Johnson

[11]  4,380,542
[45]  Apr. 19, 1983

[54] 9-HYDROXYOCTAHYDROBENZO[c-]QUINOLINES AND THEIR PHARMACEUTICAL COMPOSITIONS AND METHOD OF USE

[75] Inventor: Michael R. Johnson, Gales Ferry, Conn.

[73] Assignee: Pfizer, New York, N.Y.

[21] Appl. No.: 328,846

[22] Filed: Dec. 9, 1981

Related U.S. Application Data

[60] Division of Ser. No. 193,822, Oct. 3, 1980, Pat. No. 4,340,737, which is a division of Ser. No. 42,773, May 29, 1979, Pat. No. 4,260,764, which is a continuation-in-part of Ser. No. 777,928, Mar. 15, 1977, abandoned, which is a continuation-in-part of Ser. No. 753,619, Dec. 22, 1976, abandoned, which is a continuation-in-part of Ser. No. 687,332, May 17, 1976, abandoned.

[51] Int. Cl.$^3$ .................... C07D 221/12; A61K 31/47
[52] U.S. Cl. .................... 424/248.55; 424/248.56; 424/250; 424/256; 546/17; 546/108; 544/126; 544/230; 544/361; 544/70
[58] Field of Search ................. 546/17, 108; 544/126, 544/361; 424/248.55, 248.56, 250, 256

[56]  References Cited
U.S. PATENT DOCUMENTS
4,340,737  7/1982  Johnson ............................. 546/108

*Primary Examiner*—Robert T. Bond
*Attorney, Agent, or Firm*—Connolly and Hutz

[57]  ABSTRACT

1,9-Dihydroxyoctahydrobenzo[c]quinolines (I), 1-hydroxyhexahydrobenzo[c]quinoline-9(8H)-ones (II), and 1-hydroxy-tetrahydrobenzo[c]quinolines (IV) useful as CNS agents, especially as analgesics and tranquilizers, as hypotensives, as agents for the treatment of glaucoma and as diuretics; intermediates therefor (III) and derivatives thereof.

8 Claims, No Drawings

9-HYDROXYOCTAHYDROBENZO[C]QUINOLINES AND THEIR PHARMACEUTICAL COMPOSITIONS AND METHOD OF USE

CROSS-REFERENCE TO RELATED APPLICATIONS

This application is a division of application Ser. No. 193,822 filed Oct. 3, 1980, now U.S. Pat. No. 4,340,737, which in turn is a division of application Ser. No. 42,773 filed May 29, 1979, now U.S. Pat. No. 4,260,764, which is a continuation-in-part of copending application Ser. No. 777,928, filed Mar. 15, 1977 and now abandoned which, in turn, is a continuation-in-part of application Ser. No. 753,619, filed Dec. 22, 1976, and now abandoned, which, in turn, is a continuation-in-part of application Ser. No. 687,332, filed May 17, 1976 and now abandoned.

BACKGROUND OF THE INVENTION

This invention relates to certain novel benzo[c]quinolines and more particularly to 1,9-dihydroxyoctahydrobenzo[c]quinolines, 1-hydroxyhexahydrobenzo[c]quinoline-9(8H)-ones and 1-hydroxy-tetrahydrobenzo[c]quinolines and derivatives thereof useful as CNS agents, especially as analgesics and tranquilizers, as hypotensives in mammals, including man, as agents for the treatment of glaucoma and as diuretics; and to intermediates therefor.

An acceptable alternative nomenclature for the herein described compounds of formulae I–IV is based upon replacement of the root "benzo[c]quinoline" with "phenanthridine." Thus, d,l-trans-5,6,6a$\beta$,7,8,9,10,10a$\alpha$-octahydro-1-acetoxy-9$\beta$-hydroxy-6$\beta$-methyl-3(5-phenyl-2-pentyloxy)benzo[c]quinoline becomes d,l-trans-5,6,6a$\beta$,7,8,9,10,10a$\alpha$-octahydro-1-aceytoxy-9$\beta$-hydroxy-6$\beta$-methyl-3-(5-phenyl-2-pentyloxy)phenanthridine.

DESCRIPTION OF THE PRIOR ART

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agents such as d-propoxyphene, codeine, and morphine, possess addictive liability. The need for improved and potent analgesic agents is, therefore, evident.

The analgesic properties of 9-nor-9$\beta$-hydroxyhexahydrocannabinol and of other cannabinoid structures, such as $\Delta^8$-tetrahydrocannabinol ($\Delta^8$-THC) and its primary metabolite, 11-hydroxy-$\Delta^8$-THC, have been reported by Wilson and May, Absts. Papers, Am. Chem. Soc., 168 Meet., MEDI 11 (1974), J. Med. Chem. 17, 475–476 (1974), and J. Med. Chem., 18, 700–703 (1975).

U.S. Pat. Nos. 3,507,885 and 3,636,058, issued Apr. 21, 1970 and Jan. 18, 1972, respectively, describe various 1-hydroxy -3-alkyl-6H-dibenzo-[b,d]pyrans having at the 9-position substituents such as: oxo, hydrocarbyl and hydroxy or chloro, hydrocarbylidene, and intermediates therefor.

U.S. Pat. No. 3,649,650, issued Mar. 14, 1972, discloses a series of tetrahydro-6,6,9-trialkyl-6H-dibenzo[b,d]pyran derivatives having at the 1-position an $\Omega$-dialkylaminoalkoxy group active as psychotherapeutic agents.

German Specification No. 2,451,934, published May 7, 1975, describes 1,9-dihydroxyhexahydrodibenzo[b,d]pyrans and certain 1-acyl derivatives thereof having at the 3-position an alkyl or alkylene group, as hypotensive, psychotropic, sedative and analgesic agents. The precursor hexahydro-9H-dibenzo[b,d]pyran-9-ones used in their preparation, and which are reported to have the same utility as the corresponding 9-hydroxy compounds, are described in German Specification No. 2,451,932, published May 7, 1975.

U.S. Pat. No. 3,856,821, issued Dec. 24, 1974, describes a series of 3-alkoxy substituted dibenzo[b,d]pyrans having antiarthritic, antiinflammatory and central nervous system activity.

Bergel et al., J. Chem. Soc., 286–287 (1943) investigated the replacement of the pentyl group at the 3-position of 7,8,9,10-tetrahydro-3-pentyl-6,6,9-trimethyl-6H-dibenzo[b,d]pyran-1-ol by alkoxy (butoxy, pentyloxy, hexyloxy and octyloxy) and found that it led to biological inactivity. The hexyloxy derivative was reported to exhibit feeble hashish activity at 10 to 20 mg./kg. The remaining ethers showed no activity in doses up to 20 mg./kg.

In a more recent study, Loev et al., J. Med. Chem., 16, 1200–1206 (1973) report a comparison of 7,8,9,10-tetrahydro-3-substituted-6,6,9-trimethyl-6H-dibenzo[b,d]pyran-1-ols in which the 3-substituent is —OCH(CH$_3$)C$_5$H$_{11}$; —CH$_2$CH(CH$_3$)C$_5$H$_{11}$; or —CH(CH$_3$)C$_5$H$_{11}$. The ether side chain containing compound was 50% less active in central nervous system activity than the corresponding compound in which the alkyl side chain is directly attached to the aromatic ring, rather than through an intervening oxygen atom; and 5 times as active as the compound in which oxygen is replaced by methylene.

Hoops et al., J. Org. Chem., 33, 2995–2996 (1968) describe the preparation of the 5-aza analog of $\Delta^{6a(10a)}$-tetrahydrocannabinol referred to therein as 7,8,9,10-tetrahydro-1-hydroxy-5,6,6,9-tetramethyl-3-n-pentyl-phenanthridine, but report no utility for the compound. Beil, in "Psychomimetic Drugs," edited by Efron, Raven Press, New York, 1970, page 336, reports the compound was "completely inert in animal pharmacology."

Hardman et al., Proc. West. Pharmacol. Soc., 14, 14–20 (1971) reports some pharmacological activity for 7,8,9,10-tetrahydro-1-hydroxy-6,6,9-trimethyl-3-n-pentyl phenanthridine, a 5-aza $\Delta^{6a(10)a}$-tetrahydrocannabinol.

Machoulam and Edery in "Marijuana," edited by Mechoulam, Academic Press, New York, 1973, page 127, observe that major structural changes in the tetrahydrocannabinol molecule seem to result in steep reductions in analgesic activity.

Paton, in Annual Review of Pharmacology, 15, 192 (1975) presents generalizations on structure-action relationships among cannabinoids. The presence of the gem dimethyl group in the pyran ring is critical for cannabinoid activity and substitution of N for O in the pyran ring removes activity.

SUMMARY OF THE INVENTION

It has now been found that certain benzo[c]quinolines; namely, 1,9-dihydroxyoctahydro-6H-benzo[c]quinolines (I), 1-hydroxyhexahydro-6H-benzo[c]quinoline-9(8H)-ones (II) and 1-hydroxy-tetrahydroquinolines (IV) are effective as CNS agents, especially as analgesics and tranquilizers, as hypotensives, which are non-narcotic and free of addiction liability, as agents for the treatment of glaucoma and as diuretics. Also included in this invention are various derivatives of said compounds which are useful as dosage forms and intermediates therefor. The above-named compounds and their derivatives have the formulae I, II and IV. Compounds of formulae III and IV are precursors to compounds of formulae II and I.

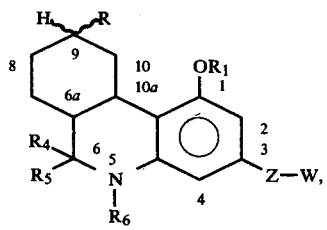

(I)

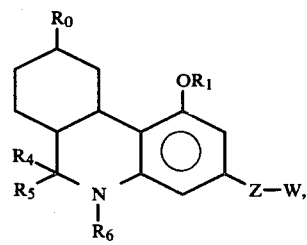

(II)

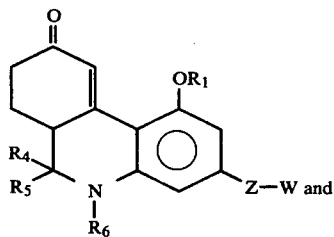

(III)

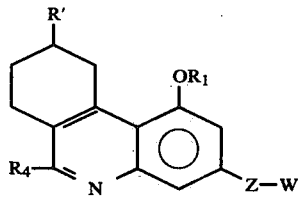

(IV)

wherein R is selected from the group consisting of hydroxy, alkanoyloxy having from one to five carbon atoms and hydroxymethyl;

$R_1$ is selected from the group consisting of hydrogen, benzyl, benzoyl alkanoyl having from one to five carbon atoms and $-CO-(CH_2)_p-HR_2R_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is selected from the group consisting of hydrogen, alkyl having from 1 to 6 carbon atoms and $-(CH_2)_z-C_6H_5$ wherein z is an integer from 1 to 4;

$R_5$ is selected from the group consisting of hydrogen, methyl and ethyl;

$R_6$ is selected from the group consisting of hydrogen, $-(CH_2)_y$-carbalkoxy having from one to four carbon atoms in the alkoxy group and y is 0 or an integer from 1 to 4; carbobenzyloxy, formyl, alkanoyl having from two to five carbon atoms, alkyl having from one to six carbon atoms; $-(CH_2)_x-C_6H_5$ wherein x is an integer from 1 to 4; and $-CO(CH_2)_{x-1}-C_6H_5$;

$R_0$ is selected from the group consisting of oxo, methylene and alkylenedioxy having from two to four carbon atoms;

R' is selected from the group consisting of R and $R_0$;

Z is selected from the group consisting of
(a) alkylene having from one to nine carbon atoms;
(b) -$(alk_1)_m$-X-$(alk_2)_n$- wherein each of $(alk_1)$ and $(alk_2)$ is alkylene having from one to nine carbon atoms, with the proviso that the summation of carbon atoms in $(alk_1)$ plus $(alk_2)$ is not greater than nine; each of m and n is 0 or 1; X is selected from the group consisting of O, S, SO and $SO_2$; and W is selected from the group consisting of hydrogen, methyl, pyridyl, piperidyl,

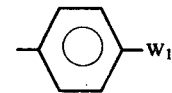

wherein $W_1$ is selected from the group consisting of hydrogen, fluoro and chloro; and

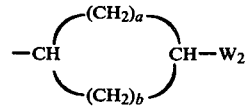

wherein $W_2$ is selected from the group consisting of hydrogen and

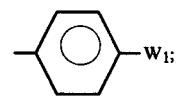

a is an integer from 1 to 5 and b is 0 or an integer from 1 to 5; with the proviso that the sum of a and b is not greater than 5; and the ketals of compounds of formulae II, III and IV wherein the ketal moiety has from two to four carbon atoms.

Also included in this invention are pharmaceutically acceptable acid addition salts of compounds of formulae I and II. Representative of such salts are mineral acid salts such as the hydrochloride, hydrobromide, sulfate, nitrate,phosphate; organic acid salts such as the citrate, acetate, sulfosalicylate, tartrate, glycolate, malonate, maleate, fumerate, malate, 2-hydroxy-3-naphthoate, pamoate, salicylate, stearate, phthalate, succinate, gluconate, mandelate, lactate and methane sulfonate.

Compounds having the formulae I, II and III above contain asymmetric centers at the 6a- and/or 10a-positions. There may be additional asymmetric centers in the 3-position substituent (-Z-W), and 5-, 6- and 9-positions. Diastereomers with the 9β-configuration are generally favored over the 9α-isomers because of greater (quantitatively) biological activity. For the same reason, the trans(6a,10a)diastereomers of compounds of formula I are generally favored over the cis (6a,10a)diastereomers. As regards compounds of formula II, when one of $R_4$ and $R_5$ is other than hydrogen, the cis-diastereomers are preferred because of their greater biological activity. As regards formula IV compounds, asymmetric centers exist at the 9-position and in the 3-position substituents. Among the enantiomers of a given compound, one will generally be favored over the other and the racemate because of its greater activity. The enantiomer favored is determined by the procedures described herein. For example, the l-enantiomer of 5,6,6aβ,7,8,9,10,10aα-octahydro-1-acetoxy-9β-hydroxy-6β-methyl-3-(5-phenyl-2-pentyloxy)benzo[c]quinoline is favored over the d-enantiomer and the racemate because of its greater analgesic activity.

Among the 3-position (ZW) diastereoisomers, one will generally be favored over the other. For example, dl-5,6,6aβ,7,8,9α,10,10aα-octahydro-1-acetoxy-9-hydroxy-6β-methyl-3-(1α-methyl-4-phenylbutoxy)benzo[c]quinoline is favored over dl-5,6,6aβ,7,8,9α,10,-10aα-octahydro-1-acetoxy-9-hydroxy-6β-methyl-3-(1β-methyl-4-phenylbutoxy)benzo[c]quinoline and (2′R,6S,6aR)-(−)-1-acetoxy-5,6,6a,7,8,9,10,10a-octahydro-9-hydroxy-6-methyl-3-(5′-phenyl-2′-pentyloxy)benzo[c]quinoline is favored over (2′S,6S,6aR,9R,10AR)-(−)-1-acetoxy-5,6,6a,7,8,9,10,10a-octahydro-9-hydroxy-6-methyl-3-(5′-phenyl-2′-pentyloxy)benzo[c]quinoline because of their greater analgesic activity. For convenience, the above formulae are considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

Further, various intermediates useful in the preparation of compounds of formulae I, II, III and IV are also included in this invention. The intermediates have the formulae

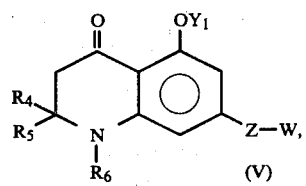

(V)

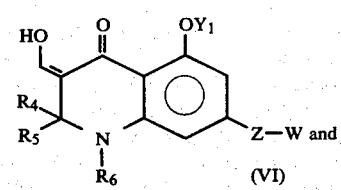

(VI)

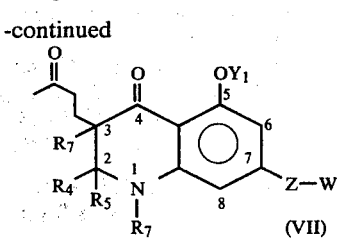

(VII)

wherein $R_4$, $R_5$, $R_6$ and Z-W are as defined above;
$R_7$ is selected from the group consisting of hydrogen and formyl; and
$Y_1$ is selected from the group consisting of hydrogen and hydroxy protecting groups, particularly methyl, ethyl or benzyl.

Asymmetric centers may exist in intermediates V, VI and VII at the 2-position and in the 7-position substituent (—Z—W) and, of course, at other positions, e.g. in the 1-position substituent. The 2- and 7-positions in formulae V-VII correspond to the 6- and 3-positions, respectively, of compounds having formulae I, II, III and IV.

Favored, because of their greater biological activity relative to that of other compounds described herein, are compounds of formulae I and II wherein R and $R_0$ as defined above;
$R_1$ is hydrogen or alkanoyl;
$R_5$ is hydrogen, methyl or ethyl;
and each of $R_4$ and $R_6$ is hydrogen or alkyl;
Z and W have the values shown below:

| Z | m | n | W |
|---|---|---|---|
| alkylene having from 5 to 9 carbon atoms | — | — | H or $CH_3$ |
| alkylene having from 2 to 5 carbon atoms | — | — | $C_6H_5$, 4-$FC_6H_4$, 4-$ClC_6H_4$, 4-pyridyl |
| —(alk$_1$)$_m$—O—(alk$_2$)$_n$— | 1 | 1 | $C_6H_5$, 4-$FC_6H_4$, 4-$ClC_6H_4$, 4-pyridyl |
|  | 0 | 1 |  |
|  | 1 | 0 |  |
| —(alk$_1$)$_m$—O—(alk$_2$)$_n$— | 1 | 1 | H or $CH_3$ |
|  | 0 | 1 | H or $CH_3$ |
|  | 1 | 0 | H or $CH_3$ |

Preferred compounds of formula I are those favored compounds described above wherein R represents hydroxy and which have the trans-configuration. Preferred compounds of formula II are those wherein $R_0$ is oxo.

Especially preferred are those preferred compounds of formulae I and II wherein:
R is hydroxy (formula I only);
$R_1$ is hydrogen or acetyl;
$R_5$ is hydrogen;
$R_4$ is methyl or propyl;
$R_6$ is hydrogen, methyl or ethyl;
when Z is alkylene having from 2 to 5 carbon atoms W is phenyl or 4-pyridyl;
when Z is -(alk$_1$)$_m$-O-(alk$_2$)$_n$- wherein m is 0 and n is 1, (alk$_2$)$_n$ is alkylene having from four to nine carbon atoms, W is hydrogen or phenyl; and
when Z is alkylene having from five to nine carbon atoms, W is hydrogen.

Additionally, the favored and preferred classes of intermediates of formulae III, IV, V, VI and VII are those compounds having said formulae which serve as intermediates for the favored and preferred compounds of formulae I and II.

Compounds of formulae I and II wherein $R_6$ is other than hydrogen, alkyl and —$(CH_2)_x$—$C_6H_5$ also serve as intermediates for formulae I and II compounds wherein $R_6$ is hydrogen, alkyl or —$(CH_2)_x$—$C_6H_5$.

DETAILED DESCRIPTION OF THE INVENTION the compounds of this invention of formula V are prepared from appropriately substituted anilines, e.g., 3-hydroxy-5-(Z-W-substituted)-anilines (VIII) or derivatives thereof in which the 3-hydroxy group is protected by a group ($Y_1$) easily removable to regenerate the hydroxy group. Suitable protective groups are those which do not interfere with subsequent reactions of said 3-(protected hydroxy)-5-substituted anilines and which can be removed under conditions which do not cause undesired reactions at other sites of said compound or of products produced therefrom. Representative protective groups ($Y_1$) are methyl, ethyl, benzyl, substituted benzyl wherein the substituent is, for example, alkyl having from 1 to 4 carbon atoms, halo (Cl, Br, F, I), and alkoxy having from one to four carbon atoms.

The exact chemical structure of the protecting group is not critical to this invention since its importance resides in its ability to perform in the manner described above.

The selection and identification of appropriate protecting groups can easily and readily be made by one skilled in the art. The suitability and effectiveness of a group as a hydroxy protecting group are determined by employing such a group in the above-illustrated reaction sequence. It should, therefore, be a group which is easily removed to permit restoration of the hydroxy groups. Methyl is favored as a protecting alkyl group since it is easily removed by treatment with pyridine hydrochloride. The benzyl group, also a favored protecting group, is removed by catalytic hydrogenolysis or acid hydrolysis.

When Z is -$(alk_1)_m$-X-$(alk_2)_n$-, $Y_1$ is preferably benzyl or a substituted benzyl group since it can subsequently be removed without detriment to the Z group.

The protected aniline derivative (VIII) is then converted to a compound of formula IX by known technology as described herein.

An abbreviated reaction sequence (Flow Sheet A) for preparing representative compounds of formula V beginning with 3-(protected hydroxy)-5-(Z-W-substituted)aniline (VIII) wherein -Z-W is $OCH_3$ is given below:

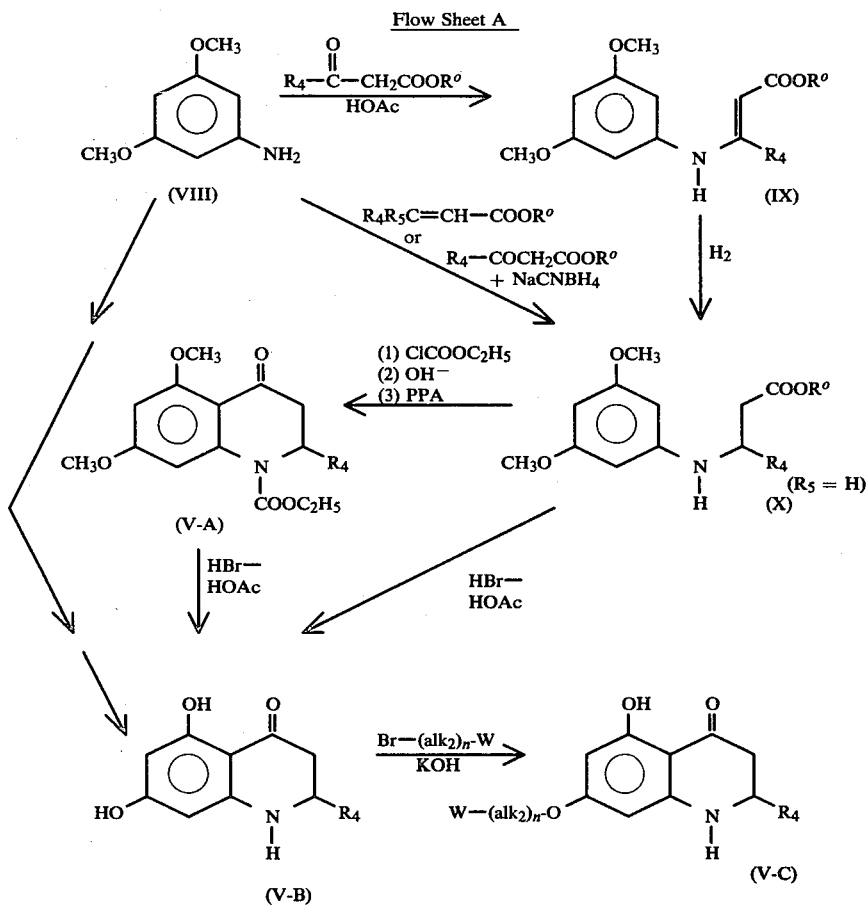

Flow Sheet A $R^o$ in the above flow sheet represents alkyl having from one to six carbon atoms. ($R_5$, for the purpose of illustration in the overall Flow Sheet, is represented as hydrogen. However, in the sequence VIII → X or VIII → V-B, $R_5$ can be hydrogen, methyl or ethyl.)

The 5-substituent of formula VIII compounds can be group —Z—W desired in compounds of formulae II or I, or a group readily convertible to said group. When the Z moiety of group —Z—W is -$(alk_1)_m$-X-$((alk_2)_n$- wherein X is O or S and each of m and n is 0, the 5-substituent, when W is hydrogen, is —XH (i.e., OH or SH) or a protected —XH group of the formula —X—$Y_1$ wherein $R_1$ is as defined above. When, of course, —Z—W is -(alk$_1$)$_m$-X-(alk$_2$)$_n$-W wherein m is 1, n is 0 and W is hydrogen, the 5-substituent becomes -(alk$_1$)$_m$-X-H. The —XH group is advantageously protected in the manner described above.

The appropriate 3-hydroxy-5-substituted anilines discussed above are reacted, preferably in the form of derivatives in which the 3-hydroxy group (and 5-hydroxy group if one is present) is protected as mentioned above in order to achieve satisfactory reactions, with an alkyl β-ketoester, e.g., an alkyl acetoacetate, in the presence of acetic acid to provide the corresponding β-[(3-protected hydroxy)-5-substituted aniline]-β-($R_4$)-acrylate (IX). The reaction is generally conducted in a reaction-inert solvent such as benzene or toluene at temperatures of from about 50° C. to the reflux temperature of the solvent under conditions which result in removal of by-product water. Benzene and toluene are efficient solvents when the reaction is conducted at the reflux temperature, since they permit azeotropic removal of by-product water. Other means of water removal - or effective removal of water - such as molecular sieves can be employed, as can other solvents which permit azeotropic removal of water.

Favored protecting groups for the 3-hydroxy-5-substituted aniline reactants are methyl, ethyl and benzyl groups since the ethers are easily prepared, afford satisfactory yields of compounds of formulae IX and X and are conveniently removed.

The alkyl β-ketoester, preferably one in which the alkyl group has from one to six carbon atoms, is generally used in excess to insure maximum conversion of the aniline reactant to the corresponding alkyl β-anilino-β-($R_4$)-acrylate (IX). Ten to twenty percent excess of alkyl β-ketoester is usually sufficient to achieve satisfactory conversions. Acetic acid is used in catalytic amounts to facilitate reaction.

The alkyl β-anilino-β-($R_4$)-acrylate (IX) is then reduced to the corresponding alkyl-3-[(3-protected hydroxy)-5-substituted anilino]-3-($R_4$)-propionate (X) by, for example, sodium borohydride-acetic acid and catalytic hydrogenation. A preferred catalyst is platinum dioxide since it conveniently permits the reaction to be carried out at low pressures, i.e., at pressures under 50 p.s.i. Other catalysts such as noble metals, e.g., platinum, palladium, rhodium, supported or unsupported, can be used along with pressures of hydrogen ranging from about atmospheric to superatmospheric, e.g., 2000 p.s.i. In addition to such catalysts which are heterogeneous catalysts, this step can be carried out using homogeneous catalysts such as Wilkinson's catalyst, tris(triphenylphosphine)chlororhodium(I).

Of course, when the protecting group or groups are benzyl or substituted benzyl, catalytic hydrogenation will result in their removal. For this reason, methyl or ethyl groups are preferred as protecting groups for the 3- and/or 5-hydroxy groups of formula VIII reactants.

Alternatively, compounds of formula X can be prepared directly from compounds of formula VIII by reaction of formula VIII compounds with an alkyl 3,3-$R_4R_5$-acrylate in acetic acid. The reaction is conveniently carried out by reacting equimolar quantities of the alkyl 3,3-$R_4R_5$-acrylate and disubstituted aniline (VIII) in from 0.1 to 2 equivalents of glacial acetic acid at temperatures ranging from 0° C. to the reflux temperature.

Alternatively, compounds of formula V-B may be prepared directly by condensation of equimolar quantities of VIII with the appropriate substituted acrylic acid ($R_4R_5C$=CH—COOH) in pyridine hydrochloride at 150°–200° C.

In addition, when the $R_4,R_5$ groups are both alkyl, treatment of VIII and the alkyl $R_4R_5$ acrylate in a reaction-inert solvent, e.g. tetrahydrofuran, with mercuric acetate followed by reduction with sodium borohydride gives X.

Direct conversion of compounds of formula VIII to compounds of formula X is also conveniently achieved by treating a 3,5-(diprotected hydroxy)aniline hydrochloride with an excess of an alkyl acetoacetate, e.g. ethyl acetoacetate, in the presence of sodium cyanoborohydride in a solvent such as methanol.

The alkyl 3-anilino-3-($R_4$)-propionate (X) is then cyclized to the corresponding 2-($R_4$)-quinolin-4-one (formula V-A or -B) by means of a suitable cyclizing agent such as polyphosphoric acid (PPA), hydrogen bromide-acetic acid, sulfuric acid, oleum (fuming sulfuric acid), hydrogen fluoride, trifluoroacetic acid, phosphoric acid-formic acid and others known to those skilled in the art. In a modification of this conversion, the alkyl 3-anilino-3-($R_4$)-propionate (X) can be converted to the corresponding acid by, for example, saponification of the ester followed by acidification, prior to cyclization.

The ether protecting, or blocking, groups on the 3-(and 5-)hydroxy groups can be removed at the time of cyclization through the use of hydrobromic acid in acetic acid as cyclizing agent and deblocking agent. Hydrobromic acid, 48% aqueous, is generally used since it affords satisfactory cyclization and deblocking. The reaction is conducted at elevated temperatures and desirably at the reflux temperature. However, when Z is -(alk$_1$)$_m$-X-(alk$_2$)$_n$-cyclization conditions such as polyphosphoric acid or trifluoroacetic acid must be used to avoid cleavage of the ether or thioether linkage.

Alternatively, the protecting group (or groups) can be removed subsequent to the cyclization reaction. Hydrobromic acid-acetic acid is also a favored agent for deblocking at this stage of the overall synthesis. The reaction is carried out as described above.

Other reagents such as hydriodic acid, pyridine hydrochloride or hydrobromide can be used to remove protecting ether groups such as methyl and ethyl groups. When the protecting groups are benzyl or substituted benzyl groups, they can be removed by catalytic hydrogenolysis. Suitable catalysts are palladium or platinum, especially when supported on carbon. Alternatively, they can be removed by solvolysis using trifluoroacetic acid. Of course, when group —Z—W contains sulfur, acid debenzylation is used rather than catalytic debenzylation.

A favored method for the transformation of compounds of formula X to compounds of formula V which affords satisfactory yields and permits use of relatively mild conditions comprises conversion of formula X compounds to N-carbalkoxy derivatives wherein the N-carbalkoxy group has from two to five carbon atoms by reaction with the appropriate alkyl or benzyl chloroformate. The N-carbalkoxy or carbobenzyloxy derivative of formula X is then cyclized by means of a polyphosphoric acid to the corresponding N-carbalkoxy or carbobenzyloxy derivative of formula V compounds. The N-substituted derivatives of formula X compounds can, if desired, be hydrolyzed to the corresponding 3-[(N-substituted)-3-(protected hydroxy)-5-substituted anilino]-3-($R_4$)-propionic acid prior to cyclization. Polyphosphoric acid generally produces maximum cyclization and is a preferred cyclizing agent.

Compounds of formula V in which the hydroxy group or groups are protected and in which the nitrogen atom is substituted with carbalkoxy are treated with hydrobromic acid-acetic acid to give compounds of formula V-A. When the hydroxy protecting group or groups are benzyl or substituted benzyl, regeneration of the hydroxy groups is accomplished by catalytic hydrogenolysis. A carbalkoxy group if present on the nitrogen atom is unchanged by this reaction. It can, if desired, be subsequently removed by treatment with hydrobromic acid-acetic acid or any of a variety of acids or bases. Removal of the benzyl protecting group by treatment with trifluoroacetic acid also removes any N-carbalkoxy group present.

When the —Z—W substituent of formula V compounds is —XH (X=O or S) and it is desired to have said —Z—W substituent represent, in compounds of formulae II or I, a group -X-(alk$_2$)$_n$-W wherein X is O, S, SO or SO$_2$, and W is as previously defined, conversion of group -XH to group -X-(alk$_2$)$_n$-W is conveniently and advantageously undertaken at this point in the overall reaction sequence. Thus, the 7-XH group of formula V-B above represented, for the purposes of illustration, as -OH, is transformed by the Williamson reaction with the appropriate bromide [Br-(alk$_2$)$_n$-W], mesylate or tosylate, to group -O-(alk$_2$)$_n$-W (formula V-C).

Similarly, when group -Z-W of formula V is -(alk$_1$)-X-H, its conversion to -(alk$_1$)-X-(alk$_2$)$_n$-W wherein n is 0 or 1 and W is other than hydrogen is conveniently undertaken at this stage of the reaction sequence via the Williamson reaction.

A variety of groups, such as those included within the definition of $R_6$, can be used in place of carbalkoxy or carbobenzyloxy in this favored method to mask the nitrogen against protonation.

Group $R_6$, if not already present in compounds of formulae V-A, V-B or V-C, can be introduced prior to formation of the hydroxymethylene derivative (formula VI) by reaction with the appropriate Cl-$R_6$ or Br-$R_6$ reactant according to known procedures. Of course, when an acyl, e.g., acetyl, group $R_6$ is desired in products of formulae I or II, such groups are generally introduced at that point in the reaction sequence (Flow Sheet B) following formation of formula II compounds wherein $R_6$ is hydrogen, e.g., by acylation with the appropriate acyl halide according to known procedures.

Compounds of formula V and, of course, of formulae V-A, V-B and V-C, are converted by the following illlustrative sequence (Flow Sheet B) to representative compounds of formulae II and I ($R_5$=H in the illustration).

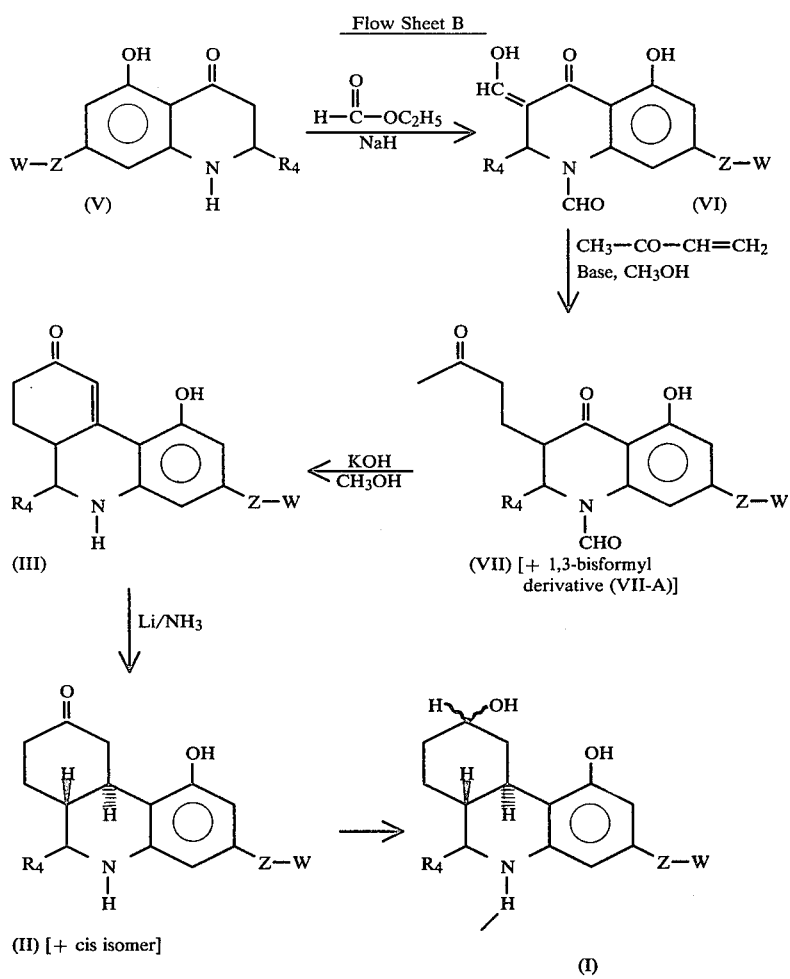

The quinolines of formula V are converted to hydroxymethylene derivatives of formula VI by reaction with ethyl formate and sodium hydride. This reaction, a formylation reaction, produces the bis-formylated derivative (VI) in excellent yield. Treatment of the bis-formylated derivative with methyl vinyl ketone gives a mixture of the corresponding mono-N-formylated Michael adduct (VII) and 1,3-bis-formylated Michael adduct. The two-products are conveniently separated by column chromatography on silica gel.

The conversion of compounds of formula VII to compounds of formula III is achieved by an aldol condensation of the mono-N-formyl compound of formula VII. The 1,3-bis-formylated Michael adduct when subjected to the aldol condensation produces a spiro-annelation product (III-A) as the major product. However, VII-A can be converted to VII by treatment with an equivalent of

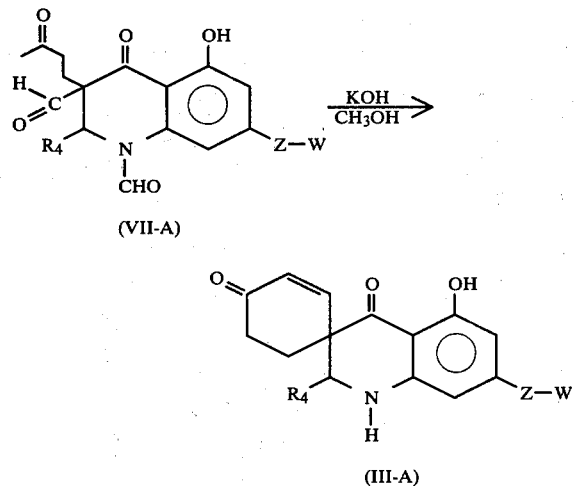

potassium carbonate in methanol.

In addition to the spiro-annelation product, small amounts of the desired enone (formula III) and (V) are also produced.

The enone of formula III is converted by Birch reduction to the compound of formula II. Both the cis- and trans-isomers are produced. This reduction is conveniently carried out using lithium as the metal. Sodium or potassium can also be used. The reaction is conducted at a temperature of from about $-35°$ C. to about $-80°$ C. The Birch reduction is favored because it offers stereoselectivity resulting in formation of the desired trans-ketone of formula II as the major product.

The hydroxy ketones of formula II (compounds wherein $R_0$ is oxo and $R_1$ is hydrogen) and the dihydroxy compounds of formula I ($R=OR_1=OH$) appear to be rather unstable. Upon standing they undergo oxidation as evidenced by formation of purple to red colors. Formation of the colored by-products occurs even when the hydroxy ketone is subjected to sodium borohydride reduction. It has been found that formation of the colored by-products can be prevented by acylation, particularly acetylation, of the 1-hydroxyl group ($OR_1$) with acetic anhydride in pyridine, and by formation of acid addition salts, e.g., hydrochlorides. The acetyl derivatives are stable upon standing and even when subjected to further reaction.

The aforesaid colored by-products are believed to have a quinonoid structure arising from oxidation of the 1-hydroxy group ($OR_1$) to oxo and introduction of a second oxo group at the 2- or the 4-position. The by-products are themselves active as CNS agents, especially as analgesics and tranquilizers, and as hypotensives, and are used in the same manner and at the same dosage levels as are compounds of formulae I and II.

Reduction of the 9-oxo group of compounds of formula II, and preferably for reasons of stability mentioned above, of the acetylated derivative of formula II, via metal hydride reduction affords compounds of formula I wherein the hydroxyl group at the 1-position is present as its acetylated derivative. Sodium borohydride is favored as reducing agent in this step since it not only affords satisfactory yields of the desired product, but retains the acetoxy group at the 1-position, and reacts slowly enough with hydroxylic solvents (methanol, ethanol, water) to permit their use as solvents. A temperature of from about 0° C. to about 30° C. is generally used. Lower temperatures, even down to about $-70°$ C., can be used to increase selectivity of the reduction. Higher temperatures cause reaction of the sodium borohydride with the hydroxylic solvent and deacetylation. If higher temperatures are desired, or required for a given reduction, isopropyl alcohol or the dimethyl ether of diethylene glycol are used as solvents. A preferred reducing agent is potassium tri-sec-butyl borohydride since it favors stereoselective formation of the 9α-hydroxy group. The reduction is conducted in dry tetrahydrofuran at a temperature below about $-50°$ C. using equimolar quantities of the 9-oxo compound and reducing agent.

Reducing agents such as lithium borohydride or lithium aluminum hydride require anhydrous conditions and non-hydroxylic solvents, such as 1,2-dimethoxyethane, tetrahydrofuran, ether, dimethyl ether of ethylene glycol.

Alternately, and more desirably, compounds of formula III, especially those wherein the 1-hydroxy group is protected as an ester or benzyl ether, are converted to compounds of formula I by catalytic hydrogenation. A convenient procedure comprises catalytic hydrogenation over palladium, e.g. palladium-on-carbon, or other noble metal, supported or unsupported. As especially preferred procedure for producing the compounds of formula I having an $R_4$ and R substituent $\beta$ and a trans (6$a$,10$a$) ring structure in good yield with a high degree of stereoselectivity comprises reducing the corresponding formula III compound ($R_4$ is $\beta$, $R_5=H$) in methanol with from $\frac{1}{2}$ to equal amounts by weight of Pd/C in a hydrogen atmosphere.

The acetylated derivatives of formula I thus produced are converted to the corresponding hydroxy derivatives by cleavage of the acetyl group by standard methods.

The isomeric 9-α- and 9-β-hydroxy compounds having formula I are produced in the above-described reducing steps. Treatment of the keto compounds of formulae II-IV with the appropriate alkylene glycol or alkylene dithiol having two to four carbon atoms in the presence of a dehydrating agent such as p-toluenesulfonic acid, or other acid, used in ketalization (oxalic, adipic), affords the corresponding ketals or thioketals (Fahrenholtz et al., *J. Am. Chem. Soc.*, 89, 5934 [1967]).

Compounds of formula I wherein R is hydroxymethyl are prepared via the Wittig reaction of the corresponding 9-oxo compound of formula II with methylenetriphenylphosphorane or other appropriate methylide. The reaction is conducted under relatively mild conditions to produce the corresponding 9-methylene compound. Hydroboration-oxidation of the 9-methylene compound then affords the hydroxymethyl derivative. Borane in tetrahydrofuran is favored for the hydroboration step since it is commercially available and gives satisfactory yields of the desired hydroxymethyl compound. The reaction is generally conducted in tetrahydrofuran or diethylene glycol dimethyl ether (diglyme). The borane product is not isolated but is directly oxidized with alkaline hydrogen peroxide to the hydroxymethyl compound.

Compounds of formulae I and II, including those wherein each of $R_4$ and $R_5$ is alkyl, are also prepared by the sequence of Flow Sheet C below:

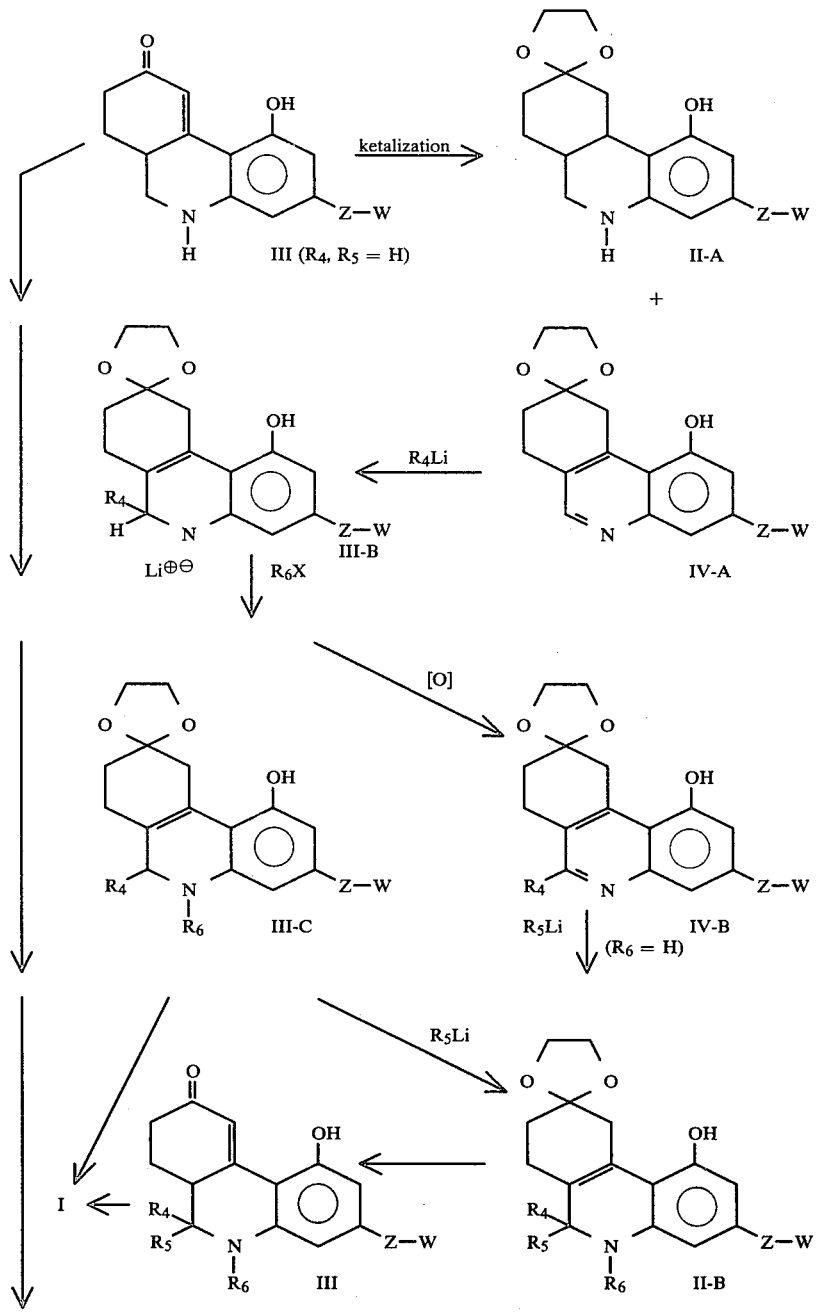

Flow Sheet C

Flow Sheet C

-continued

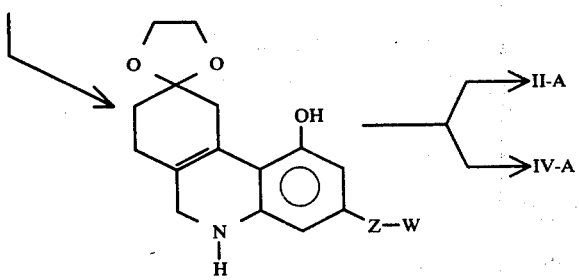

The first step of this sequence comprises conversion of the previously described enones (formula III, Flow Sheet B) to the corresponding ketals by reaction with an appropriate alkylene glycol (e.g., ethylene glycol) in the presence of approximately equivalent amounts of p-toluenesulfonic acid or other acid commonly used for ketal formation as described above in benzene with azeotropic removal of water. A mixture of two ketals is obtained; II-A, the reduced form, and IV-A, the oxidized form. Formation of IV-A is favored by addition of agents such as air, Pd/C, sulfur or 2,3-dichloro-5,6-dicyanobenzoquinone to the reaction mixture. The exclusion of oxidizing agents from the reaction mixture or the addition of reducing agents to the reaction mixture favors formation of II-A.

Deketalization of formulae II-A and IV-A compounds by procedures known to those skilled in the art affords compounds of formulae II and IV. These latter compounds are then converted to compounds of formulae I and IV by the procedures of Flow Sheet B.

The reduced formula II-A compounds are oxidized (dehydrogenated) by a variety of oxidants, including iodine, by standard techniques to produce formula IV-A compounds.

The heteroaromatic system of compounds of formula IV-A readily adds organometallic reagents to the azomethine bond. Organolithium reagents, e.g. methyl and ethyl lithium, react with IV-A to produce adducts of formula III-B. Oxidation of the thus-formed adduct by various oxidizing agents, conveniently air, aromatizes the adduct to give formula IV-B substituted in the 6-position. Further reaction of the 6-substituted IV-B compounds with organolithium reagents affords the 6,6-disubstituted products of formula II-B.

The addition of the second group ($R_5$) to the 6-position, particularly when $R_5$ is larger than methyl, is facilitated by activation of the azomethine bond by quaternization. Activation is conveniently achieved by reaction of formula III-B with an alkyl halide (e.g. methyl or ethyl iodide), or an aralkyl halide, desirably an aralkyl bromide [$C_6H_5(CH_2)_xBr$] such as benzyl bromide to give formula III-C compounds substituted in the 5-position. The thus-activated compounds readily react with an excess of organolithium or Grignard reagents (see Hoops, et al., *J. Org. Chem.*, 33, 2955-6, 1968) to provide trisubstituted formula II-B compounds. Hydrolysis of the ketals of formulae II-B and III-C affords the corresponding enones which are converted to formulae II and I compounds by procedures described above. Of course, when $R_6$ of formulae III or III-C compounds is benzyl, lithium-ammonia reduction of the enone also cleaves the benzyl group.

A further procedure for introduction of alkyl groups at the 6-position with ultimate production of compounds of formulae I and II is that of Flow Sheet D:

Flow Sheet D

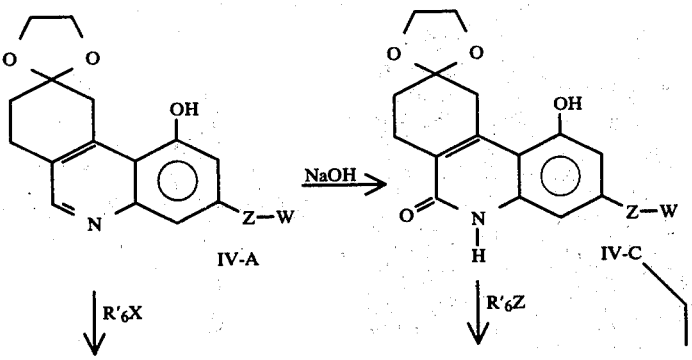

Flow Sheet D

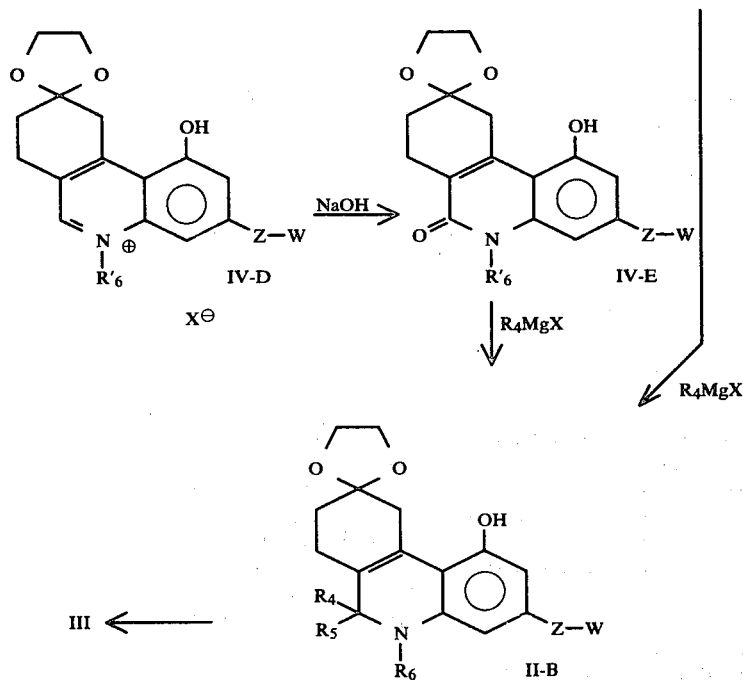

The 6-oxohexahydrobenzo[c]quinolines of formulae IV-C and IV-E are prepared from compounds of formula IV-A and IV-D by reacting them with sodium or potassium hydroxide at elevated temperatures, e.g. at about 200°–300° C. Quaternization of the nitrogen of IV-A, by reacting IV-A with methyl or ethyl iodide, benzyl bromide or other aralkyl halide, permits the reaction with sodium or potassium hydroxide to be carried out under milder conditions. The intermediate adduct formed is easily oxidized with mild oxidizing agents, including air, to the oxo compound of formula IV-E but which, of course, as a result of the quaternization reaction, bears a substituent (methyl, ethyl, aralkyl) on the nitrogen atom.

An alternative procedure comprises treating IV-A with a peracid, e.g. m-chloroperbenzoic acid, peracetic, to form the corresponding N-oxide which is then reacted with acetic anhydride in an N-oxide rearrangement to give IV-C (Boelkelheide Rearrangement). Other methods known to those skilled in the art can be used for the conversion of N-oxides to lactams.

Compounds of formula IV-C or IV-E are then treated with an excess of an appropriate Grignard reagent, e.g. methyl or ethyl magnesium bromide, to give the corresponding 6,6-dialkyl compound II-B.

The 3-hydroxy-5-(Z-W-substitutted)anilines are prepared from corresponding 5-(Z-W-substituted)resorcinols via the Bucherer Reaction which comprises reacting the appropriate 5-(Z-W-substituted) resorcinol with aqueous ammonium sulfite or bisulfite. The reaction is conducted in an autoclave at elevated temperatures, e.g. from about 150° to about 230° C. The aniline product is isolated by acidifying the cooled reaction mixture and extracting the acid mixture with, for example, ethyl acetate. The acid solution is neutralized and extracted with a suitable solvent, e.g. chloroform, to recover the aniline product. Alternatively, the aniline product is isolated by extracting the cooled reaction mixture with an appropriate solvent followed by column chromatography of the crude product.

The 5-(Z-W-substituted)resorcinols, if not known, are prepared from 3,5-dihydroxybenzoic acid. The procedure comprises esterifying 3,5-dihydroxybenzoic acid in which the hydroxy groups are protected (e.g., as methyl, ethyl or benzyl ethers); or alternatively, amidating the 3,5-[di(protected hydroxy)]benzoic acid.

The overall abbreviated sequence is illustrated below (Flow Sheet E):

Flow Sheet E

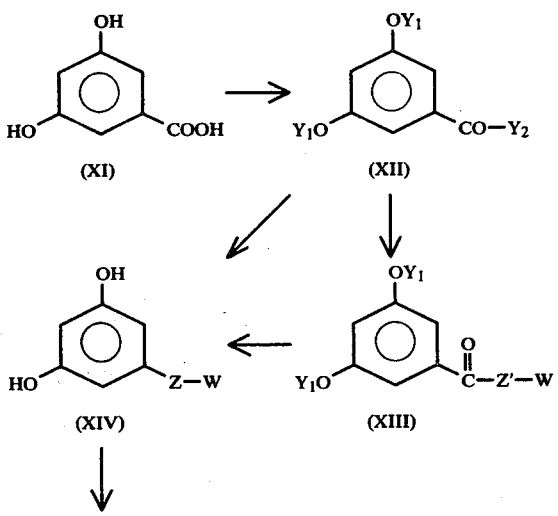

-continued
Flow Sheet E

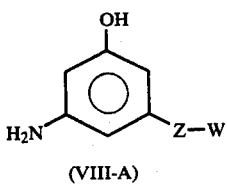

(VIII-A)

The starting material, 3,5-dihydroxybenzoic acid XI is converted to a compound of formula XII wherein $Y_2$ represents an alkoxy group, desirably methoxy or ethoxy for ease of preparation, or an amino group; and $Y_1$ is a hydroxy protecting group, by methods described in the literature.

The diprotected benzoic acid derivative XII is then converted to a compound of formula XIV by known technology. In one procedure XII is hydrolyzed to the corresponding acid ($Y_2$=OH), or lithium salt, and reacted with the appropriate alkyl lithium to produce an alkyl disubstituted phenyl ketone ($Y_2$=alkyl). When methyl lithium is used, the resulting acetophenone derivative is treated with a Grignard Reagent (W—Z'—MgBr). The intermediate adduct is hydrolyzed to the corresponding alcohol which is then hydrogenolyzed to replace the hydroxy group with hydrogen. This procedure is especially useful for those compounds wherein Z is alkylene.

The ether groups are deblocked by suitable means: treatment with pyridine hydrochloride ($Y_1$=methyl) or catalytic hydrogenolysis ($Y_1$=benzyl), or by treatment with an acid such as trifluoroacetic acid, hydrochloric, hydrobromic or sulfuric acids. Acid debenzylation is, of course, used when the group —Z—W contains sulfur.

A further method for converting compounds of formula XII to those of formula XIV comprises reaction of a ketone of formula XII ($Y_2$=alkyl) with the appropriate triphenyl phosphonium bromide derivative $[(C_6H_5)_3P^+$—Z—W]$^-$Br in the presence of a base (e.g., sodium hydride). The reaction proceeds via an alkene which is subsequently catalytically hydrogenated to the corresponding alkane (Z—W) and deblocked to the dihydroxy compound XIV. Of course, when —Z— is $(alk_1)_m$—X—$(alk_2)_n$ and $Y_1$ is benzyl, the catalytic hydrogenation also results in cleavage of the benzyl ethers.

Alternatively, conversion of structure XII compounds to those of structure XIV can be achieved by the sequence XII→XIII→XIV. In this sequence, the diprotected benzamide (XII,$Y_2$=NH$_2$) is converted to the ketone (XIII,Z'=Z less one CH$_2$ group) by reaction with the appropriate Grignard reagnet (BrMg—Z'—W) followed by reaction with methyl- or ethyl-magnesium halide to form the corresponding carbinol. Dehydration of the carbinol, e.g., with p-toluenesulfonic acid, affords the corresponding alkene which is then catalytically hydrogenated (Pd/C) to the alkane (XIV). The ether groups are deblocked (converted to hydroxy) as described above.

When Z is alkylene, $Y_1$ is desirably alkyl having from one to four carbon atoms or benzyl. The function of group $Y_1$ is to protect the hydroxy groups during subsequent reactions. It is its ability to perform a specific function; i.e., protection of the hydroxy groups, rather than its structure which is important. The selection and identification of appropriate protecting groups can easily and readily be made by one skilled in the art. The suitability and effectiveness of a group as a hydroxy protecting group are determined by employing such a group in the above-illustrated reaction sequence. It should, therefore, be a group which is easily removed to permit restoration of the hydroxy groups. Methyl is favored as a protecting alkyl group since it is easily removed by treatment with pyridine hydrochloride. The benzyl group if used as a protecting group, is removed by catalytic hydrogenolysis or acid hydrolysis.

When Z is -(alk$_1$)$_m$—X—(alk$_2$)$_n$—, $Y_1$ is preferably benzyl or a substituted benzyl group since it can subsequently be removed without detriment to the Z group.

Formula VIII-A compounds can, alternatively, be prepared from 3-amino-5-hydroxybenzoic acids via the procedure of Flow Sheet F below.

Compounds of formula VIII-A wherein —Z—W is -alkylene-W or -(alk$_1$)—X'—(alk$_2$)$_n$—W wherein (alk$_1$), (alk$_2$), W and n are as defined above and X' is O or S, are obtained by the following sequence (Flow Sheet F):

Flow Sheet F
(Ac = acetyl)

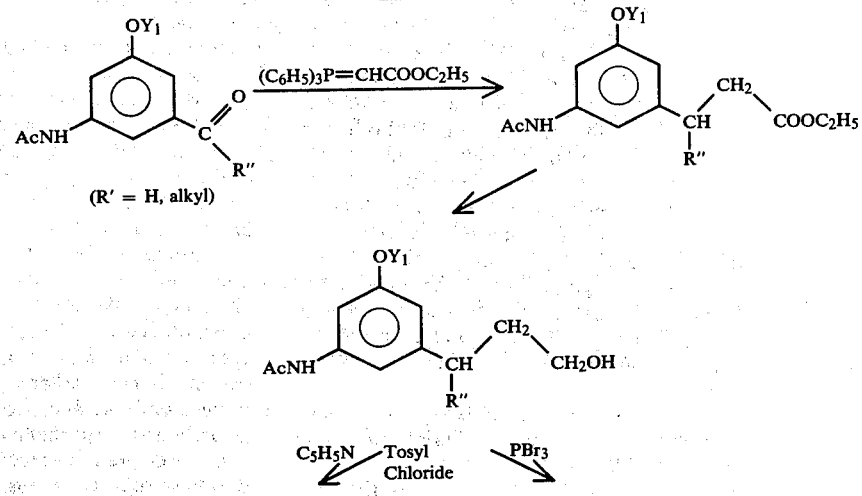

Flow Sheet F
(Ac = acetyl)

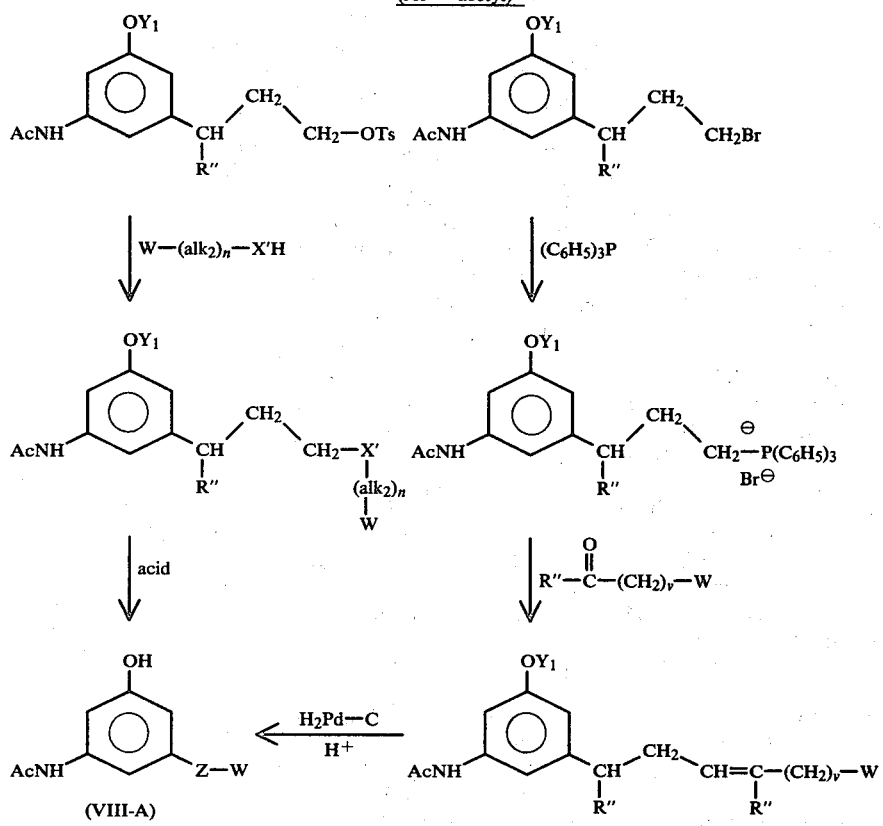

The first step in the above sequence (the Wittig reaction) provides opportunity, by choice of appropriate reactants, to produce compounds having straight or branched alkylene groups. The amino group is protected by acetylation according to standard procedures. In the given illustration, the value of R" as methyl or ethyl permits formation of a compound having alkyl substitution on the carbon atom ($\alpha$) adjacent to the phenyl group. Substitution of a methyl or ethyl group at other sites, e.g., the $\beta$-carbon atoms of the alkylene group, is achieved by choice of the appropriate carboalkoxy alkylidene triphenylphosphorane, e.g. $(C_6H_5)_3P=C(R")$—$COOC_2H_5$. The unsaturated ester thus produced is reduced to the corresponding saturated alcohol by reaction with lithium aluminum hydride. The presence of a small amount of aluminum chloride sometimes accelerates this reaction. Alternatively, when $Y_1$ is other than benzyl (e.g. methyl), the alcohol is produced by catalytic reduction of the unsaturated ester using palladium-carbon, followed by treatment of the saturated ester thus produced with lithium aluminum hydride. Conversion of the alcohol to the corresponding tosylate or mesylate followed by alkylation of the tosylate or mesylate with an alkali metal salt of the appropriate $HX'-(alk_2)_n-W$ reactant, and finally removal of the protecting groups ($Y_1$) affords the desired compound VIII-A. When $X'$ is sulfur, the protecting group $Y_1$ is methyl.

A variation of the above sequence comprises bromination of the alcohol rather than converting it to a tosylate or mesylate. Phosphorous tribromid is a convenient brominating agent. The bromo derivative is then reacted with the appropriate $HX'-(alk_2)_n-W$ in the presence of a suitable base (Williamson reaction).

The bromo compounds also serve as valuable intermediates for increasing the chain length of the alkylene moiety in the above sequence to give compounds wherein Z is -alkylene-W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound.

In this variation, the value of the protecting group ($Y_1$) selected depends upon the particular sequence followed. When the vertical sequence on the right is used, benzyl is the preferred protecting group by reason of the catalytic hydrogenation step. Methyl is the preferred protecting group when the left vertical sequence is followed, since it is conveniently removed by treatment with acid as described herein.

Compounds of formula II wherein —Z—W is $-(alk_1)_m-X-(alk_2)_n-W$ and X is —SO— or —$SO_2$— are obtained by oxidation of the corresponding compounds in which X is —S—. Hydrogen peroxide is a convenient agent for oxidation of the thio ethers to sulfoxides. Oxidation of the thio ethers to corresponding sulfones is conveniently accomplished by means of a peracid such as perbenzoic, perphthalic or m-chloroperbenzoic acid. This latter peracid is especially useful since the by-product m-chlorobenzoic acid is easily removed.

Esters of compounds of formulae II–IV wherein $R_1$ is alkanoyl or $-CO-(CH_2)_p-NR_2R_3$ are readily prepared by reacting formulae II–IV compounds with the appropriate alkanoic acid or acid of formula $HOOC-(CH_2)_p-NR_2R_3$ in the presence of a condensing agent such as dicyclohexylcarbodiimide. Alternatively they are prepared by reaction of a formula II–IV compound with the appropriate alkanoic acid chloride or anhydride, e.g., acetyl chloride or acetic anhydride, in the presence of a base such as pyridine.

Esters of formula I compounds in which each of the R and $R_1$ groups is esterified are prepared by acylation according to the above-described procedures. Compounds in which only the 9-hydroxy group is acylated are obtained by mild hydrolysis of the corresponding 1,9-diacyl derivative, advantage being taken of the greater ease of hydrolysis of the phenolic acyl group. Formula I compounds in which only the 1-hydroxy group is esterified are obtained by borohydride reduction of the corresponding formula II ketone esterified at the 1-position. The thus-produced formula I compounds bearing 1-acyl-9-hydroxy substitution or 1-hydroxy-9-acyl substitution can then be acylated further with a different acylating agent to produce a diesterified compound of formula I in which the ester group at the 1- and the 9-positions are different.

The presence of a basic group in the ester moiety ($OR_1$) in the compounds of this invention permits formation of acid-addition salts involving said basic group. When the herein described basic esters are prepared via condensation of the appropriate amino acid hydrochloride (or other acid addition salt) with the appropriate compound of formula I–IV in the presence of a condensing agent, the hydrochloride salt of the basic ester is produced. Careful neutralization affords the free base. The free base form can then be converted to other acid addition salts by known procedures.

Acid addition salts can, of course, as those skilled in the art will recognize, be formed with the nitrogen of the benzo[c]quinoline system. Such salts are prepared by standard procedures. The basic ester derivatives are, of course, able to form mono- or di-acid addition salts because of their dibasic functionality.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound the mouse is observed for the first "flicking" movements of one or both hind feet, or until 10 seconds elaspe without such movements. Morphine has an $MPE_{50}=4–5.6$ mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941), using controlled high intensity heat applied to the tail. Each mouse is placed in a snug-fitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., *Arch. Int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch*

Med. Wschr., 55, 731–732 (1929) is used to ascertain the effects of the test compound on aggressive attacking responses elicited by a stimulus pinching the tail. Male albino rats (50–60 g.) of the Charles River (Sprague-Dawley) CD-strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded as 30 seconds. Morphine is active 17.8 mg./kg. (i.p.).

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \, MPE = \frac{\text{test time} - \text{control time}}{\text{cutoff time} - \text{control time}} \times 100$$

In the tables below, the analgesic activity is reported in terms of $MPE_{50}$, the dose at which half of the maximal possible analgesic effect is observed in a given test.

The compounds of the present invention are active analgesics via oral and parenteral administration and are conveniently administered in composition form. Such compositions include a pharmaceutical carrier selected on the basis of the chosen route of administration and standard pharmaceutical practice. For example, they may be administered in the form of tablets, pills, powders or granules containing such excipients as starch, milk sugar, certain types of clay, etc. They may be administered in capsules, in admixtures with the same or equivalent excipients. They may also be administered in the form of oral suspensions, solutions, emulsions, syrups and elixirs which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults may range from 0.01 to 500 mg. per day in single or divided doses. In many instances, it is not necessary to exceed 100 mg. daily. The favored oral dosage range is from about 0.01 to about 300 mg./day; the preferred range is from about 0.10 to about 50 mg./day. The favored parenteral dose is from about 0.01 to about 100 mg./day; the preferred range from about 0.01 to about 20 mg./day.

By means of the above procedures, the analgesic activity of several compounds of this invention and of certain prior art compounds are determined.

The following abbreviations are used in the tables:
PBQ=phenylbenzoquinone-induced writhing; TF=tail flick; HP=hot plate; RTC=rat tail clamp; FJ=flinch jump; and TI=tail immersion assays.

TABLE I

Analgesic Activity ($MPE_{50}$-mg./kg.,s.c.)

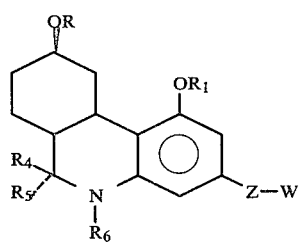

| R | $R_1$ | $R_4$ | $R_5$ | $R_6$ | Z—W | 6a,10a | PBQ | TF | HP |
|---|---|---|---|---|---|---|---|---|---|
| H | H | $CH_3$ | H | H | —O—$CH(CH_3)C_5H_{11}$ | cis/trans | 1.05 | 1.32 | 10–32 |
| H | $COCH_3$ | $CH_3$ | H | H | —O—$CH(CH_3)C_5H_{11}$ | trans | 1.0–1.78 | 1.0 | 5.6 |
| H | $COCH_3$ | $CH_3$ | H | H | —O—$CH(CH_3)C_5H_{11}$ | trans* | 100 @ 10 | 5.6 | 5.6 |
| H | H | $CH_3$ | H | H | —O—$CH(CH_3)C_5H_{11}$ | trans | 0.5 | 3.2 | 10 |
| $COCH_3$ | $COCH_3$ | $CH_3$ | H | H | —O—$CH(CH_3)C_5H_{11}$ | trans | 1.78–3.2 | 10 | >10 |
| $COCH_3$ | $COCH_3$ | $CH_3$ | H | H | —$OCH(CH_3)C_5H_{11}$ | trans* | <10 | 5.6–10 | >10 |
| H | H | $CH_3$ | H | $COCH_3$ | —O—$CH(CH_3)C_5H_{11}$ | trans | >10 | >10 | >10 |
| $COCH_3$ | $COCH_3$ | $CH_3$ | H | $CH_3$ | —O—$CH(CH_3)C_5H_{11}$ | trans | 100 @ 10 | 1–3.2 | 3.2–5.6 |
| H | H | $CH_3$ | H | H | —O—$CH(CH_3)(CH_2)_3C_6H_5$ | trans | 0.1–0.56 | 1–3.2 | 1–3.2 |
| H | $COCH_3$ | $CH_3$ | H | H | —O—$CH(CH_3)(CH_2)_3C_6H_5$ | trans* | 0.25 | 0.42 | 1–3.2 |
| H | $COCH_3$ | $CH_3$ | H | H | —O—$CH(CH_3)(CH_2)_3C_6H_5$ | cis | 0.56–1.0 | 1–3.2 | 3.2–10 |
| H | H | $CH_3$ | H | $C_2H_5$ | —$OCH(CH_3)C_5H_{11}$ | trans | 0.09 | | |
| H | $COCH_3$ | H | H | H | —$OCH(CH_3)C_5H_{11}$ | trans | 10 | >10 | >10 |
| H | $COCH_3$ | $CH_3$ | H | $CH_3$ | —$OCH(CH_3)(CH_2)_3C_6H_5$ | trans* | 0.05 | | |

TABLE I-continued

Analgesic Activity (MPE₅₀-mg./kg.,s.c.)

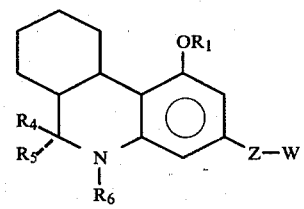

| R | R₁ | R₄ | R₅ | R₆ | Z—W | 6a,10a | PBQ | TF | HP |
|---|---|---|---|---|---|---|---|---|---|
| H | COCH₃ | H | H | H | —OCH(CH₃)(CH₂)₃C₆H₅ | trans | 0.83 | | |
| H | COCH₃ | H | H | CH₃ | —OCH(CH₃)(CH₂)₃C₆H₅ | trans | 0.1 | 0.32–0.56 | 0.56–1.0 |
| H | COCH₃ | H | H | CH₃ | —OCH(CH₃)C₅H₁₁ | trans | 100 @ 3.2 | 100 @ 10 | <10 |
| morphine | | | | | | | 0.8 | 3.2–5.6 | 4.0–5.6 |
| H | H | CH₃ | H | COC₆H₅ | —O—CH(CH₃)C₅H₁₁ | trans | >10 | | |
| H | COCH₃ | H | H | CH₃ | —O—CH(CH₃)(CH₂)₃C₆H₅ | trans | 0.098 | 0.32 | |
| H | COCH₃ | CH₃ | H | CH₃ | —O—CH(CH₃)(CH₂)₃C₆H₅ | trans* | 0.05 | 0.016 | |
| H | COCH₃ | CH₃ | H | H | —O—(CH₂)₄C₆H₅ | trans | 6.09 | | |
| COCH₃ | COCH₃ | CH₃ | H | H | —O—(CH₂)₄C₆H₅ | trans | >56 | | |
| H | COCH₃ | CH₃ | H | CH₃ | —O—(CH₂)₄C₆H₅ | trans | 0.28 | 1.46 | |
| H | H | CH₃ | H | CH₃ | —O—(CH₂)₄C₆H₅ | trans | 0.80 | 2.1 | |
| COCH₃ | COCH₃ | H | H | i-C₄H₉ | —O—CH(CH₃)(CH₂)₃C₆H₅ | trans | >10 | | |
| H⁺ | COCH₃ | H | H | H | —O—CH(CH₃)C₅H₁₁ | cis | ≦10 | >10 | |
| H⁺ | COCH₃ | CH₃ | H | H | —O—CH(CH₃)(CH₂)₃C₆H₅ | trans | 1.64 | 7.65 | |
| H | COCH₃ | H | CH₃ | H | —O—CH(CH₃)(CH₂)₃C₆H₅ | trans | 0.11 | | |
| H | COCH₃ | H | CH₃ | H | —O—CH(CH₃)(CH₂)₃C₆H₅ | cis | 0.22 | | |
| H⁺ | COCH₃ | CH₃ | H | H | —O—CH(CH₃)(CH₂)₃C₆H₅ | cis | 0.46 | | |
| H⁺ | COCH₃ | H | CH₃ | H | —O—CH(CH₃)(CH₂)₃C₆H₅ | trans | 0.78 | | |
| H | COCH₃ | n-C₃H₇ | H | H | —O—CH(CH₃)(CH₂)₃C₆H₅ | trans* | 0.14 | 0.34 | |
| H | COCH₃ | n-C₃H₇ | H | H | —O—CH(CH₃)(CH₂)₃C₆H₅ | cis* | 0.12 | 0.44 | 0.61 |
| H | COCH₃ | CH₃ | H | H | —O—CH(CH₃)(CH₂)₃C₆H₅ | trans(a) | 0.14 | 0.26 | |
| H | COCH₃ | CH₃ | H | H | —O—CH(CH₃)(CH₂)₃C₆H₅ | trans(b) | 7.40 | | |
| H | OH | CH₃ | H | C₂H₅ | —O—CH(CH₃)(CH₂)₃C₆H₅ | trans* | 0.21 | 1.47 | 3.64 |
| H | OH | CH₃ | H | (CH₂)₂C₆H₅ | —O—CH(CH₃)(CH₂)₃C₆H₅ | trans | 14.33 | | |
| H | OH | CH₃ | H | (CH₂)₃C₆H₅ | —O—CH(CH₃)(CH₂)₃C₆H₅ | trans | 29 @ 10 | | |
| H | OH | CH₃ | H | CH₂C₆H₅ | —O—CH(CH₃)(CH₂)₃C₆H₅ | trans | 0.50 | | |
| H | OH | CH₃ | H | n-C₃H₇ | —O—CH(CH₃)(CH₂)₃C₆H₅ | trans | 100 @ 0.32 | | |
| H | OH | CH₃ | H | C₆H₁₃ | —O—CH(CH₃)(CH₂)₃C₆H₅ | trans | 1.29 | | |
| H | OH | CH₃ | H | C₅H₁₁ | —O—CH(CH₃)(CH₂)₃C₆H₅ | trans | 27.85 | | |
| H | OH | CH₃ | H | (CH₂)₄C₆H₅ | —O—CH(CH₃)(CH₂)₃C₆H₅ | trans | 60 @ 56 | | |
| H | OH | CH₃ | H | C₄H₉ | —O—CH(CH₃)(CH₂)₃C₆H₅ | trans | 42.36 | | |
| H | OH | CH₃ | H | CH₃ | —O—CH(CH₃)(CH₂)₃C₆H₅ | trans | 100 @ .56 | | |
| H | COCH₃ | C₂H₅ | H | H | —O—CH(CH₃)(CH₂)₃C₆H₅ | trans* | 0.15 | 0.73 | 1.59 |
| H | COCH₃ | C₆H₁₃ | H | H | —O—CH(CH₃)(CH₂)₃C₆H₅ | trans* | 32 | | |
| H⁺ | COCH₃ | CH₃ | H | CH₃ | —O—CH(CH₃)(CH₂)₃C₆H₅ | trans* | 0.11 | | |
| H⁺ | COCH₃ | CH₃ | H | CH₃ | —O—CH(CH₃)(CH₂)₃C₆H₅ | cis* | 0.82 | | |
| H | COCH₃ | CH₃ | H | CH₃ | —O—CH(CH₃)(CH₂)₃C₆H₅ | cis* | 45 @ 56 | | |
| H | COCH₃ | (CH₂)₂C₆H₅ | H | H | —O—CH(CH₃)(CH₂)₃C₆H₅ | trans* | 3.56 | | |
| H | COCH₃ | CH₃ | H | H | —O—(CH₂)₃C₆H₅ | trans* | 50 @ 10 | | |
| H | COCH₃ | C₅H₁₁ | H | H | —O—CH(CH₃)(CH₂)₃C₆H₅ | trans* | 18.01 | | |
| H | COCH₃ | C₄H₉ | H | H | —O—CH(CH₃)(CH₂)₃C₆H₅ | trans* | | 3.05 | 7.94 |
| H | COCH₃ | H | C₄H₉ | H | —O—CH(CH₃)(CH₂)₃C₆H₅ | trans* | 1.32 | 3.76 | |
| H | COCH₃ | CH₃ | H | H | —O—CH(CH₃)(CH₂)₃C₆H₅(c) | trans* | 0.22 | 0.23 | |
| H | COCH₃ | CH₃ | H | H | —O—CH(CH₃)(CH₂)₃C₆H₅(d) | trans* | 1.73 | 1.69 | |
| H | COCH₃ | CH₃ | H | H | —O—CH(CH₃)(CH₂)₃C₆H₅(d) | trans(a) | 1.50 | | |
| H | COCH₃ | CH₃ | H | H | —O—CH(CH₃)(CH₂)₃C₆H₅(c) | trans(b) | 0.07 | 0.21 | 0.44 |
| H | COCH₃ | CH₃ | H | CH₃ | —O—CH(CH₃)(CH₂)₃C₆H₅(c) | trans | 0.01 | 0.04 | 0.09 |
| H | COCH₃ | CH₃ | H | H | —C(CH₃)₂(CH₂)₄CH₃ | trans | 0.19 | | |
| H | COCH₃ | CH₃ | H | CH₃ | —C(CH₃)₂(CH₂)₄CH₃ | trans* | 0.13 | | |
| H | COCH₃ | CH₃ | H | H | —O—(CH₂)₂C₆H₇ | trans* | 16 @ 56 | | |
| H | COCH₃ | C₄H₉ | H | CH₃ | —O—CH(CH₃)(CH₂)₃C₆H₅ | trans* | 0.89 | | |
| H | COCH₃ | C₃H₇ | H | CH₃ | —O—CH(CH₃)(CH₂)₃C₆H₅ | trans* | 0.08 | | |

*hydrochloride salt
⁺9α-OH
(a)6S,6aR,9R,10aR
(b)6R,6aS,9S,10aS (c) —O—C(CH₃)(H)—(CH₂)₃C₆H₅

(d) —O—C(H)(CH₃)—(CH₂)₃C₆H₅

TABLE II

Analgesic Activity (MPE$_{50}$-mg./kg.,s.c.)

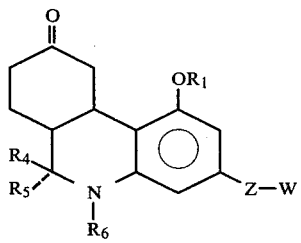

| R$_1$ | R$_4$ | R$_5$ | R$_6$ | Z—W | 6a,10a | PBQ | TF | HP |
|---|---|---|---|---|---|---|---|---|
| H | CH$_3$ | H | H | —O—CH(CH$_2$)C$_5$H$_{11}$ | cis/trans | 3.2 | | |
| COCH$_3$ | CH$_3$ | H | H | —O—CH(CH$_3$)C$_5$H$_{11}$ | cis | 100 @ 10 | | |
| COCH$_3$ | CH$_3$ | H | H | —O—CH(CH$_3$)C$_5$H$_{11}$ | 10 | >10 | >10 | |
| COCH$_3$ | CH$_3$ | H | COCH$_3$ | —O—CH(CH$_3$)C$_5$H$_{11}$ | trans | >10 | >10 | >10 |
| H | CH$_3$ | H | CH$_3$ | —O—CH(CH$_3$)C$_5$H$_{11}$ | trans | 100 @ 10 | ~10 | ~10 |
| COCH$_3$ | CH$_3$ | H | H | —O—CH(CH$_2$)(CH$_2$)$_3$C$_6$H$_5$ | cis | 0.1–0.56 | 3.2–5.6 | 10 |
| COCH$_3$ | CH$_3$ | H | H | —O—CH(CH$_2$)(CH$_2$)$_3$C$_6$H$_5$ | trans | 1.78 | 2.4 | <10 |
| COCH$_3$ | H | H | CH$_3$ | —O—CH(CH$_3$)C$_5$H$_{11}$ | trans | 100 @ 10 | | |
| COCH$_3$ | H | H | H | —O—CH(CH$_3$)(CH$_2$)$_3$C$_6$H$_5$ | trans | 100 @ 10 | 1.0–3.2 | >10 |
| COCH$_3$ | H | H | H | —O—CH(CH$_3$)(CH$_2$)$_3$C$_6$H$_5$ | cis | 100 @ 28 | | |
| COCH$_3$ | CH$_3$ | H | H | —O—CH(CH$_3$)(CH$_2$)$_3$C$_6$H$_5$ | cis* | 0.31 | 3.9 | |
| H | CH$_3$ | H | COCH$_3$ | —O—CH(CH$_3$)C$_5$H$_{11}$ | trans | >10 | >10 | |
| COCH$_3$ | H | H | H | —O—CH(CH$_3$)C$_5$H$_{11}$ | trans | >10, <56 | >10 | |
| COCH$_3$ | CH$_3$ | H | COC$_6$H$_5$ | —O—CH(CH$_3$)C$_5$H$_{11}$ | trans | >10 | | |
| H | CH$_3$ | H | COC$_6$H$_5$ | —OCH(CH$_3$)C$_5$H$_{11}$ | trans | >10 | | |
| COCH$_3$ | CH$_3$ | H | CH$_3$ | —O—CH(CH$_3$)(CH$_2$)$_3$C$_6$H$_5$ | trans* | 0.17 | | |
| COCH$_3$ | H | H | CH$_3$ | —O—CH(CH$_3$)(CH$_2$)$_3$C$_6$H$_5$ | trans | 2.07 | ~5.6 | |
| H | CH$_3$ | H | H | —O—CH(CH$_3$)(CH$_2$)$_3$C$_6$H$_5$ | cis | 1.33 | | |
| COCH$_3$ | H | H | H | —O—(CH$_2$)$_4$C$_6$H$_5$ | cis | <10 | >10 | |
| COCH$_3$ | CH$_3$ | H | H | —O—(CH$_2$)$_4$C$_6$H$_5$ | trans | ≦56 | | |
| COCH$_3$ | CH$_3$ | H | CH$_3$ | —O—CH(CH$_3$)(CH$_2$)$_3$C$_6$H$_5$ | cis* | 5.3 | >10 | |
| COCH$_3$ | CH$_3$ | H | CH$_3$ | —O—(CH$_2$)$_4$C$_6$H$_5$ | trans | | >10 | |
| COCH$_3$ | CH$_3$ | H | H | —O—(CH$_2$)$_4$C$_6$H$_5$ | | >56 | >10 | |
| COCH$_3$ | H | CH$_3$ | H | —OCH(CH$_3$)(CH$_2$)$_3$C$_6$H$_5$ | trans | 2.31 | | |
| COCH$_3$ | H | CH$_3$ | H | —OCH(CH$_3$)(CH$_2$)$_3$C$_6$H$_5$ | cis | 5.59 | | |
| COCH$_3$ | n-C$_3$H$_7$ | H | H | —O—CH(CH$_3$)(CH$_2$)$_3$C$_6$H$_5$ | trans* | 0.38 | 2.37 | 83 @ 10 |
| COCH$_3$ | n-C$_3$H$_7$ | H | H | —O—CH(CH$_3$)(CH$_2$)$_3$C$_6$H$_5$ | cis* | 0.16 | 1.76 | |
| COCH$_3$ | CH$_3$ | H | H | —O—CH(CH$_3$)(CH$_2$)$_3$C$_6$H$_5$ | cis*$^{(a)}$ | 25 @ 10 | | |
| COCH$_3$ | CH$_3$ | H | H | —O—CH(CH$_3$)(CH$_2$)$_3$C$_6$H$_5$ | cis*$^{(b)}$ | 0.62 | | |
| COCH$_3$ | CH$_3$ | H | H | —O—CH(CH$_3$)(CH$_2$)$_3$C$_6$H$_5$ | trans*$^{(a)}$ | 2.11 | | |
| COCH$_3$ | CH$_3$ | H | H | —O—CH(CH$_3$)(CH$_2$)$_3$C$_6$H$_5$ | trans*$^{(b)}$ | 7.28 | | |
| COCH$_3$ | C$_2$H$_5$ | H | H | —O—CH(CH$_3$)(CH$_2$)$_3$C$_6$H$_5$ | cis | 0.17 | 0.78 | 1.62 |
| COCH$_3$ | C$_6$H$_{13}$ | H | H | —O—CH(CH$_3$)(CH$_2$)$_3$C$_6$H$_5$ | trans | 35 @ 10 | | |
| COCH$_3$ | C$_2$H$_5$ | H | H | —O—CH(CH$_3$)(CH$_2$)$_3$C$_6$H$_5$ | trans* | 1.60 | | |
| COCH$_3$ | C$_6$H$_{13}$ | H | H | —O—CH(CH$_3$)(CH$_2$)$_3$C$_6$H$_5$ | cis | 21 @ 10 | | |
| COCH$_3$ | (CH$_2$)$_2$C$_6$H$_5$ | H | H | —O—CH(CH$_3$)(CH$_2$)$_3$C$_6$H$_5$ | trans | 100 @ 10 | | |
| COCH$_3$ | (CH$_2$)$_2$C$_6$H$_5$ | H | H | —O—CH(CH$_3$)(CH$_2$)$_3$C$_6$H$_5$ | cis | 34 @ 10 | | |
| COCH$_3$ | CH$_3$ | H | H | —O(CH$_2$)$_3$C$_6$H$_5$ | trans | 22 @ 56 | | |
| COCH$_3$ | CH$_3$ | H | H | —O(CH$_2$)$_3$C$_6$H$_5$ | cis | 12 @ 56 | | |
| COCH$_3$ | C$_5$H$_{11}$ | H | H | —O—CH(CH$_3$)(CH$_2$)$_3$C$_6$H$_5$ | trans | 14 @ 10 | | |
| COCH$_3$ | C$_5$H$_{11}$ | H | H | —O—CH(CH$_3$)(CH$_2$)$_3$C$_6$H$_5$ | cis | 14 @ 10 | | |
| COCH$_3$ | C$_4$H$_9$ | H | H | —O—CH(CH$_3$)(CH$_2$)$_3$C$_6$H$_5$ | trans | 4.36 | | |
| COCH$_3$ | C$_4$H$_9$ | H | H | —O—CH(CH$_3$)(CH$_2$)$_3$C$_6$H$_5$ | cis | 16 @ 10 | | |

*hydrochloride salt
$^{(a)}$6S,6aR,9R,10aR
$^{(b)}$6R,6aS,9S,10aS

Their antihypertensive utility is determined by their ability to lower the blood pressure of conscious hypertensive rats and dogs a statistically significant degree when administered orally to said hosts at the above-mentioned dosages.

Their tranquilizer activity is demonstrated by oral administration to rats at doses of from about 0.01 to 50 mg./kg. with subsequent decreases in spontaneous motor activity. The daily dosage range in mammals is from about 0.01 to about 100 mg.

The use of these compounds for the treatment of glaucoma is believed to be due to their ability to reduce intraocular pressure. Their effects on intraocular pressure are determined by tests on dogs. The test drug is instilled into the eye of a dog in the form of a solution or is adminstered systemically at various periods of time after which the eye is anesthetized by instillation of tetracaine hydrochloride, ½%, 2 drops. A few minutes after this local anesthesia, intraocular pressure readings are taken with a Schiotz mechanical tonometer and, after fluorescein dye is administered, with a Holberg hand application tonometer. The test drug is conveniently used in a solution such as the following: test drug (1 mg.), ethanol (0.05 ml.), Tween 80 (polyoxyalkylene derivative of sorbitan mono-oleate, available from Atlas Powder Co., Wilmington Delaware 19899) (50 mg.) and saline (to make 1 ml.), or in a more concentrated solution wherein the ingredients are present in proportions of 10 mg., 0.10 ml. 100 mg. and 1 ml., respectively. For human use, concentrations of drug from 0.1 mg./kg. to 10 mg./kg. are useful.

Their activity as diuretic agents is determined by the procedure of Lipschitz et al., *J. Pharmacol.*, 79, 97 (1943) which utilizes rats as the test animals. The dosage range for this use is the same as that noted above with respect to the use of the herein described compounds as analgesic agents.

This invention also provides pharmaceutical compositions, including unit dosage forms, valuable for the use of the herein described compounds as analgesics and other utilities disclosed herein. The dosage form may be given in single or multiple doses, as previously noted, to achieve the daily dosage effective for a particular utility.

The compounds (drugs) described herein can be formulated for administration in solid or liquid form for oral or parenteral administration. Capsules containing drugs of this invention; i.e.; compounds of formulae I or II are prepared by mixing one part by weight of drug with nine parts of excipient such as starch or milk sugar and then loading the mixture into telescoping gelatin capsules such that each capsule contains 100 parts of the mixture. Tablets containing compounds of formulae I or II are prepared by compounding suitable mixtures of drug and standard ingredients used in preparing tablets, such as starch, binders and lubricants, such that each tablet contains from 0.01 to 100 mg. of drug per tablet.

Suspensions and solutions of these drugs, particularly, those wherein $R_1$ (formulae I and II) is hydroxy, are generally prepared just prior to use in order to avoid problems of stability of the drug (e.g. oxidation) or of suspensions or solution (e.g. precipitation) of the drug up on storage. Compositions suitable for such are generally dry solid compositions which are reconstituted for injectable administration.

EXAMPLE 1

Ethyl dl-3-(3,5-Dimethoxyanilino)butyrate

A mixture of 3,5-dimethoxyaniline (95.7 g., 0.624 mole), ethyl acetoacetate (87.2 ml., 0.670 mole), benzene (535 ml.) and glacial acetic acid (3.3 ml.) is refluxed for 15 hours under an atmosphere of nitrogen and water collected by means of a Dean-Stark trap. The reaction mixture is cooled to room temperature, decolorized with activated charcoal, filtered, and then concentrated under reduced pressure to give the product, ethyl 3-[3,4-dimethoxy)anilino]-2-butenoate, as an oil (168.7 g.).

A mixture of ethyl 3-(3,5-dimethoxyanilino)-2-butenoate (5.0 g., 18.7 mmole) in glacial acetic acid (42 ml.) and platinum oxide (250 mg.) is hydrogenated in a Parr shaker at 50 p.s.i. for 1.5 hours. The reaction mixture is filtered through filter-aid, benzene (50 ml.) added and the solution concentrated under reduced pressure to an oil. The oil is taken up in chloroform, the solution washed successively with saturated sodium bicarbonate solution ($2 \times 50$ ml.) and saturated sodium chloride solution. It is then dried (MgSO$_4$), filtered and concentrated under reduced pressure to give the product as an oil (5.1 g.).

Repetition of the above procedure but using 168.7 g. of ethyl 3-(3,5-dimethoxyanilino)-2-butenoate, glacial acetic acid (320 ml.) and platinum oxide (2.15 g.) gives 160.8 g. of product.

EXAMPLE 2

Ethyl dl-3-(3,5-Dimethoxyaninlino)butyrate

To a solution of 3,5-dimethoxyaniline hydrochloride (370 g., 1.45 mole), reagent grade methanol (4.5 l.) and ethyl acetoacetate (286.3 g., 2.64 mole) in a 12 liter round bottom, 3 neck flask fitted with methanical stirrer and reflux condenser is added sodium cyanoborohydride (54 g., 0.73 mole) in one portion. After the refluxing subsides (10 minutes) the mixture is heated on a steam bath for an additional 20 minutes. To the cooled reaction mixture is added additional sodium cyanoborohydride (5.4 g., 0.07 mole) and ethyl acetoacetate (28.6 g., 0.26 mole) and the mixture refluxed for 30 minutes. This latter process is repeated once more.

The reaction mixture is isolated in portions by pouring ca. 500 ml. onto 1 liter of ice-water/500 ml. methylene chloride, separating the layers and backwashing the aqueous phase with additional methylene chloride (100 ml.). (This process is repeated using 500 ml. portions until the entire reaction mixture is worked up.)

The methylene chloride layers are combined and dried (MgSO$_4$), decolorized with charcoal, filtered and evaporated to yield a yellow colored oil.

The excess ethyl acetoacetate is distilled (at 130° C. oil bath temperature and 1–5 mm. pressure) leaving the crude ethyl 3-(3,5-dimethoxyanilino)butyrate (an amber colored viscous oil): 376 g. (72% yield) which is used without further purification.

It has the following spectral characteristics:

$^1$H NMR (60 MHz) $\delta CDCl_3^{TMS}$ (ppm): 5.82–6.0 (m,3H, aromatic), 4.20 (q,2H, ester methylene), 3.80–4.00(m,2H,-NH and —N—CH—CH$_3$), 3.78 (s, 6H, —OCH$_3$), 2.40–2.55 (m,2H,—CH$_2$COOEt), 1.78 (d,3H,methyl) and 1.29 (t,3H,methyl).

EXAMPLE 3 dl-Ethyl 3-(3,5-Dimethoxyanilino)hexanoate

Following the procedure of Example 2, condensation of 3,5-dimethoxyaniline hydrochloride and ethyl butyrylacetate gives ethyl d,l-3-(3,5-dimethoxyanilino)hexanoate. It is converted to the hydrochloride salt by addition of hydrogen chloride to a methylene chloride solution thereof; m.p. 127°–129.5° C. Recrystallization from cyclohexane/benzene (5:1) gives the analytical sample, m.p. 126°–128.5° C.

Analysis: Calc'd for C$_{16}$H$_{25}$O$_4$N.HCl: C, 57.91; H, 7.90; N, 4.22%. Found: C, 57.89; H, 7.74; N, 4.40%.

m/e-295 (m+)

$^1$H NMR (60 MHz) $\delta_{CDCl_3}^{TMS}$(ppm): 10.76–11.48 (b, variable, 2H, NH$_2$+), 6.77 (d, J=2 Hz, 2H, meta H's), 6.49, 6.45 (d of d, J=2 Hz, 1H, meta H), 4.08 (q, 2H, OCH$_2$), 3.77 (s, 6H, [OCH$_3$]$_2$), ca. 3.5–4.8 (m, 1H, CH—N), 2.90 (t, 2H, CH$_2$—C═O), ca. 1.4–2.2 (m, 4H [CH$_2$]$_2$), 1.21 (t, 3H, O—C—CH$_3$), 0.84 (t, 3H, —C—CH$_3$).

EXAMPLE 4 d,l-Ethyl 3-[(3,5-Dimethoxy-N-ethoxycarbonyl)anilino]butyrate

Method A—

Ethyl chloroformate (71.4 ml. 0.75 mole) is added dropwise over a 45 minute period to a mixture of ethyl 3-(3,5-dimethoxyanilino)butyrate (159.8 g., 0.598 mole), methylene chloride (100 ml.), and pyridine (100 ml., 1.24 moles) at 0° C. under a nitrogen atmosphere. The mixture is stirred for 40 minutes following addition of the ethyl chloroformate and is then poured into a mixture of chloroform (750 ml.) and ice-water (500 ml.). The chloroform layer is separated, washed successively with 10% hydrochloric acid (3×500 ml.), saturated aqueous sodium bicarbonate (1×300 ml.) and saturated aqueous sodium chloride (1×400 ml.) and then dried (MgSO$_4$). It is then decolorized with activated charcoal and concentrated under reduced pressure to an oil (215 g.). The product is used as is.

Method B—

Under a positive nitrogen atmosphere a mixture of ethyl 3-(3,5-dimethoxyanilino)butyrate (376 g., 1.4 mole), methylene chloride (1.4 liters) and anhydrous potassium carbonate (388.8 g., 2.81 mole) is stirred and cooled in an ice bath to 0°→5° C. Ethyl chloroformate (153 g., 1.41 mole) is added in one portion. The mixture is allowed to warm to room temperature over a period of one hour, ethyl chloroformate (153 g., 1.41 mole) is added once more and the mixture is refluxed on a steam bath for one hour. It is then allowed to cool to room temperature and the potassium carbonate removed by filtration. The red colored filtrate is washed successively with water (2×1000 ml.), brine (1×500 ml.), dried (MgSO$_4$), and then decolorized and evaporated under reduced pressure to afford 439 g. of crude product which is used without further purification.

$^1$H NMR (60 MHz) $\delta_{CDCl_3}^{TMS}$ (ppm): 6.2–6.42 (m, 3H, aromatic), 4.65 (sextet, 1H, —N—CH—, CH$_3$), 4.10–4.15 (2 quartets, 4H, ester methylenes), 3.70 (s, 6H, —OCH$_3$), 2.30–2.60 (m, 2H, —CH$_2$COOEt), 1.00–1.40 (m, 9H, 3 methyl).

EXAMPLE 5 d,l-3-[(3,5-Dimethoxy-N-ethoxycarbonyl)anilino]-butyric Acid

Method A—

Ethyl 3-[(3,5-dimethoxy-N-ethoxycarbonyl)anilino]-butyrate (202 g., 0.595 mole), aqueous sodium hydroxide (595 ml. of 1N) and ethanol (595 ml.) are combined and stirred at room temperature overnight. The reaction mixture is concentrated to about 600 ml. volume under reduced pressure, the concentrate diluted with water to 1200 ml. volume and extracted with ethyl acetate (3×750 ml.). The aqueous layer is then acidified with 10% hydrochloric acid to pH 2 and extracted again with ethyl acetate (3×750 ml.). These latter extracts are combined, washed with brine, dried (MgSO$_4$), filtered and concentrated in vacuo to yield the title produce as an oil (163.5 g., 88.2%).

Method B—

A 5 liter 3 neck, round bottom flask equipped with mechanical stirrer and reflux condensor is charged with a solution of ethyl 3-[(3,5-dimethoxy-N-ethoxycarbonyl)anilino]-butyrate (439 g., 1.41 moles) in ethanol (2 liters). Sodium hydroxide (2 liters of 1N) is added and the mixture refluxed on a steam bath for 3 hours. The reaction mixture is poured onto 5 liters of ice-water and extracted in one liter portions with diethyl ether (500 ml./portion). The aqueous layer is cooled by adding ca. one liter of ice and then acidified with concentrated hydrochloric acid (1.75 ml., 2.1 moles). It is extracted in portions of one liter with methylene chloride (250 ml./portion). The methylene chloride layers are combined and dried over magnesium sulfate, decolorized with charcoal and evaporated to dryness to yield a viscous yellow oil. Crystallization from ether/cyclohexane (1:2) affords 224 g. (55.3%) of crystalline product, m.p. 78°–80° C. This material is used without further purifications in the following step.

$^1$H NMR (60 MHz) $\delta_{CDCl_3}^{TMS}$ (ppm): 6.24–6.53 (m, 3H, aromatic), 4.65 (sextet, 1H, —N(-COOC$_2$H$_5$)CH(CH$_3$)CH$_2$COOC$_2$H$_5$), 4.10 (quartet, 2H, ester methylene), 3.78 (s, 6H, —OCH$_3$), 2.40–2.60 (m, 2H, —CH$_2$COOH), 1.18 (t), 1.28 (d, 6H, methyl), 10.8 (bs, variable, 1H, COOH).

MS (mol.ion) m/e-311.

An analytical sample, obtained by recrystallization from ethyl acetate/hexane (1:5), melted at 89°–91° C.

Analysis: Calc'd for C$_{15}$H$_{21}$O$_6$N: C, 57.86; H, 6.80; N, 4.50%. Found: C, 58.08; H, 6.65; N, 4.46%.

EXAMPLE 6 d- and l-3[(3,5-Dimethoxy-4-N-ethoxycarbonyl)anilino]-butyric Acids

A mixture of dl-3-[(3,5-dimethoxy-N-ethoxycarbonyl)anilino]butyric acid (136.6 g., 0.44 mole) and l-ephedrine (72.5 g., 0.44 mole) is dissolved in methylene chloride (500 ml.). The methylene chloride is then removed in vacuo to yield the l-ephedrine salt of dl-3-[(3,5-dimethoxy-N-ethoxycarbonyl)anilino]butyric acid as an oil, $[\alpha]_D^{25} = -20.0$ (c=1.0, CHCl$_3$). Addition of ether (1500 ml.) causes crystallization of a white solid which is separated by filtration and dried (102 g.), m.p. 114°–116° C. Recrystallization from ethyl acetate/hexane (1:1) affords 71.1 g. (34%) of the l-ephedrine salt of l-3-[(3,5-dimethoxy-N-ethoxycarbonyl)anilino]butyric acid; m.p. 126°–127° C.

Analysis: Calc'd for C$_{25}$H$_{36}$O$_7$N$_2$: C, 63.00; H, 7.61; N, 5.88%. Found: C, 62.87; H, 7.64; N, 5.88%.

$[\alpha]_D^{25} = -43.5°$ (c=1.0, CHCl$_3$).

The l-ephedrine salt of the l-isomer is stirred in a mixture of ethyl acetate (1000 ml.) and 10% hydrochloric acid (400 ml.) for ten minutes. The organic phase is separated, washed with 10% hydrochloric acid (2×400 ml.), dried and concentrated under reduced pressure to an oil. Crystallization of the oil from ethyl acetate/hexane (400 ml. of 1:1) affords 34.6 g. of l-3-[(3,5-dimethoxy-N-ethoxycarbonyl)anilino]butyric acid, m.p. 96°–97° C.

Analysis: Calc'd for C$_{15}$H$_{21}$O$_6$N: C, 57.86; H, 6.80; N, 4.50%. Found: C, 57.90; H, 6.66; N, 4.45%.

$[\alpha]_D^{25} = -25.4°$ (c=1.0, CHCl$_3$).

The mother liquor remaining from recrystallization of the l-ephedrine salt of the l-isomer is treated with hydrochloric acid as described above to give crude d-3-[(3,5-dimethoxy-N-ethoxycarbonyl)anilino]butyric acid. Treatment of the crude acid with d-ephedrine affords, after crystallization from ether, the d-ephedrine salt of the d-isomer, m.p. 124°–125° C.

Analysis: Calc'd for C$_{25}$H$_{36}$O$_7$N$_2$: C, 63.00; H, 7.61; N, 5.88%.Found: C, 62.82; H, 7.47; N, 5.97%.

$[\alpha]_D^{25} = +44.0°$ (c=1.0, CHCl$_3$).

The d-ephedrine salt is converted to d-3-[(3,5-dimethoxy-N-ethoxy-carbonyl)anilino]butyric acid in the same manner as described above for conversion of the l-ephedrine salt to the free acid. M.p. 96°–97° C. after recrystallization from ethyl acetate/hexane (3:5).

Analysis: Calc'd for C$_{15}$H$_{21}$O$_6$N: C, 57.86; H, 6.80; N, 4.50%. Found: C, 57.95; H, 6.57; N, 4.35%.

$[\alpha]_D^{25} = +25.3°$ (c=1.0, CHCl$_3$).

EXAMPLE 7

Methyl 3-(3,5-Dimethoxyanilino)propionate

A mixture of 3,5-dimethoxyaniline (114.9 g., 0.75 mole), methyl acrylate (69.73 g., 0.81 mole) and glacial acetic acid (2 ml.) is refluxed for 20 hours. Reflux is disconnected and the reaction mixture is concentrated and then distilled in vacuo, to yield 106.8 g. (73.9%) of the title product, b.p. 174°–179° C. (0.7 mm.).

$^1$H NMR (60 MHz) $\delta_{CDCl_3}^{TMS}$ (ppm): 5.62–5.95 (m, 3H, aromatic), 4.1 (variable, bs, 1H, —NH), 3.74 (s, 6H, —OCH$_3$), 3.68 (s, 3H, COOCH$_3$), 3.41 and 2.59 (two 2H triplets, —NCH$_2$CH$_2$CO$_2$).

Repetition of this procedure but using the appropriate aniline reactant in place of 3,5-dimethoxyaniline affords the following compounds

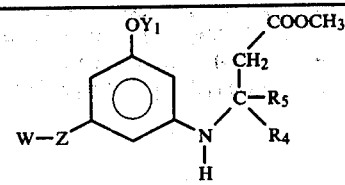

| Y$_1$ | Z—W |
|---|---|
| C$_2$H$_5$ | OC$_2$H$_5$ |
| C$_7$H$_7$ | OC$_7$H$_7$ |
| C$_7$H$_7$ | SCH$_3$ |
| CH$_3$ | SCH$_3$ |
| C$_2$H$_5$ | SCH$_3$ |

EXAMPLE 8

Methyl 3-(3,5-Dimethoxyanilino)alkanoates

The procedure of Example 7 is repeated but using the appropriate ester R$_4$R$_5$C=CH—COOCH$_3$ in place of methyl acrylate and the appropriate protected aniline reactant to give the following compounds.

When R$_5$ is hydrogen, the same products are obtained by the procedure of Examples 1 and 2 but using methyl acetoacetate and methyl propionylacetate in place of ethyl acetoacetate and the appropriate protected aniline reactant.

| Y$_1$ | Z—W | R$_4$ | R$_5$ |
|---|---|---|---|
| CH$_3$ | OCH$_3$ | CH$_3$ | H |
| CH$_3$ | OCH$_3$ | C$_2$H$_5$ | H |
| C$_2$H$_5$ | OC$_2$H$_5$ | CH$_3$ | CH$_3$ |
| CH$_3$ | SCH$_3$ | CH$_3$ | H |
| CH$_3$ | SCH$_3$ | C$_2$H$_5$ | H |
| C$_7$H$_7$ | SCH$_3$ | C$_2$H$_5$ | H |
| C$_2$H$_5$ | OC$_2$H$_5$ | C$_2$H$_5$ | CH$_3$ |
| C$_7$H$_7$ | OC$_7$H$_7$ | CH$_3$ | H |
| C$_7$H$_7$ | OC$_7$H$_7$ | C$_2$H$_5$ | H |
| C$_2$H$_5$ | SCH$_3$ | CH$_3$ | CH$_3$ |
| C$_7$H$_7$ | SCH$_3$ | CH$_3$ | H |
| CH$_3$ | OCH$_3$ | C$_2$H$_5$ | C$_2$H$_5$ |
| CH$_3$ | SCH$_3$ | C$_2$H$_5$ | CH$_3$ |
| CH$_3$ | OCH$_3$ | CH$_3$ | CH$_3$ |
| CH$_3$ | OCH$_3$ | n-C$_3$H$_7$ | H |
| CH$_3$ | OCH$_3$ | n-C$_4$H$_9$ | H |
| CH$_3$ | OCH$_3$ | n-C$_6$H$_{13}$ | H |
| CH$_3$ | SCH$_3$ | n-C$_3$H$_7$ | H |
| CH$_3$ | SCH$_3$ | n-C$_5$H$_{11}$ | CH$_3$ |
| C$_7$H$_7$ | OC$_7$H$_7$ | i-C$_3$H$_7$ | H |
| CH$_3$ | OCH$_3$ | n-C$_4$H$_9$ | CH$_3$ |
| CH$_3$ | OC$_2$H$_5$ | n-C$_6$H$_{13}$ | CH$_3$ |
| CH$_3$ | OCH$_3$ | CH$_2$C$_6$H$_5$ | H |
| CH$_3$ | OCH$_3$ | CH$_2$C$_6$H$_5$ | CH$_3$ |
| CH$_3$ | OCH$_3$ | (CH$_2$)$_4$C$_6$H$_5$ | CH$_3$ |
| CH$_3$ | SCH$_3$ | CH$_2$C$_6$H$_5$ | CH$_3$ |
| CH$_3$ | OCH$_3$ | (CH$_2$)$_3$C$_6$H$_5$ | CH$_3$ |
| CH$_3$ | SCH$_3$ | (CH$_2$)$_2$C$_6$H$_5$ | C$_2$H$_5$ |
| CH$_3$ | SCH$_3$ | CH$_2$C$_6$H$_5$ | H |
| C$_2$H$_5$ | OC$_2$H$_5$ | C$_2$H$_5$ | C$_2$H$_5$ |
| C$_7$H$_7$ | SCH$_3$ | (CH$_2$)$_4$C$_6$H$_5$ | C$_2$H$_5$ |
| C$_7$H$_7$ | OC$_7$H$_7$ | CH$_3$ | CH$_3$ |
| C$_2$H$_5$ | OC$_2$H$_5$ | (CH$_2$)$_2$C$_6$H$_5$ | CH$_3$ |

EXAMPLE 9 d.l-Methyl 3-{[3-hydroxy-5-(5-phenyl-2-pentyl)]anilino}propionate

A mixture of 3-hydroxy-5-(5-phenyl-2-pentyl)-aniline (1.0 g.), methyl acrylate (345 mg.), and acetic acid (0.1 ml.) is heated at 106°–110° C. overnight. The cooled residue is dissolved in 100 ml. ethyl acetate and washed twice with 100 ml. of saturated sodium bicarbonate solution. The organic phase is then dried (MgSO$_4$) and evaporated to a crude residue which is chromatographed on 130 g. of silica gel using benzene-ether (2:1) as the eluant. After elution of less polar impurities, 540 mg. (40%), d,l-methyl 3-{[3-hydroxy-5-(5-phenyl-2-pentyl)]anilino}propionate is collected. It has the following spectral characteristics:

$^1$H NMR (60 MHz) $\delta_{CDCl_3}^{TMS}$ (ppm): 7.14 (s, 5H, aromatic), 5.83–6.13 (m, 3H, aromatic), 3.66 (s, 3H, —COOCH$_3$), 3.37 (t, 2H, —NCH$_2$), 2.16–2.78 (m, 5H, —CH$_2$COO and benzylic), 1.28–1.69 (m, 4H, —(CH$_2$)$_2$—), 1.11 (d, 3H, >—CH$_3$), 4.4–5.2 and 1.28–2.78 (variable, 1H, NH, OH). m/e+341 (m+)

EXAMPLE 10

Methyl 3-[(3,5-Dimethoxy-N-ethoxycarbonyl)anilino]propionate

Ethyl chloroformate (2.0 g., 8.4 mmole) is added dropwise over a 10 minute period to a mixture of methyl 3-(3,5-dimethoxyanilino)propionate (1.0 ml., 10.5 mmole), methylene chloride (5 ml.) and pyridine (5 ml.) at 0° C. under a nitrogen atmosphere. The mixture is stirred at 0° C. for 20 minutes following addition of the ethyl chloroformate and then at room temperature for an additional 20 minutes, and is then poured into a mixture of methylene chloride (75 ml.) and ice-water (50 ml.). The methylene chloride layer is separated, washed successively with 10% hydrochloric acid (2×50 ml.), saturated aqueous sodium bicarbonate (1×30 ml.) and saturated aqueous sodium chloride (1×40 ml.) and dried (MgSO₄). It is then decolorized with activated charcoal and concentrated under reduced pressure to an oil (2.72 g.). The product is used as is.

Similarly, d,l-methyl-3-[3-hydroxy-5-(5-phenyl-2-pentyl)anilino]-propionate is converted to d,l-methyl-3-{[33-hydroxy-5-(5-phenyl-2-pentyl)-N-ethoxycarbonyl-]anilino}propionate and the following compounds are prepared from compounds of Examples 7 and 8 by reaction with the appropriate alkyl chloroformate or other reactant of formula R₆ Br where R₆ is other then hydrogen:

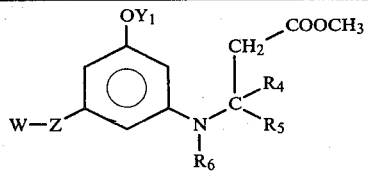

| Y₁ | Z—W | R₄ | R₆ | R₅ |
|---|---|---|---|---|
| CH₃ | OCH₃ | H | COO—n-C₄H₉ | H |
| C₂H₅ | OC₂H₅ | H | CH₂COOC₂H₅ | H |
| C₇H₇ | OC₇H₇ | H | COOCH₃ | H |
| C₇H₇ | SCH₃ | H | COOC₂H₅ | H |
| CH₃ | SCH₃ | H | COO—n-C₃H₇ | H |
| C₂H₅ | SCH₃ | H | (CH₂)₂COOCH₃ | H |
| CH₃ | OCH₃ | CH₃ | CH₂COOC₂H₅ | H |
| CH₃ | OCH₃ | C₂H₅ | COOCH₃ | H |
| C₂H₅ | SCH₃ | CH₃ | COOCH₃ | H |
| CH₃ | SCH₃ | CH₃ | COOC₂H₅ | H |
| C₂H₅ | OC₂H₅ | C₂H₅ | CH₂COO—n-C₄H₉ | H |
| C₇H₇ | OC₂H₅ | C₂H₅ | COOC₂H₅ | H |
| C₇H₇ | OC₇H₇ | CH₃ | COOCH₃ | H |
| C₇H₇ | SCH₃ | C₂H₅ | COOC₂H₅ | H |
| C₇H₇ | OC₇H₇ | C₂H₅ | COOCH₃ | H |
| C₂H₅ | SCH₃ | CH₃ | COO—i-C₃H₇ | H |
| C₇H₇ | SCH₃ | CH₃ | (CH₂)₃COOC₂H₅ | H |
| CH₃ | OCH₃ | H | COOC₇H₇ | H |
| CH₃ | OCH₃ | CH₃ | COOC₇H₇ | H |
| CH₃ | OCH₃ | CH₃ | CH₃ | H |
| CH₃ | OCH₃ | CH₃ | C₂H₅ | H |
| CH₃ | OCH₃ | CH₃ | n-C₄H₉ | H |
| C₂H₅ | SCH₃ | H | i-C₃H₇ | H |
| C₂H₅ | OCH₃ | CH₃ | CH₂C₆H₅ | H |
| CH₃ | OC₂H₅ | CH₃ | (CH₂)₂C₆H₅ | H |
| C₂H₅ | OCH₃ | CH₃ | (CH₂)₄C₆H₅ | H |
| C₂H₅ | SCH₃ | H | CH₃ | H |
| CH₃ | OCH₃ | C₂H₅ | CH₂C₆H₅ | H |
| CH₃ | OCH₃ | C₂H₅ | CH₃ | H |
| CH₃ | SCH₃ | C₂H₅ | (CH₂)₃C₆H₅ | H |
| C₂H₅ | OCH₃ | CH₃ | COOC₂H₅ | CH₃ |
| C₂H₅ | OCH₃ | CH₃ | COOCH₃ | C₂H₅ |
| CH₃ | OCH₃ | C₂H₅ | COOC₂H₅ | C₂H₅ |
| C₂H₅ | SCH₃ | CH₃ | COOC₂H₅ | CH₃ |
| CH₃ | OC₂H₅ | CH₃ | CH₃ | CH₃ |
| CH₃ | SCH₃ | C₂H₅ | COOC₂H₅ | CH₃ |
| CH₃ | OCH₃ | CH₃ | COOCH₂C(CH₃)₃ | CH₃ |
| CH₃ | OCH₃ | CH₃ | CH₂COOCH₃ | H |
| CH₃ | OCH₃ | CH₃ | (CH₂)₄COOCH₃ | H |
| CH₃ | OCH₃ | CH₃ | n-C₆H₁₃ | H |
| CH₃ | OCH₃ | n-C₃H₇ | COOCH₃ | H |
| CH₃ | OCH₃ | n-C₄H₉ | COOCH₃ | H |
| CH₃ | OCH₃ | n-C₆H₁₃ | COOCH₃ | H |
| CH₃ | OC₇H₇ | n-C₄H₉ | CH₃ | CH₃ |
| CH₃ | SCH₃ | n-C₅H₁₁ | CH₂C₆H₅ | CH₃ |
| CH₃ | OC₇H₇ | CH₂C₆H₅ | (CH₂)₄C₆H₅ | CH₃ |
| C₂H₅ | OC₂H₅ | (CH₂)₂C₆H₅ | C₂H₅ | CH₃ |
| C₇H₇ | SCH₃ | (CH₂)₄C₆H₅ | n-C₅H₁₁ | C₂H₅ |
| CH₃ | OCH₃ | (CH₂)₄C₆H₅ | COOC₂H₅ | CH₃ |
| CH₃ | OCH₃ | CH₂C₆H₅ | CH₃ | CH₃ |
| CH₃ | OCH₃ | CH₃ | COCH₃ | CH₃ |
| CH₃ | SCH₃ | (CH₂)₂C₆H₅ | CHO | CH₃ |
| C₇H₇ | OC₇H₇ | CH₃ | COC₅H₁₁ | CH₃ |
| CH₃ | OCH₃ | CH₃ | COCH₂C₆H₅ | CH₃ |
| CH₃ | OCH₃ | CH₃ | CO(CH₂)₃C₆H₅ | H |
| CH₃ | SCH₃ | H | COCH₃ | H |
| CH₃ | SCH₃ | H | n-C₆H₁₃ | H |
| CH₃ | SCH₃ | n-C₃H₇ | n-C₄H₉ | H |
| CH₃ | OCH₃ | CH₂C₆H₅ | COOCH₃ | H |
| C₇H₇ | OC₇H₇ | i-C₃H₇ | COOC₂H₅ | H |
| CH₃ | OC₂H₅ | n-C₆H₁₃ | i-C₃H₇ | CH₃ |
| CH₃ | SCH₃ | CH₂C₆H₅ | COOC₇H₇ | CH₃ |

-continued

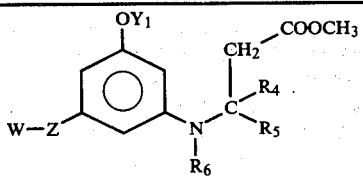

| Y₁ | Z—W | R₄ | R₆ | R₅ |
|---|---|---|---|---|
| CH₃ | OCH₃ | (CH₂)₃C₆H₅ | COCH₂C₆H₅ | CH₃ |
| CH₃ | SCH₃ | CH₂C₆H₅ | COO—n-C₄H₉ | H |
| C₂H₅ | OC₂H₅ | CH₃ | COOC₇H₇ | CH₃ |

EXAMPLE 11

3-[(3,5-Dimethoxy-N-ethoxycarbonyl)anilino]-propionic Acid

Methyl 3-[(3,5-dimethoxy-N-ethoxycarbonyl)anilino]propionate (2.72 g., 8.36 mmoles), aqueous sodium hydroxide (8.4 ml. of 1N) and ethanol (8.4 ml.) are combined and stirred overnight under nitrogen at room temperature. The reaction mixture is then concentrated under reduced pressure to half-volume, diluted with water (35 ml.) and then extracted with ethyl acetate. The aqueous phase is acidified to pH 2 with 10% hydrochloric acid and extracted with methylene chloride (3×50 ml.). The combined extracts are washed with brine, dried (MgSO₄) and concentrated to give the product as an oil (2.47 g.) which is used as is.

In like manner, the remaining compounds of Example 10 are hydrolyzed to their corresponding alkanoic acids having the formula

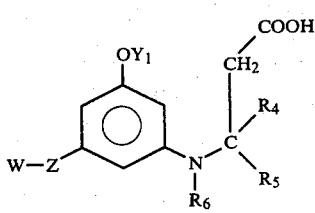

EXAMPLE 12

1-Carbethoxy-5,7-dimethoxy-4-oxo-1,2,3,4-tetrahydroquinoline

A mixture of 3-[(3,5-dimethoxy-N-ethoxycarbonyl)anilino]propionic acid (1.10 g., 3.7 mmole) and polyphosphoric acid (4 g.) is heated at 65° C. for 45 minutes under an atmosphere of nitrogen and is then cooled to 0° C. It is then taken up in a mixture of methylene chloride-water (200 ml. of 1:1). The organic layer is separated and the aqueous phase extracted again with methylene chloride (2×100 ml.). The combined extracts are washed with saturated sodium bicarbonate (3×100 ml.), brine (1×100 ml.) and then dried (MgSO₄). Concentration of the dried extract gives the product as an oil which crystallizes from benzene. Yield=645 mg., m.p. 109°-111° C.

Analysis: Calc'd for $C_{14}H_{17}O_5N$: C, 60.21; H, 6.14; N, 5.02%. Found: C, 60.11; H, 6.14; N, 4.80%.

EXAMPLE 13

5,7-Dihydroxy-4-oxo-1,2,3,4-tetrahydroquinoline

A mixture of glacial acetic acid (60 ml.), 48% hydrobromic acid (60 ml.) and 1-carbethoxy-5,7-dimethoxy-4-oxo-1,2,3,4-tetrahydroquinoline (4.0 g., 14.3 mmole) is refluxed overnight and is then concentrated in vacuo to a dark oil. The oil is dissolved in water (50 ml.) and the aqueous solution neutralized to pH 6-7 with 1N sodium hydroxide. A saturated solution of salt water (50 ml.) is added and the resulting mixture extracted with ethyl acetate (3×150 ml.). The extracts are combined, dried (MgSO₄) and concentrated under reduced pressure to an oil. The oil is taken up in benzene-ethyl acetate (1:1) and the solution charged to a silica gel column. The column is eluted with a volume of benzene equal to the volume of the column and then with benzene-ethyl acetate (250 ml. of 4:1) and benzene-ethyl acetate (250 ml. of 1:1). Fractions (75 ml.) are collected. Fractions 4-9 are combined and evaporated under reduced pressure. The oily residue is crystallized from ethanol-hexane (1:10). Yield=1.86 g., m.p. 166°-169° C.

Further recrystallization raises the melting point to 171°-172.5° C.

m/e+179 (m+)

Analysis: Calc'd for $C_9H_9O_3N$: C, 60.33; H, 5.06; N, 7.82%. Found: C, 60.25; H, 4.94; N, 7.55%.

By means of the procedure of Example 12 and this procedure, 3-{]3-hydroxy-5-(5-phenyl-2-pentyl)-N-ethoxycarbonyl]anilino}propionic acid is transformed to 5-hydroxy-7-(5-phenyl-2-pentyl)-4-oxo-1,2,3,4-tetrahydroquinoline, and the following compounds are prepared from compounds of Example 11:

| R₆ | R₄ | X—H | R₅ |
|---|---|---|---|
| H | C₂H₅ | OH | H |
| H | H | SH | H |
| H | CH₃ | SH | H |
| H | C₂H₅ | SH | H |
| CH₃ | H | OH | H |
| CH₃ | CH₃ | OH | H |
| C₂H₅ | CH₃ | OH | H |
| n-C₄H₉ | CH₃ | OH | H |
| i-C₃H₇ | H | SH | H |
| CH₂C₆H₅ | CH₃ | OH | H |
| (CH₂)₂C₆H₅ | CH₃ | OH | H |
| (CH₂)₄C₆H₅ | CH₃ | OH | H |
| CH₃ | H | SH | H |
| CH₃ | C₂H₅ | OH | H |
| CH₂C₆H₅ | CH₃ | SH | H |
| (CH₂)₃C₆H₅ | C₂H₅ | SH | H |
| C₂H₅ | H | OH | H |
| CH₃ | CH₃ | SH | H |
| H | CH₃ | OH | CH₃ |
| H | C₂H₅ | OH | C₂H₅ |

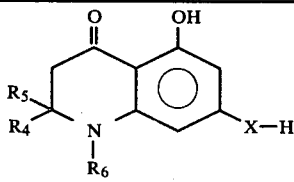

| R6 | R4 | X—H | R5 |
|---|---|---|---|
| H | CH3 | OH | C2H5 |
| n-C6H13 | CH3 | OH | H |
| H | CH3 | SH | CH3 |
| H | C2H5 | SH | C2H5 |
| CH2COOH | H | OH | H |
| CH2COOH | C2H5 | OH | H |
| CH2COOH | CH3 | OH | H |
| (CH2)2COOH | H | SH | H |
| (CH2)3COOH | CH3 | SH | H |
| (CH2)4COOH | CH3 | OH | H |
| H | n-C3H7 | OH | H |
| H | n-C4H9 | SH | H |
| H | n-C6H13 | OH | H |
| H | CH3 | OH | CH3 |
| H | n-C4H9 | OH | CH3 |
| H | n-C4H9 | OH | C2H5 |
| H | n-C6H13 | OH | CH3 |
| H | CH2C6H5 | OH | CH3 |
| H | (CH2)2C6H5 | OH | CH3 |
| H | (CH2)4C6H5 | OH | CH3 |
| H | CH2C6H5 | SH | CH3 |
| H | (CH2)3C6H5 | SH | C2H5 |
| CH3 | CH3 | OH | CH3 |
| n-C3H7 | CH3 | OH | CH3 |
| n-C6H13 | CH3 | OH | CH3 |
| n-C4H9 | CH2C6H5 | OH | CH3 |
| CH3 | n-C4H9 | OH | CH3 |
| CH2C6H5 | CH3 | OH | CH3 |
| (CH2)4C6H5 | CH3 | OH | CH3 |
| CH2C6H5 | (CH2)3C6H5 | OH | CH3 |
| CH2COOH | CH3 | OH | CH3 |
| (CH2)2COOH | CH3 | OH | CH3 |
| (CH2)4COOH | C2H5 | OH | CH3 |
| CH3 | CH3 | OH | CH3 |
| CH2COOH | C2H5 | OH | CH3 |
| CH2C6H5 | CH3 | SH | CH3 |
| (CH2)3C6H5 | CH3 | SH | CH3 |
| CH3 | CH3 | SH | CH3 |
| CH3 | CH2C6H5 | SH | CH3 |
| i-C3H7 | n-C4H9 | SH | C2H5 |
| CH2COOH | (CH2)2C6H5 | SH | C2H5 |
| n-C5H11 | CH3 | SH | CH3 |
| (CH2)4COOH | CH3 | SH | CH3 |
| CH2C6H5 | (CH2)3C6H5 | SH | CH3 |
| H | n-C6H13 | SH | CH3 |
| CH2C6H5 | C2H5 | OH | H |
| n-C4H9 | C2H5 | OH | H |
| CH2C6H5 | H | OH | H |
| (CH2)2COOH | CH3 | SH | H |
| (CH2)4COOH | H | OH | H |
| H | CH2C6H5 | SH | H |
| i-C3H7 | CH3 | SH | CH3 |
| (CH2)3C6H5 | CH3 | SH | CH3 |

EXAMPLE 14 d,l-1-Carbethoxy-5,7-dimethoxy-2-methyl-4-oxo-1,2,3,4-tetrahydroquinoline

A solution of 3-[(3,5-dimethoxy-N-ethoxycarbonyl)anilino]butyric acid (4.0 g., 12.8 mmole) in chloroform (2 ml.) is added dropwise with stirring to polyphosphoric acid (5.0 g.) heated to 60° C. on a steam bath. The reaction mixture is held at 60°–65° C. for two hours and is then poured into a mixture of ice (100 g.) and ethyl acetate (100 ml.). The aqueous layer is further extracted with ethyl acetate (2×100 ml.) and the combined organic extracts washed successively with saturated sodium bicarbonate solution (3×100 ml.), brine (1×100 ml.), and then dried over anhydrous magnesium sulfate. Concentration of the dried extract under reduced pressure gives 2.6 g. of crude product.

Purification is accomplished by column chromatography of a benzene solution of the crude product (2.5 g.) on silica gel ( 95 g.). The column is eluted with a volume of benzene equal to one-half the volume of the column, followed by benzene/ethyl acetate (1:1). Fractions (40 ml.) are collected. Fractions 9–18 are combined and evaporated in vacuo to give 1.55 g. of product which is purified further by recrystallization from petroleum ether-1.33 g., m.p. 92.5°–94° C.

Recrystallization of this product from hot ethyl acetate/hexane (1:1) affords an analytical sample; m.p. 94°–95° C.

Analysis: Calc'd for $C_{15}H_{19}O_5N$: C, 61.42; H, 6.53; N, 4.78%. Found: C, 61.54; H, 6.55; N, 4.94%.

m/e+293 (m+)

IR (KBr)+5.85, 5.95μ

EXAMPLE 15 d,l-5,7-Dihydroxy-2-methyl-4-oxo-1,2,3,4-tetrahydroquinoline

Method A—

A mixture of glacial acetic acid (240 ml.), 48% hydrobromic acid (240 ml.) and 1-carbethoxy-5,7-dimethoxy-2-methyl-4-oxo-1,2,3,4-tetrahydroquinoline (16.0 g., 55 mmole) is refluxed overnight and is then concentrated in vacuo to a dark oil. The oil is dissolved in water (200 ml.) and the aqueous solution neutralized to pH 6–7 with 1N sodium hydroxide. A saturated solution of salt water (200 ml.) is added and the resulting mixture extracted with ethyl acetate (3×500 ml.). The extracts are combined, dried (MgSO4) and concentrated under reduced pressure to a dark oil (12.8 g.). Hexane-ethyl acetate (10:1) is added to the oil and the resulting crystals recovered by filtration (3.8 g.); m.p. 158°–165° C. Trituration of the crystals in ethyl acetate gives 1.65 g. of product; m.p. 165°–168° C.

Additional material separates from the mother liquors on standing (2.9 g.); m.p. 168°–170° C. Column chromatography of the filtrate on silica gel using benzene-ether (1:1) as solvent gives an additional 4.6 g. of product, m.p. 167°–169° C.

Further purification is achieved by recrystallizing the product from ethyl acetate; m.p. 173°–174° C.

Analysis: Calc'd for $C_{10}H_{11}O_3N$: C, 62.16; H, 5.74; N, 7.25%. Found: C, 62.00; H, 5.83; N, 7.14%.

m/e+193 (m+)

Method B—

A mixture of d,l-3-[(3,5-dimethoxy-N-ethoxycarbonyl)anilino]butyric acid (100 g., 0.32 mole) and 48% hydrobromic acid (500 ml.)/glacial acetic acid (300 ml.) is heated in an oil bath at 110° C. for 2 hours. The oil-bath temperature is then increased to 145° C. and heating is continued for an additional 2 hours. During this last heating period an azeotropic mixture distills (boiling point 42°→110° C., ~200–300 ml.) and the deep-red homogeneous solution is allowed to cool to room temperature. The mixture is poured onto icewater (3 liters) and ether (2 liters), the layers are separated and the aqueous solution is washed with ether (2×1000 ml.).

The ether layers are combined and washed successively with water (2×1000 ml.), brine (1×500 ml.), saturated NaHCO$_3$ solution (4×250 ml.) and brine (1×500 ml.) and then dried (MgSO$_4$). Decolorization with charcoal and evaporation of the ether affords a yellow foam which is crystallized from ca. 300 ml. methylene chloride to give 31.3 g. (50.4%) of pure 5,7-dihydroxy-2-methyl-4-oxo-1,2,3,4-tetrahydroquinoline. Additional product can be isolated from the mother liquor by silica gel chromatography.

$^1$H NMR (60 MHz) $\delta^{TMS}$ (100 mg. sample/0.3 ml. CDCl$_3$/0.2 ml. CD$_3$SOCD$_3$) (ppm): 12.40 (s,1H, C$_5$-OH), 5.72 (d,2H,meta H), 5.38–5.60(bs,1H,C$_7$—OH), 3.50–4.00(m,1H,C2H), 2.38–2.60(m,2H,C$_3$-H$_2$), 1.12(d,3H,methyl).

m/e+193 (m+)

Analysis: Calc'd for C$_{10}$H$_{11}$O$_3$N: C, 62.16; H, 5.74; N, 7.25%. Found: C, 62.01; H, 5.85; N, 7.02%.

Similarly, methyl d,l-3-{[3-hydroxy-5-(5-phenyl-2-pentyl)]anilino}-propionate is converted to d,l-5-hydroxy-7-(5-phenyl-2-pentyl)-4oxo-1,2,3,4-tetrahydroquinoline which is purified by column chromatography using silica gel and benzene/ether (5:1) as eluant.

m/e+309 (m+)

$^1$H NMR (60 MHz) $\delta_{CDCl_3}^{TMS}$ (ppm): 12.22 (s, 1H, 5OH), 7.14 (s, 5H, C$_6$H$_5$), 6.04 (d, J−2.5Hz, 1H meta H), 5.87 (d, J=2.5Hz, 1H meta H), 4.19–4.60 (b, 1H, NH), 3.48 (t, 2H, CH$_2$N), 2.18–2.89 (m, 5H, ArCH, ArCH$_2$, CH$_2$—C=O), 1.38–1.86 (m, 4H, -[CH$_2$]$_2$-), 1.13 (d, 3H, CH$_3$).

and ethyl d,l-3-(3,5-dimethoxyanilino)hexanoate hydrochloride is converted to d,l-5,7-dihydroxy-2-propyl-4-oxo-1,2,3,4-tetrahydroquinoline; m.p. 117°–119° C. (from methylene chloride).

m/e+221 (m+), 135 (base peak, m+-propyl).

and l-3-[(3,5-dimethoxy-(N-ethoxy carbonyl)anilino]-butyric acid is converted to d-5,7-dihydroxy-2-methyl-4-oxo-1,2,3,4-tetrahydroquinoline, m.p. 167°–168° C.

$[\alpha]_D^{25}$ = +167.8° (c=1.0, CH$_3$OH).

m/e+193 (m+)

Analysis: Calc'd for C$_{10}$H$_{11}$O$_3$N: C, 62.16; H, 5.74; N, 7.25%. Found: C, 61.87; H, 5.62; N, 6.96%.

and d-3-[3,5-dimethoxy-N-ethoxycarbonyl)anilino]-butyric acid is converted to 1-5,7-dihydroxy-2-methyl-4-oxo-1,2,3,4-tetrahydroquinoline; m.p. 166°–168° C.

$[\alpha]_D^{25}$ = −168.5° (c=1.0, CH$_3$OH).

m/e+193 (m+)

Analysis: Calc'd for C$_{10}$H$_{11}$O$_3$N: C, 62.16; H, 5.74; N, 7.25%.
Found: C, 61.82; H, 5.83; N, 7.22%.

EXAMPLE 16 d,l-5,7-Dihydroxy-2-methyl-4-oxo-1,2,3,4-tetrahydroquinoline

A mixture of 3,5-dimethoxyaniline (230 g., 1.5 moles), methyl crotonate (150 g., 1.5 moles) and glacial acetic acid (90 g., 1.5 moles) is heated at reflux for 6 hours. Additional glacial acetic acid (90 g., 1.5 moles) is added and the mixture refluxed overnight. Hydrobromic acid (1000 ml. of 48% solution) and glacial acetic acid (850 ml.) are added to the reaction mixture which is heated at reflux for 4.5 hours. The title product is isolated and purified according to the procedure of Example 13. Yield=36 g., m.p. 166°–170° C.

Repetition of this procedure but replacing methyl crotonate with methyl acrylate, methyl 3-ethyl acrylate or methyl 3,3-dimethylacrylate affords 5,7-dihydroxy-4-oxo-1,2,3,4-tetrahydroquinoline, 5,7-dihydroxy-2-ethyl-4-oxo-1,2,3,4-tetrahydroquinoline, and 5,7-dihydroxy-2,2-dimethyl-4-oxo-1,2,3,4-tetrahydroquinoline, respectively.

EXAMPLE 17 dl-5,7-Dihydroxy-2-methyl-4-oxo-1,2,3,4-tetrahydroquinoline

A mixture of 3,5-dimethoxyaniline (4.6 g., 0.03 mole), crotonic acid (2.54 g., 0.03 mole) and pyridine hydrochloride (3.0 g., 1.26 moles) is heated at 185°–200° C. for 45 minutes. The cooled reaction mixture is suspended in water (500 ml.) (pH∼3) and the pH adjusted to 7 and the resultant mixture stirred for 10 minutes. The organic layer is separated, dried (MgSO$_4$) and concentrated to 3.2 g. of a yellow oil.

A mixture of glacial acetic acid (110 ml.), 48% hydrobromic acid (110 ml.) and the yellow oil is refluxed for one hour and is then concentrated in vacuo to a dark oil. The oil is dissolved in water and the aqueous solution neutralized to pH 6–7 with 1N sodium hydroxide. A saturated solution of salt water is added and the resulting mixture extracted with ethyl acetate. The extracts are combined, dried (MgSO$_4$) and concentrated under reduced pressure to a dark oil (2.8 g.). Column chromatography of the crude residue on silica gel using benzene-ether (4:1) as eluant gives an additional 510 mg. of product, m.p. 168°–170° C.

Further purification is achieved by recrystallizing the product from ethyl acetate; m.p. 173°–174° C.

Analysis: Calc'd for C$_{10}$H$_{11}$O$_3$N: C, 62.16; H, 5.74; N, 7.25%. Found: C, 62.00; H, 5.83; N, 7.14%.

m/e+193 (m+), 178 (m+-methyl, base peak).

In a similar manner, 3,3-dimethyl acrylic acid and 3,5-dimethoxyaniline gives after purification by silica gel chromatography (benzene/ether 1:1 as eluant) 5,7-dihydroxy-2,2-dimethyl-4-oxo-1,2,3,4-tetrahydroquinoline as a yellow oil.

Analysis (MS)

Parent peak (m+)

Calc'd for C$_{11}$H$_{13}$O$_3$N: 207.0895. Found: 207.0895.

Base peak (m+-15)

Calc'd for C$_{10}$H$_{10}$O$_3$N: 192.0661. Found: 192.0655.

Similarly, styryl acetic acid and 3,5-dimethoxyaniline are condensed to yield dl-5,7-dihydroxy-2-benzyl-4-oxo-1,2,3,4-tetrahydroquinoline as an oil after purification using benzene/ether (3:1) as eluant.

m/e=269 (m+) and 178 (m+-benzyl, base peak)

NMR (CDCl$_3$) $\delta$ (ppm): 8.76 (s, 1H, 5-O<u>H</u>), 7.18-7.6 (m, 5H, C$_6$<u>H$_5$</u>), 5.84 (d, J=3Hz, 1H) and 5.62 (d, J=3Hz, 1H) for the meta coupled aromatics, and 2.14–4.82 (4m, 7H), for the remaining protons (7—O<u>H</u>, C<u>H</u>—N, C<u>H$_2$</u>—C=O, —C<u>H$_2$</u>—C$_6$H$_5$ and N—<u>H</u>).

EXAMPLE 18

Following the procedures of Examples 9–15, the compounds tabulated below are prepared from appropriate 3-hydroxy-5-(Z-W)anilines and appropriate esters of the formula R$_4$R$_5$C=CH—COOCH$_3$ wherein each of R$_4$,R$_5$ is hydrogen, methyl or ethyl.

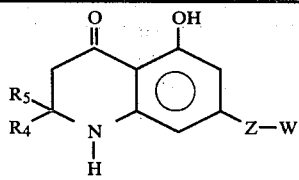

| R5 | R4 | Z | W |
|---|---|---|---|
| H | H | CH(CH3)(CH2)3 | C6H5 |
| H | CH3 | CH(CH3)(CH2)3 | C6H5 |
| H | C2H5 | CH(CH3)(CH2)3 | C6H5 |
| H | CH3 | CH(CH3)(CH2)4 | C6H5 |
| H | H | CH(CH3)(CH2)3 | C6H5 |
| H | H | (CH2)3 | C6H5 |
| H | H | (CH2)4 | C6H5 |
| H | C2H5 | (CH2)4 | C6H5 |
| H | H | (CH2)2CH(C2H5) | C6H5 |
| H | CH3 | CH(C2H5)(CH2)3 | C6H5 |
| H | H | C(CH3)2 | C6H5 |
| H | CH3 | C(CH3)2(CH3)3 | C6H5 |
| H | H | (CH2)6 | C6H5 |
| H | CH3 | (CH2)8 | C6H5 |
| H | H | CH(CH3)(CH2)7 | C6H5 |
| H | H | CH2 | C6H5 |
| H | H | CH(CH3)(CH2)3 | 4-FC6H4 |
| H | CH3 | CH(CH3)(CH2)3 | 4-FC6H4 |
| H | H | CH(CH3)CH2 | 4-FC6H4 |
| H | C2H5 | CH(CH3)CH2 | 4-FC6H4 |
| H | C2H5 | CH(CH3)(CH2)2 | 4-ClC6H4 |
| H | H | CH(CH3)(CH2)2CH(CH3) | C6H5 |
| H | CH3 | CH2 | C6H5 |
| H | H | (CH2)3 | C5H9 |
| CH3 | CH3 | CH(CH3)(CH2)3 | C6H5 |
| H | CH3 | CH(CH3)CH2 | C5H9 |
| H | H | CH(CH3)(CH2)2 | C5H9 |
| H | H | CH(CH3)(CH2)4 | C5H9 |
| H | H | CH(CH3)CH2 | C3H5 |
| H | H | CH(CH3)CH(CH3) | C6H11 |
| H | C2H5 | CH(CH3)CH(CH3) | C6H11 |
| H | H | CH(CH3)(CH2)5 | C6H11 |
| H | CH3 | CH(CH3)(CH2)5 | C6H11 |
| H | H | (CH2)4 | C3H5 |
| H | H | (CH2)8 | C6H11 |
| H | C2H5 | (CH2)8 | C6H11 |
| H | H | (CH2)3CH(CH3) | C6H11 |
| H | CH3 | CH(CH3)(CH2)3 | C6H11 |
| H | H | CH(CH3)(CH2)2CH(CH3) | C6H11 |
| H | CH3 | CH(CH3)CH(CH3)CH2 | C6H11 |
| H | H | (CH2)3 | 2-pyridyl |
| H | H | (CH2)3 | 4-pyridyl |
| H | H | (CH2)4 | 2-pyridyl |
| H | CH3 | (CH2)4 | 4-pyridyl |
| H | C2H5 | (CH2)4 | 3-pyridyl |
| H | CH3 | CH2CH(CH3)CH2 | 4-pyridyl |
| H | C2H5 | CH(CH3)(CH2)2 | 3-pyridyl |
| H | CH3 | CH(CH3)CH(C2H5)CH2 | 4-pyridyl |
| H | H | CH(C2H5)(CH2)3 | 3-pyridyl |
| H | H | CH2CH(C2H5)CH2 | 3-pyridyl |
| H | H | CH(CH3)(CH2)2 | 4-piperidyl |
| H | CH3 | CH(C2H5)(CH2)2 | 2-piperidyl |
| H | CH3 | CH(CH3)(CH2)2CH(CH3) | 4-piperidyl |
| H | CH3 | CH(CH3)(CH2)2 | C7H13 |
| H | H | CH(CH3)(CH2)2 | C7H13 |
| H | CH3 | CH(CH3)CH2—O—(CH2)2 | C6H5 |
| H | H | (CH2)4 | CH3 |
| H | CH3 | CH(CH3)CH(CH3)(CH2)5 | H |
| H | H | CH(CH3)CH(CH3)(CH2)5 | H |
| H | H | CH2 | H |
| H | CH3 | CH2 | CH3 |
| H | H | (CH2)3 | CH3 |
| H | H | (CH2)6 | CH3 |
| H | CH3 | (CH2)6 | CH3 |
| H | H | CH(CH3) | CH3 |
| H | CH3 | (CH2)3 | H |
| H | H | CH(CH3) | C6H11 |
| H | C2H5 | CH(CH3)(CH2)4 | CH3 |
| H | H | (CH2)3—O— | C6H5 |
| H | CH3 | (CH2)3—O— | 4-FC6H4 |
| H | CH3 | (CH2)3—O— | C6H11 |
| H | C2H5 | (CH2)3—O— | C4H7 |

-continued

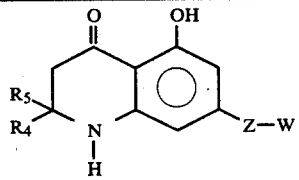

| R$_5$ | R$_4$ | Z | W |
|---|---|---|---|
| H | H | (CH$_2$)$_3$—O— | CH$_3$ |
| H | CH$_3$ | (CH$_2$)$_3$—O— | 4-(4-FC$_6$H$_4$)C$_6$H$_{10}$ |
| H | C$_2$H$_5$ | (CH$_2$)$_3$—O—(CH$_2$)$_2$ | 4-ClC$_6$H$_4$ |
| H | H | (CH$_2$)$_3$—O—(CH$_2$)$_2$ | C$_6$H$_5$ |
| H | CH$_3$ | (CH$_2$)$_3$—O—CH(CH$_3$) | 4-piperidyl |
| H | CH$_3$ | (CH$_2$)$_3$—O—CH(CH$_3$)(CH$_2$)$_2$ | C$_6$H$_5$ |
| H | H | (CH$_2$)$_3$—O—CH(CH$_3$)(CH$_2$)$_2$ | CH$_3$ |
| H | H | CH(CH$_3$)(CH$_2$)$_2$—O— | C$_6$H$_5$ |
| H | CH$_3$ | CH(CH$_3$)(CH$_2$)$_2$—O—CH$_2$ | CH$_3$ |
| H | CH$_3$ | CH(CH$_3$)(CH$_2$)$_2$—O—(CH$_2$)$_4$ | C$_6$H$_5$ |
| H | CH$_3$ | CH(CH$_3$)(CH$_2$)$_2$—O—CH(CH$_3$) | C$_7$H$_{13}$ |
| H | H | CH(CH$_3$)(CH$_2$)$_2$—O—CH$_2$CH—(C$_2$H$_5$) | CH$_3$ |
| H | CH$_3$ | (CH$_2$)$_4$—O— | C$_6$H$_5$ |
| H | H | (CH$_2$)$_4$—O—CH(CH$_3$)CH$_2$ | 3-piperidyl |
| H | C$_2$H$_5$ | (CH$_2$)$_4$—O—(CH$_2$)$_5$— | 4-pyridyl |
| H | C$_2$H$_5$ | (CH$_2$)$_4$—O—CH$_2$ | 4-FC$_6$H$_4$ |
| H | H | CH(CH$_3$)(CH$_2$)$_3$—O— | 2-(4-FC$_6$H$_5$)C$_2$H$_8$ |
| H | CH$_3$ | CH(CH$_3$)(CH$_2$)$_3$—O—(CH$_2$)$_2$ | C$_6$H$_5$ |
| H | C$_2$H$_5$ | CH(CH$_3$)(CH$_2$)$_3$—O—(CH$_2$)$_2$ | CH$_3$ |
| H | H | CH(C$_2$H$_5$)(CH$_2$)$_2$—O—(CH$_2$)$_4$ | C$_6$H$_5$ |
| H | CH$_3$ | CH(C$_2$H$_5$)(CH$_2$)$_2$—O—CH(CH$_3$) | 4-piperidyl |
| H | H | CH(C$_2$H$_5$)(CH$_2$)$_2$—O—(CH$_2$)$_2$—CH(CH$_3$) | C$_7$H$_{13}$ |
| H | CH$_3$ | CH(CH$_3$)—O—CH$_2$ | C$_5$H$_9$ |
| H | CH$_3$ | CH(C$_2$H$_5$)(CH$_2$)$_2$—O— | C$_3$H$_5$ |
| H | H | CH(C$_2$H$_5$)(CH$_2$)$_2$—O— | 2-(4-FC$_6$H$_{11}$)C$_7$H$_{12}$ |
| H | H | (CH$_2$)$_3$—S— | C$_6$H$_5$ |
| H | C$_2$H$_5$ | (CH$_2$)$_3$—S—CH$_2$ | 4-FC$_6$H$_4$ |
| H | CH$_3$ | (CH$_2$)$_3$—S— | C$_5$H$_9$ |
| H | C$_2$H$_5$ | (CH$_2$)$_3$—S—(CH$_2$)$_2$ | CH$_3$ |
| H | H | (CH$_2$)$_3$—S—(CH$_2$)$_4$ | C$_6$H$_5$ |
| H | CH$_3$ | CH(CH$_3$)(CH$_2$)$_2$—S— | 4-piperidyl |
| H | CH$_3$ | CH(CH$_3$)(CH$_2$)$_2$—S— | 4-(C$_6$H$_5$)C$_6$H$_{10}$ |
| H | CH$_3$ | CH(CH$_3$)(CH$_2$)$_2$—S—(CH$_2$)$_2$ | 4-pyridyl |
| H | CH$_3$ | CH(CH$_3$)(CH$_2$)$_2$—S—(CH$_2$)$_4$ | C$_6$H$_5$ |
| H | C$_2$H$_5$ | CH(C$_2$H$_5$)(CH$_2$)$_2$—S— | C$_6$H$_{11}$ |
| H | CH$_3$ | CH(C$_2$H$_5$)(CH$_2$)$_2$—S—(CH$_2$)$_2$—CH(CH$_3$) | CH$_3$ |
| H | H | CH(C$_2$H$_5$)(CH$_2$)$_2$—S—CH(CH$_3$) | 4-ClC$_6$H$_4$ |
| H | H | CH(CH$_3$)(CH$_2$)$_3$—S—(CH$_2$)$_4$ | 4-FC$_6$H$_4$ |
| H | CH$_3$ | CH(CH$_3$)(CH$_2$)$_3$—S—(CH$_2$)$_4$ | 4-pyridyl |
| H | H | CH(CH$_3$)CH$_2$—O—(CH$_2$)$_6$ | CH$_3$ |
| H | CH$_3$ | CH(CH$_3$)CH$_2$—O—(CH$_2$)$_6$ | C$_6$H$_5$ |
| H | H | CH(CH$_3$)CH$_2$—O—(CH$_2$)$_4$ | CH$_3$ |
| H | H | CH(CH$_3$)CH$_2$—O—CH(CH$_3$)CH$_2$ | C$_6$H$_5$ |
| H | CH$_3$ | CH(CH$_3$)CH$_2$—O—CH(CH$_3$)CH$_2$ | C$_6$H$_5$ |
| H | C$_2$H$_5$ | CH(CH$_3$)CH$_2$—O—CH(CH$_3$)CH$_2$ | C$_6$H$_5$ |
| H | CH$_3$ | CH(CH$_3$)CH$_2$—O—CH$_2$ | 4-FC$_6$H$_4$ |
| H | CH$_3$ | CH(CH$_3$)CH$_2$—O—(CH$_2$)$_2$ | 4-pyridyl |
| H | H | CH(CH$_3$)CH$_2$—O—CH(CH$_3$) | CH$_3$ |
| H | H | CH$_2$CH(CH$_3$)—O—CH$_2$ | CH$_3$ |
| H | C$_2$H$_5$ | CH$_2$CH(CH$_3$)—O—CH$_2$ | CH$_3$ |
| H | CH$_3$ | CH$_2$CH(CH$_3$)—O—(CH$_2$)$_6$ | CH$_3$ |
| H | CH$_3$ | CH$_2$CH(CH$_3$)—O—CH(CH$_3$)CH$_2$ | C$_6$H$_5$ |
| H | H | CH$_2$CH(CH$_3$)—O—(CH$_2$)$_2$ | 4-FC$_6$H$_4$ |
| H | CH$_3$ | C(CH$_3$)$_2$(CH$_2$)$_6$ | H |
| H | C$_2$H$_5$ | C(CH$_3$)$_2$(CH$_2$)$_6$ | H |
| CH$_3$ | CH$_3$ | CH(CH$_3$)(CH$_2$)$_3$ | C$_6$H$_5$ |
| C$_2$H$_5$ | C$_2$H$_5$ | CH(CH$_3$)(CH$_2$)$_3$ | C$_6$H$_5$ |
| C$_2$H$_5$ | CH$_3$ | CH(CH$_3$)(CH$_2$)$_4$ | C$_6$H$_5$ |
| CH$_3$ | CH$_3$ | CH(CH$_3$)(CH$_2$)$_3$ | C$_6$H$_5$ |
| H | CH$_2$C$_6$H$_5$ | (CH$_2$)$_3$ | C$_6$H$_5$ |
| H | n-C$_6$H$_{13}$ | (CH$_2$)$_4$ | C$_6$H$_5$ |
| CH$_3$ | C$_2$H$_5$ | (CH$_2$)$_4$ | C$_6$H$_5$ |
| H | (CH$_2$)$_4$C$_6$H$_5$ | (CH$_2$)$_2$CH(C$_2$H$_5$) | C$_6$H$_5$ |
| CH$_3$ | CH$_3$ | C(CH$_3$)$_2$ | C$_6$H$_5$ |
| CH$_3$ | CH$_3$ | C(CH$_3$)$_2$(CH$_2$)$_3$ | C$_6$H$_5$ |
| C$_2$H$_5$ | C$_2$H$_5$ | (CH$_2$)$_6$ | C$_6$H$_5$ |
| CH$_3$ | CH$_3$ | (CH$_2$)$_8$ | C$_6$H$_5$ |
| CH$_3$ | CH$_3$ | CH(CH$_3$)(CH$_2$)$_7$ | C$_6$H$_5$ |
| H | n-C$_4$H$_9$ | CH$_2$ | C$_6$H$_5$ |

-continued

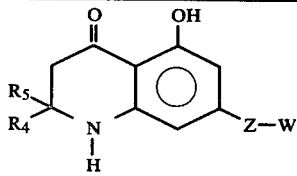

| R5 | R4 | Z | W |
|---|---|---|---|
| CH3 | CH3 | CH(CH3)(CH2)3 | 4-FC6H4 |
| CH3 | n-C6H13 | CH(CH3)CH2 | 4-FC6H4 |
| H | (CH2)2C6H5 | CH(CH3)(CH2)2CH(CH3) | C6H5 |
| H | CH3 | CH2 | C6H5 |
| H | CH2C6H5 | (CH2)3 | C5H9 |
| CH3 | CH3 | CH(CH3)CH2 | C5H9 |
| CH3 | CH2C6H5 | CH(CH3)(CH2)2 | C5H9 |
| CH3 | CH3 | CH(CH3)CH2 | C3H5 |
| H | (CH2)3C6H5 | CH(CH3)(CH2)5 | C6H11 |
| CH3 | CH3 | CH(CH3)(CH2)5 | C6H11 |
| CH3 | n-C4H9 | (CH2)4 | C3H5 |
| CH3 | CH3 | (CH2)9 | C6H11 |
| CH3 | CH3 | (CH2)3 | 2-pyridyl |
| CH3 | CH2C6H5 | (CH2)3 | 4-pyridyl |
| CH3 | CH3 | (CH2)4 | 4-pyridyl |
| C2H5 | C2H5 | (CH2)4 | 3-pyridyl |
| CH3 | CH3 | CH(CH3)CH(C2H5)CH2 | 4-pyridyl |
| H | n-C5H11 | CH(C2H5)(CH2)3 | 3-pyridyl |
| H | i-C3H7 | CH(CH3)(CH2)2 | 4-piperidyl |
| CH3 | CH3 | CH(C2H5)(CH2)2 | 2-piperidyl |
| CH3 | CH3 | CH(CH3)(CH2)2CH(CH3) | 4-piperidyl |
| CH3 | CH3 | CH(CH3)(CH2)2 | C7H13 |
| H | n-C4H9 | CH(CH3)(CH2)2 | C7H13 |
| CH3 | CH3 | CH(CH3)CH2—O—(CH2)2 | C6H5 |
| CH3 | CH2C6H5 | (CH2)4 | CH3 |
| CH3 | CH3 | CH(CH3)CH(CH3)—(CH2)5 | H |
| C2H5 | C2H5 | CH(CH3)CH(CH3)—(CH2)5 | H |
| CH3 | CH3 | CH2 | H |
| CH3 | C2H5 | (CH2)3 | CH3 |
| H | n-C6H13 | (CH2)6 | CH3 |
| CH3 | (CH2)3C6H5 | CH(CH3) | CH3 |
| CH3 | CH3 | (CH2)3 | H |
| H | n-C4H9 | CH(CH3) | C6H11 |
| CH3 | CH3 | (CH2)3—O— | C6H5 |
| CH3 | CH3 | (CH2)3—O— | 4-FC6H4 |
| CH3 | CH3 | (CH2)3—O— | C6H11 |
| C2H5 | C2H5 | (CH2)3—O— | C4H7 |
| H | CH2C6H5 | (CH2)3—O— | CH3 |
| CH3 | CH3 | (CH2)3—O— | 4-(4-FC6H4)C6H10 |
| C2H5 | C2H5 | (CH2)3—O—(CH2)2 | 4-ClC6H4 |
| CH3 | CH3 | (CH2)3—O—CH(CH3) | 4-piperidyl |
| H | n-C5H11 | CH(CH3)(CH2)2—O— | C6H5 |
| CH3 | CH3 | CH(CH3)(CH2)2—O—CH2 | CH3 |
| CH3 | CH3 | CH(CH3)(CH2)2—O—(CH2)4 | C6H5 |
| CH3 | CH3 | CH(CH3)(CH2)2—O—CH—(CH3) | C7H13 |
| CH3 | CH3 | CH(CH3)(CH2)2—O—CH2—CH(C2H5) | CH3 |
| CH3 | CH3 | (CH2)4—O— | C6H5 |
| C2H5 | C2H5 | (CH2)4—O—CH(CH3)CH2 | 3-piperidyl |
| CH3 | C2H5 | (CH2)4—O—CH2 | 4-FC6H4 |
| H | n-C3H7 | CH(CH3)(CH2)3—O— | 2-(4-FC6H5)C2H8 |
| CH3 | CH3 | CH(CH3)(CH2)3—O—(CH2)2 | C6H5 |
| CH3 | CH3 | CH(C2H5)(CH2)2—O—CH(CH3) | 4-piperidyl |
| CH3 | CH3 | CH(C2H5)(CH2)2—O— | C3H5 |
| CH3 | CH3 | CH(C2H5)(CH2)2—O— | 2-(4-FC6H11)C7H12 |
| CH3 | CH3 | (CH2)3—S— | C6H5 |
| C2H5 | C2H5 | (CH2)3—S—CH2 | 4-FC6H4 |
| CH3 | CH3 | (CH2)3—S— | C5H9 |
| CH3 | CH2C6H5 | (CH2)3—S—(CH2)4 | C6H5 |
| CH3 | CH3 | CH(CH3)(CH2)2—S— | 4-piperidyl |
| CH3 | CH3 | CH(CH3)(CH2)2—S—(CH2)4 | 4-pyridyl |
| CH3 | CH3 | CH(CH3)(CH2)2—S—(CH2)4 | C6H5 |
| C2H5 | C2H5 | CH(C2H5)(CH2)2—SO | C6H11 |
| H | n-C6H13 | CH(C2H5)(CH2)2—S— | 4-ClC6H4 |

-continued

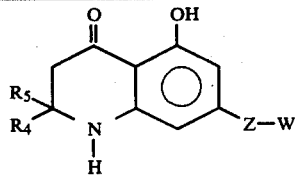

| R5 | R4 | Z | W |
|---|---|---|---|
| CH3 | n-C4H9 | CH(CH3)<br>CH(CH3)(CH2)3—S—<br>(CH2)4 | 4-FC6H4 |
| CH3 | CH3 | CH(CH3)(CH2)3—S—<br>(CH2)4 | 4-pyridyl |
| CH3 | CH3 | CH(CH3)CH2—O—(CH2)6 | C6H5 |
| CH3 | CH3 | C(CH3)2(CH2)6 | H |
| C2H5 | C2H5 | C(CH3)2(CH2)6 | H |

Of course, when Z contains an ether or thioether linkage, the procedure of Example 14 is used for the cyclization step.

EXAMPLE 19 d,l-5-Hydroxy-2-methyl-7-(2-heptyloxy)-4-oxo-1,2,3,4-tetrahydroquinoline

Potassium hydroxide pellets (325 mg., 52 mmole) is added to a solution of d,l-5,7-dihydroxy-2-methyl-4-oxo-1,2,3,4-tetrahydroquinoline (1.0 g., 52 mmole) in N,N-dimethylformamide (10 ml.). The mixture is slowly heated to 100° C. and to the resulting solution d,l-2-bromoheptane (1.08 g., 60 mmole) is added all at once with good stirring. After 10 minutes additional potassium hydroxide (160 mg.) is added followed by additional d,l-2-bromoheptane (500 mg.). The addition of potassium hydroxide and d,l-2-bromoheptane was repeated two more times using 80 mg. potassium hydroxide and 250 mg d,l-2-bromoheptane each time. The reaction mixture is stirred an additional 10 minutes and is then cooled. Chloroform (50 ml.) and aqueous sodium hydroxide (25 ml. of 1N) are added, the mixture stirred for 10 minutes and the layers separated. The chloroform extraction is repeated, the extracts combined, dried (MgSO4) and concentrated under reduced pressure to a dark oil. The oil is chromatographed on silica gel (120 g.) using benzene as solvent. Fractions of 30 ml. each are collected. The 12th–18th fractions are combined and concentrated under reduced pressure to a light yellow oil (850 mg.) which crystallizes upon standing.

The desired product is separated by filtration and recrystallized from hot hexane, m.p. 76°–77° C.

The above procedure is repeated on a 20-fold scale but using benzene-ethyl acetate (9:1) as chromatographic solvent. Fractions of 750 ml. each are collected. Combination of the 2nd–6th fractions affords 32 g. of oil which partially crystallizes from hexane upon standing and cooling to give 18.2 g. of product. An additional 3.2 g. is obtained by concentrating the mother liquor and allowing it to crystallize by standing in the cold. Total yield=21.4 g.

Analysis: Calc'd for $C_{17}H_{25}O_3N$: C, 70.07; H, 8.65; N, 4.81%. Found: C, 69.82; H, 8.67; N, 4.93%.

m/e - 291 (m+)

IR (KBr): 6.01 μ (=O)

In like manner, 5,7-dihydroxy-4-oxo-1,2,3,4-tetrahydroquinoline converted to d,l-5-hydroxy-7-(2-heptyloxy)-4-oxo-1,2,3,4-tetrahydroquinoline, an oil.

$^1$H NMR (60 MHz) $\delta_{CDCl_3}^{TMS}$ (ppm): 13.3 (s, 1H, phenolic), 5.5 and 5.7 (d, 2H, J=2 Hz, aromatic), 4.6 (bs, 1H, —NH), 4.1–4.6 (m, 1H, —O—CH—), 3.3 (t, 2H, J=7 Hz, —CH2—), 2.6 (t, 2H, J=7 Hz, —CH2—), 2.0–0.7 (m, remaining protons).

EXAMPLE 20

The following compounds are prepared according to the procedure of Example 19 but using the appropriate Br-(alk2)$_n$-W reactant and the appropriate 5,7-dihydroxy-2-R4R5-4-oxo-1,2,3,4-tetrahydroquinoline or 5-hydroxy-7-thiol-2-R4R5-4-oxo-1,2,3,4-tetrahydroquinoline.

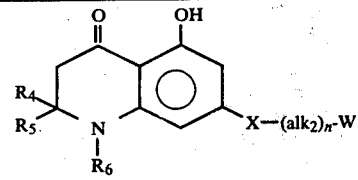

| R5 | R4 | X | -alk2- | W | R6 |
|---|---|---|---|---|---|
| H | H | O | CH2 | H | H |
| H | CH3 | O | CH2 | H | H |
| H | CH3 | O | (CH2)2 | H | H |
| H | H | O | (CH2)4 | H | CH3 |
| H | CH3 | O | (CH2)6 | H | H |
| H | CH3 | O | (CH2)9 | H | H |
| H | H | O | CH(CH)3CH2 | H | C2H5 |
| H | CH3 | O | CH(CH3)(CH2)3 | H | CH3 |
| H | H | O | CH(CH3)(CH2)4 | CH3 | H |
| H | C2H5 | O | CH2 | C6H5 | CH2C6H5 |

-continued

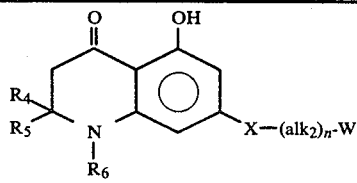

| R₅ | R₄ | X | -alk₂- | W | R₆ |
|---|---|---|---|---|---|
| H | H | O | (CH₂)₂ | C₆H₅ | CH₂COOH |
| H | CH₃ | O | (CH₂)₄ | C₆H₅ | CH₂COOH |
| H | C₂H₅ | O | CH₂ | 4-ClC₆H₄ | H |
| H | H | O | CH₂ | 4-FC₆H₄ | H |
| H | CH₃ | O | CH(CH₃)CH₂ | C₆H₅ | CH₃ |
| H | H | O | CH(CH₃)(CH₂)₂ | C₆H₅ | CH₃ |
| H | CH₃ | O | CH(CH₃)(CH₂)₃ | C₆H₅ | H |
| H | C₂H₅ | O | (CH₂)₇ | C₆H₅ | H |
| H | H | O | CH(CH₃)CH(CH₃)(CH₂)₄ | CH₃ | H |
| H | H | O | (CH₂)₂ | 4-pyridyl | C₂H₅ |
| H | CH₃ | O | (CH₂)₃ | 4-pyridyl | H |
| H | C₂H₅ | O | (CH₂)₃ | 3-pyridyl | n-C₄H₉ |
| H | CH₃ | O | CH(CH₃)CH₂ | 2-pyridyl | H |
| H | H | O | CH₂ | C₃H₅ | H |
| H | CH₃ | O | CH₂ | C₃H₅ | H |
| H | CH₃ | O | CH(CH₃) | C₄H₇ | H |
| H | CH₃ | O | (CH₂)₂ | C₅H₉ | H |
| H | CH₃ | O | CH₂ | C₆H₁₁ | H |
| H | CH₃ | O | (CH₂)₃ | C₆H₁₁ | H |
| H | C₂H₅ | O | (CH₂)₃ | C₅H₉ | H |
| H | CH₃ | O | (CH₂)₄ | C₇H₁₃ | H |
| H | H | O | — | C₆H₅ | H |
| H | CH₃ | O | — | C₆H₅ | CH₃ |
| H | H | O | — | 4-FC₆H₄ | H |
| H | H | O | — | 4-ClC₆H₄ | (CH₂)₂C₆H₅ |
| H | C₂H₅ | O | — | C₆H₅ | H |
| H | H | O | — | C₅H₉ | H |
| H | C₂H₅ | O | — | C₅H₉ | H |
| H | CH₃ | O | — | C₆H₁₁ | H |
| H | H | O | — | C₇H₁₃ | H |
| H | H | O | — | 2-(C₆H₅)C₃H₄ | H |
| H | H | O | — | 2-(C₆H₅)C₃H₄ | CH₃ |
| H | C₂H₅ | O | — | 4-(C₆H₅)C₆H₁₀ | H |
| H | H | O | — | 3-(C₆H₅)C₇H₁₂ | H |
| H | H | O | — | 4-pyridyl | C₂H₅ |
| H | CH₃ | O | — | 4-pyridyl | H |
| H | C₂H₅ | O | — | 4-piperidyl | H |
| H | CH₃ | O | — | 2-pyridyl | H |
| H | CH₃ | O | — | 3-piperidyl | H |
| H | H | S | CH₂ | H | H |
| H | CH₃ | S | CH₂ | H | H |
| H | H | S | (CH₂)₃ | H | (CH₂)₂COOH |
| H | CH₃ | S | (CH₂)₃ | H | (CH₂)₂COOH |
| H | H | S | (CH₂)₅ | H | H |
| H | CH₃ | S | (CH₂)₅ | H | H |
| H | C₂H₅ | S | (CH₂)₄ | H | H |
| H | H | S | (CH₂)₉ | H | H |
| H | CH₃ | S | CH(CH₃)(CH₂)₅ | H | (CH₂)₃COOH |
| H | H | S | CH(CH₃)(CH₂)₃ | H | H |
| H | CH₃ | S | CH₂ | C₃H₅ | H |
| H | H | S | CH₂ | C₆H₁₁ | H |
| H | CH₃ | S | (CH₂)₃ | C₆H₁₁ | H |
| H | C₂H₅ | S | (CH₂)₄ | C₇H₁₃ | H |
| H | H | S | CH(CH₃) | C₄H₇ | H |
| H | H | S | CH(CH₃)CH(CH₃)(CH₂)₄ | CH₃ | H |
| H | CH₃ | S | CH(CH₃)CH(CH₃)(CH₂)₄ | CH₃ | H |
| H | H | S | C(CH₃)₂(CH₂)₅ | CH₃ | H |
| H | CH₃ | S | C(CH₃)₂(CH₂)₅ | CH₃ | H |
| H | CH₃ | S | CH₂ | C₆H₅ | H |
| H | CH₃ | S | (CH₂)₄ | C₆H₅ | H |
| H | H | S | CH(CH₃)(CH₂)₂ | C₆H₅ | H |
| H | CH₃ | S | CH(CH₃)(CH₂)₃ | C₆H₅ | CH₃ |
| H | CH₃ | S | CH₂ | 4-FC₆H₄ | H |
| H | H | S | CH₂ | 4-ClC₆H₄ | H |
| H | CH₃ | S | (CH₂)₃ | 4-pyridyl | H |
| H | C₂H₅ | S | CH(CH₃)CH₂ | 2-pyridyl | H |
| H | H | S | — | C₆H₅ | H |
| H | CH₃ | S | — | 4-FC₆H₄ | H |
| H | C₂H₅ | S | — | C₅H₉ | H |
| H | CH₃ | S | — | C₆H₁₁ | H |
| H | H | S | — | 4-pyridyl | H |

-continued

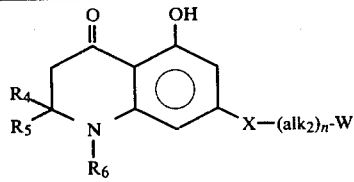

| R5 | R4 | X | -alk2- | W | R6 |
|---|---|---|---|---|---|
| H | CH3 | S | — | 4-piperidyl | CH2C6H5 |
| H | CH3 | S | — | C7H13 | H |
| H | CH3 | S | — | 2-(C6H5)C3H4 | H |
| H | CH3 | S | — | 4-(C6H5)C6H10 | H |
| H | H | S | — | 4-ClC6H4 | H |
| H | H | S | CH(CH3)(CH2)4 | CH3 | CH3 |
| H | CH3 | S | CH(CH3)(CH2)3 | C6H5 | CH3 |
| H | H | S | C(CH3)2(CH2)5 | CH3 | i-C3H7 |
| H | C2H5 | S | (CH2)4 | CH3 | (CH2)3C6H5 |
| H | CH3 | O | CH(CH3)(CH2)4 | CH3 | (CH2)4C6H5 |
| H | CH3 | O | CH(CH3)(CH2)3 | C6H5 | n-C4H9 |
| H | CH3 | O | CH(CH3)(CH2)3 | C6H5 | CH2COOH |
| H | H | O | CH(CH3)(CH2)3 | C6H5 | CH2COOH |
| H | H | O | CH(CH3)(CH2)3 | C6H5 | (CH2)4COOH |
| CH3 | CH3 | O | CH2 | H | H |
| C2H5 | CH3 | O | (CH2)4 | H | CH3 |
| CH3 | CH3 | O | (CH2)9 | H | H |
| CH3 | CH3 | O | CH(CH3)(CH2)3 | CH3 | H |
| CH3 | CH3 | O | CH(CH3)(CH2)4 | CH3 | H |
| CH3 | n-C6H13 | O | CH(CH3)CH(CH3)(CH2)4 | CH3 | H |
| C2H5 | C2H5 | O | C(CH3)2(CH2)4 | CH3 | H |
| CH3 | CH3 | O | CH(CH3)(CH2)3 | C6H5 | H |
| H | n-C6H13 | O | CH(CH3)(CH2)4 | CH3 | CH3 |
| CH3 | CH3 | O | CH(CH3)(CH2)3 | 4-FC6H4 | n-C3H7 |
| H | CH3 | O | CH(CH3)(CH2)4 | CH3 | n-C6H13 |
| H | C2H5 | O | CH(CH3)(CH2)3 | CH3 | CH2COOH |
| H | CH3 | O | CH(CH3)(CH2)3 | 4-ClC6H4 | (CH2)4COOH |
| CH3 | CH3 | O | (CH2)3 | 4-pyridyl | CH2C6H5 |
| CH3 | CH2C6H5 | O | CH(CH3)(CH2)3 | 3-pyridyl | H |
| CH3 | n-C4H9 | O | — | C6H5 | H |
| CH3 | (CH2)3C6H5 | O | — | 4-FC6H4 | CH2C6H5 |
| CH3 | CH3 | O | — | 4-pyridyl | (CH2)4C6H5 |
| CH3 | CH3 | O | — | C5H9 | H |
| C2H5 | C2H5 | O | — | C7H13 | H |
| H | C2H5 | O | — | 3-piperidyl | H |
| CH3 | CH3 | O | — | 2-(C6H5)C3H4 | CH3 |
| CH3 | CH3 | O | — | 3-(C6H5)C7H12 | H |
| CH3 | CH3 | O | CH2 | C3H5 | H |
| CH3 | CH3 | O | (CH2)3 | C6H11 | (CH2)2COOH |
| CH3 | C2H5 | O | (CH2)4 | C7H13 | (CH2)4COOH |
| CH3 | CH3 | S | — | C6H5 | n-C5H11 |
| CH3 | CH3 | S | — | 4-ClC6H4 | H |
| CH3 | CH3 | S | — | C7H13 | H |
| CH3 | CH3 | S | — | 4-(C6H5)C6H10 | H |
| H | n-C4H9 | S | — | C6H5 | H |
| CH3 | (CH2)3C6H5 | S | — | 4-pyridyl | CH2C6H5 |
| CH3 | CH2C6H5 | S | — | C6H11 | CH3 |
| C2H5 | (CH2)2C6H5 | S | — | 4-FC6H4 | CH2COOH |
| CH3 | CH3 | S | — | 4-(C6H5)C6H10 | (CH2)4COOH |
| CH3 | n-C6H13 | S | — | C6H5 | H |
| CH3 | CH2C6H5 | S | — | C6H5 | H |
| C2H5 | C2H5 | S | CH2 | H | H |
| CH3 | CH3 | S | (CH2)5 | H | CH3 |
| CH3 | CH3 | S | (CH2)9 | H | i-C3H7 |
| CH3 | CH3 | S | C(CH3)2(CH2)6 | H | (CH2)3C6H5 |
| CH3 | CH3 | S | CH(CH3)(CH2)4 | CH3 | CH2C6H5 |
| CH3 | CH3 | S | CH(CH3)(CH2)3 | C6H5 | H |
| C2H5 | n-C4H9 | S | CH(CH3)(CH2)3 | C6H11 | i-C3H7 |
| H | CH2C6H5 | S | C(CH3)2(CH2)6 | H | H |
| CH3 | (CH2)2C6H5 | S | 2-(C6H5)C3H4 | H | H |
| H | n-C3H7 | O | C(CH3)2(CH2)6 | 4-pyridyl | H |
| C2H5 | n-C4H9 | O | CH2 | CH3 | H |
| CH3 | (CH2)4C6H5 | O | (CH2)4 | CH3 | H |
| C2H5 | (CH2)3C6H5 | S | — | C6H5 | H |
| CH3 | CH3 | O | CH2 | C6H5 | n-C6H13 |
| CH3 | CH2C6H5 | O | (CH2)6 | 4-FC6H4 | n-C4H9 |
| CH3 | n-C4H9 | O | CH(CH3)(CH2)3 | H | CH3 |
| CH3 | CH3 | O | C(CH3)2(CH2)5 | CH3 | CH2COOH |

EXAMPLE 21 d,l-5-Hydroxy-2-methyl-7-(5-phenyl-2-pentyloxy)-4-oxo-1,2,3,4-tetrahydroquinoline A mixture of 5-phenyl-2-(R,S)-pentanol (16.4 g., 100 mmole), triethylamine (28 ml., 200 mmole) and dry tetrahydrofuran (80 ml.) under a nitrogen atmosphere is cooled in an ice/water bath. Methanesulfonyl chloride (8.5 ml., 110 mM) in dry tetrahydrofuran (20 ml.) is added dropwise at such a rate that the temperature holds essentially constant. The mixture is allowed to warm to room temperature and is then filtered to remove triethylamine hydrochloride. The filter cake is washed with dry tetrahydrofuran and the combined wash and filtrate evaporated under reduced pressure to give the product as an oil. The oil is dissolved in chloroform (100 ml.) and the solution washed with water (2×100 ml.) and then with saturated brine (1×20 ml.). Evaporation of the solvent affords 21.7 g. (89.7%) yield of the mesylate of d,l-5-phenyl-2-pentanol which is used in the next step without further purification.

A mixture of d,l-5,7-dihydroxy-2-methyl-4-oxo-1,2,3,4-tetrahydroquinoline (1.0 g., 5.2 mmole), potassium carbonate (14.35 g., 0.104 mole), N,N-dimethylformamide (60 ml.) and d,l-5-phenyl-2-pentanol mesylate (13.68 g., 57 mmole), under a nitrogen atmosphere, is heated to 80°–82° C. in an oil bath for 1.75 hours. The mixture is cooled to room temperature and then poured into ice/water (300 ml.). The aqueous solution is extracted with ethyl acetate (2×50 ml.) and the combined extracts washed successively with water (3×50 ml.) and saturated brine (1×50 ml.). The extract is then dried (MgSO$_4$), decolorized with charcoal and evaporated to give the product.

m/e - 339 (m+)

The above procedure is repeated but using 114.8 g. (0.594 mole) of d,l-5,7-dihydroxy-2-methyl-4-oxo-1,2,3,4-tetrahydroquinoline, 612 ml. of N,N-dimethylformamide, 174.8 g. (1.265 moles) of potassium carbonate and 165.5 g. (0.638 mole) of d,l-5-phenyl-2-pentanol mesylate. The reaction mixture is cooled and poured onto ice water (4 liters) and the aqueous solution extracted with ethyl acetate (2×4 liters). The combined extract is washed with water (4×2 liters), brine (1×2 liters) and dried (MgSO$_4$). Evaporation affords 196 g. of the title product. It is used without further purification.

$^1$H NMR (60 MHz) $\delta_{CDCl_3}^{TMS}$ (ppm): 12.73 (s, 1H, OH), 7.22 (s, 5H, aromatic), 5.80 (d, J=3 H$_3$, 1H, meta H), 5.58 (d, J=3 H$_3$, 1H, meta H), 1.25 (d, 6H, CH$_3$-CH-N and CH$_3$-CH-O-), 1.41–4.81 (m, 11H, remaining protons).

EXAMPLE 22 d,l-5-Hydroxy-7-(5-phenyl-2-pentyloxy)-4-oxo-1,2,3,4-tetrahydroquinoline

Repetition of the procedure of Example 21 but using 5,7-dihydroxy-4-oxo-1,2,3,4-tetrahydroquinoline in place of the 5,7-dihydroxy-2-methyl-4-oxo-1,2,3,4-tetrahydroquinoline affords d,l-5-hydroxy-7-(5-phenyl-2-pentyloxy)-4-oxo-1,2,3,4-tetrahydroquinoline as an oil in 74% yield.

m/e - 325 (m+)

Analysis: Calc'd for C$_{20}$H$_{23}$NO$_3$: C, 73.70; H, 7.12; N, 4.31%. Found: C, 73.69; H, 7.15; N, 4.08%.

$^1$H NMR (60 MHz) $\delta_{CDCl_3}^{TMS}$ (ppm): 12.6 (bs, 1H, phenolic), 7.3 (s, 5H, aromatic), 5.8 (d, 1H, aromatic, J=2 Hz), 5.6 (d, 1H, aromatic, J=2 Hz), 4.7–4.1 (m, 2H, NH and O—CH), 3.5 (t, 2H, CH$_2$, J=7 Hz), 3.1–2.1 (m, 4H, 2—CH$_2$—), 2.1–1.5 (m, 4H, 2—CH$_2$), 1.3 (d, 3H, —CH—CH$_3$, J=6 Hz).

Similarly, d,l-5,7-dihydroxy-2-methyl-4-oxo-1,2,3,4-tetrahydroquinoline (27 g., 0.14 mole) is alkylated with 4-phenylbutyl methanesulfonate (35.2 g., 0.154 mole) to yield 41.1 g. (90%) of the desired d,l-5-hydroxy-2-methyl-7-(4-phenylbutyloxy)-4-oxo-1,2,3,4-tetrahydroquinoline, m.p. 88°–90° C. Recrystallization from ethyl acetate-hexane (1:2) gives the analytical sample, m.p. 90°–91° C.

Calc'd for C$_{20}$H$_{23}$O$_3$N: C, 73.82; H, 7.12; N, 4.30%. Found: C, 73.60; H, 7.09; N, 4.26%.

m/e - 325 (m+)

$^1$H NMR (60 MHz) $\delta_{CDCl_3}^{TMS}$ (ppm): 12.58 (s, 1H, —OH), 7.21 (s, 5H, C$_6$H$_5$), 5.74 (d, J=2.5 Hz, 1H, meta H), 5.5 (d, J=2.5 Hz, 1H, meta H), 4.36 (bs, 1H, NH), 3.33–4.08 (m, 3H, —O—CH$_2$, —CH—N), 2.29–2.83 (m, 4H, —CH$_2$—C=O, C$_6$H$_5$—CH$_2$), 1.51–1.92 (m, 4H, —[CH$_2$]$_2$]), 1.23 (d, 3H, CH$_3$—).

In like manner, alkylation of d-5,7-dihydroxy-4-oxo-1,2,3,4-tetrahydroquinoline with d-2-octylmethanesulfonate gives d-5-hydroxy-2-methyl-7-(2-(R)-octyloxy)-4-oxo-1,2,3,4-tetrahydroquinoline, m.p. 64°–68° C. [α]$_D^{25}$ = +110.2° (c=1.0, CHCl$_3$).

and alkylation of d,l-5,7-dihydroxy-2-propyl-4-oxo-1,2,3,4-tetrahydroquinoline with d,l-5-phenyl-2-phenol mesylate gives d,l-5-hydroxy-7-(5-phenyl-2-pentyloxy)-2-propyl-4-oxo-1,2,3,4-tetrahydroquinoline; m/e - 367 (m+).

EXAMPLE 23

The following compounds are prepared from appropriate reactants by the procedure of Example 21. The necessary alkanol reactants not previously described in the literature are prepared from appropriate aldehydes or ketones by the procedures of Preparations G and H.

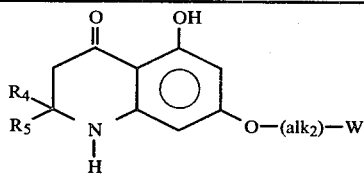

| R$_5$ | R$_4$ | alk$_2$ | W |
|---|---|---|---|
| H | CH$_3$ | CH$_2$C(CH$_3$)$_2$(CH$_2$)$_4$ | CH$_3$ |
| H | CH$_3$ | CH$_2$CH(CH$_3$)(CH$_2$)$_2$CH(CH$_3$)CH$_2$ | CH$_3$ |
| H | CH$_3$ | CH(CH$_3$)CH$_2$CH(CH$_3$)CH$_2$CH(CH$_3$) | CH$_3$ |
| H | H | CH(CH$_3$)(CH$_2$)$_2$C(CH$_3$)$_2$ | CH$_3$ |

-continued

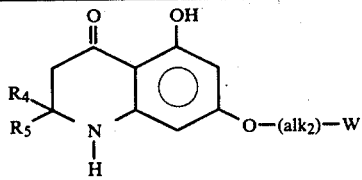

| R5 | R4 | alk2 | W |
|---|---|---|---|
| H | C2H5 | CH2CH(C2H5) | C6H5 |
| H | CH3 | CH2CH2CH(CH3) | C6H5 |
| H | CH3 | (CH2)7 | C6H5 |
| H | H | CH(CH3)(CH2)5 | C6H5 |
| H | C2H5 | (CH2)9 | C6H5 |
| H | H | (CH2)9 | CH3 |
| H | H | CH(CH3)CH2 | 2-pyridyl |
| H | C2H5 | (CH2)2 | 2-pyridyl |
| H | C2H5 | (CH2)4 | 2-pyridyl |
| H | H | (CH2)3 | 2-piperidyl |
| H | CH3 | (CH2)3 | 4-piperidyl |
| H | CH3 | (CH2)3 | 4-FC6H4 |
| H | H | (CH2)3 | 4-ClC6H4 |
| H | C2H5 | (CH2)4 | 4-FC6H4 |
| H | H | CH(CH3)(CH2)2 | 2-pyridyl |
| H | C2H5 | CH(CH3)(CH2)2 | 3-pyridyl |
| H | CH3 | CH2CC(CH3)2 | C6H5 |
| H | CH3 | CH(CH3)(CH2)3 | 4-pyridyl |
| H | CH3 | CH(CH3)(CH2)2 | 4-piperidyl |
| H | C2H5 | CH(C2H5)(CH2)2 | 4-piperidyl |
| H | H | CH(CH3)(CH2)2 | 4-FC6H4 |
| H | CH3 | CH(CH3)(CH2)2 | 4-ClC6H4 |
| H | H | CH2 | C6H5 |
| H | CH3 | CH2 | 4-FC6H4 |
| H | CH3 | — | 4-FC6H4 |
| H | C2H5 | — | 4-ClC6H4 |
| H | H | — | 4-FC6H4 |
| H | CH3 | — | C3H5 |
| H | H | — | C3H5 |
| H | CH3 | — | C4H7 |
| H | C2H5 | — | C5H9 |
| H | CH3 | — | C6H11 |
| H | CH3 | — | C7H13 |
| H | CH3 | — | 2-(C6H5)C3H4 |
| H | CH3 | — | 1-(C6H5)C4H6 |
| H | CH3 | — | 2-(C6H5)C5H8 |
| H | CH3 | — | 4-(C6H5)C6H10 |
| H | C2H5 | — | 3-(C6H5)C6H10 |
| H | CH3 | — | 4-pyridyl |
| H | CH3 | — | 4-piperidyl |
| H | CH3 | — | 2-(C6H5)C6H10 |
| H | H | — | 4-(C6H5)C6H10 |
| H | CH3 | — | 3-(C6H5)C7H12 |
| H | CH3 | —CH2— | CH3 |
| H | CH3 | —(CH2)3— | CH3 |
| H | CH3 | —(CH2)6— | CH3 |
| H | CH3 | —(CH2)9— | CH3 |
| H | H | —(CH2)6— | CH3 |
| H | C2H5 | —(CH2)3— | CH3 |
| H | CH3 | —C(CH3)2(CH2)5— | CH3 |
| H | CH3 | —C(CH3)2(CH2)5— | CH3 |
| H | CH3 | —CH(CH3)CH(CH3)(CH2)4— | CH3 |
| CH3 | CH3 | —CH(CH3)(CH2)3— | C6H5 |
| CH3 | CH3 | —(CH2)4— | C6H5 |
| CH3 | CH3 | —C(CH3)2(CH2)6— | H |
| CH3 | CH3 | — | C6H5 |
| CH3 | CH3 | — | 4-ClC6H4 |
| CH3 | CH3 | —CH(CH3)(CH2)2— | 2-pyridyl |
| H | CH2C6H5 | —CH(CH3)(CH2)4— | H |
| H | CH2C6H5 | —C(CH3)2(CH2)6— | H |
| CH3 | CH2C6H5 | — | 4-FC6H4 |
| H | (CH2)3C6H5 | —CH2— | C6H5 |
| H | (CH2)4C6H5 | —(CH2)6— | CH3 |
| C2H5 | C2H5 | —(CH2)4— | C6H5 |
| C2H5 | CH3 | —CH2— | 4-FC6H4 |
| H | i-C3H7 | —CH(CH3)(CH2)3— | 4-piperidyl |
| H | n-C4H9 | —CH(CH3)CH(CH3)(CH2)5— | H |
| H | n-C6H13 | —C(CH3)2(CH2)6 | H |
| CH3 | n-C6H13 | —(CH2)3— | CH3 |
| CH3 | CH3 | — | C5H9 |

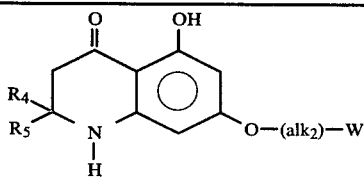

| R5 | R4 | alk2 | W |
| --- | --- | --- | --- |
| CH3 | CH3 | — | 4-(C6H5)C6H10 |

EXAMPLE 24 d,l-1-Formyl-5-hydroxy-3-hydroxymethylene-2-methyl-7-(5-phenyl-2-pentyloxy)-4-oxo-1,2,3,4-tetrahydroquinoline A solution of d,l-5-hydroxy-2-methyl-7-(5-phenyl-2-pentyloxy)-4-oxo-1,2,3,4-tetrahydroquinoline (195 g., ca. 0.58 mole) in ethyl formate (1140 g., 14.6 moles) is added dropwise to sodium hydride (72 g., 3.0 moles, obtained by washing 144 g. of 50% sodium hydride with hexane, 3×500 ml.), with good stirring. After about 1.5 hours when ⅔ of the ethyl formate solution is added, the addition is discontinued to allow the vigorous foaming to subside. Diethyl ether (600 ml.) is added and the mixture stirred for 15 minutes before adding the remainder of the ethyl formate solution. When addition is complete diethyl ether (600 ml.) is added, the reaction mixture stirred for an additional 10 minutes and then poured onto ice water (2 liters). It is acidified to pH 1 with 10% HCl and the phase separated and extracted with ethyl acetate (2×2 liters). The combined organic solutions are washed successively with water (2×2 liters), brine (1×one liter) and dried (MgSO4). Concentration gives 231 g. of red-brown oil which is used without further purification.

$R_f$=0.1–0.5 (stretched) on thin layer chromatography, silica gel plates, benzene/ether (1:1).

Similarly, d,l-5-dihydroxy-7-(5-phenyl-2-pentyloxy)-2-propyl-4-oxo-1,2,3,4-tetrahydroquinoline is converted to d,l-1-formyl-5-hydroxy-3-hydroxymethylene-7-(5-phenyl-2-pentyloxy)-2-propyl-4-oxo-1,2,3,4-tetrahydroquinoline. It is used in subsequent examples as is.

EXAMPLE 25 d,l-1-Formyl-5-hydrpxy-3-hydroxymethylene-2-methyl-7-(2-heptyloxy)-4-oxo-1,2,3,4-tetrahydroquinoline To sodium hydride (18.2 g., 0.38 mol) obtained by washing 50% sodium hydride in mineral oil dispersion with pentane is added dropwise, over a half-hour period, a solution of d,l-5-hydroxy-2-methyl-7-(2-heptyloxy)-4-oxo-1,2,3,4-tetrahydroquinoline (11.1 g., 0.038 mole) in ethyl formate (110 g., 1.48 moles). Exothermic reaction occurs with vigorous evolution of hydrogen and formulation of a yellow precipitate. The reaction mixture is cooled, either (750 ml.) added and the resulting mixture then heated at reflux and stirred for 3 hours. It is then cooled to 0° C. and neutralized by addition of 1N hydrochloric acid (400 ml.). The ether layer is separated and the aqueous phase extracted with ether (2×150 ml.). The ether extracts are combined, washed successively with saturated sodium bicarbonate solution (2×100 ml.) and brine (1×150 ml.) and then dried (MgSO4). Concentration of the dried extract affords an orange foam (10.8 g.). An additional 2.3 g. is obtained by acidifying the sodium bicarbonate wash solutions with concentrated hydrochloric acid followed by extraction of the acid solution with ether (2×100 ml.). Concentration of the combined ethereal extracts after drying gives 2.3 g. of product (Total=13.1 g.). The product is used as is.

$^1$H NMR (60 MHz) $\delta_{CDCl_3}^{TMS}$ (ppm): 12.27 (bs, 1H, ArOH), 8.8–11.9 (m, 1H, variable, =COH), 8.73 (s, 1H, N—CHO), 7.41 (s, 1H, =CH), 6.32 (s, 2H, aromatic), 5.52 (q, 1H, —CH—N), 4.18–4.77 (m, 1H, —O—CH), 0.6–2.0 (m, 17H, CH3—C—C5H11 and CH3—C—N).

In like manner, d,l-5-hydroxy-2-methyl-7-(5-phenyl-2-pentyloxy)-4-oxo-1,2,3,4-tetrahydroquinoline is converted to d,l-1-formyl-5-hydroxy-3-hydroxymethylene-2-methyl-7-(5-phenyl-2-pentyloxy)-4-oxo-1,2,3,4-tetrahydroquinoline.

$^1$H NMR: (60 MHz) $\delta_{CDCl_3}^{TMS}$ (60 MHz) $\delta_{CDCl_3}^{TMS}$ (ppm): 12.22 (bs, 1H, ArOH), 8.8–11.6 (variable, 1H, =COH), 8.64 (s, 1H, —CHO), 7.21 (bs, shoulder at 7.30, 6H, aromatic and =CH), 6.23 and 6.17 (two 1H doublets, J=2 Hz meta), 5.42 (bq, 1H, N—CH), 4.18–4.70 (m, 1H, —OCH), 2.4–3.0 (m, 2H, Ar—CH2), 1.53–2.0 (m, 4H, —(CH2)2—), 1.29 (overlapping doublets, 6H, CH3—C—N and CH3—C—O).

d,l-5-hydroxy-7-(2-heptyloxy)-4-oxo-1,2,3,4-tetrahydroquinoline is converted to d,l-1-formyl-5-hydroxy-3-hydroxymethylene-7-(2-heptyloxy)-4-oxo-1,2,3,4-tetrahydroquinoline, an oil.

$^1$H NMR (60 MHz) $\delta_{CDCl_3}^{TMS}$ (ppm): 12.1 (bs, 1H, phenolic), 8.8 (s, 1H, —N—CHO), 8.1 (s, 1H), 7.3 (s, 1H), 6.1 (s, 2H, aromatic), 4.5 (bs, 2H, —CH2—), 4.2–4.8 (m, —O—CH2—), 2.0–0.7 (remaining protons).

d,l-5-hydroxy-7-(5-pentyl-2-pentyloxy)-4-oxo-1,2,3,4-tetrahydroquinoline is converted to d,l-1-formyl-5-hydroxy-3-hydroxymethylene-7-(5-phenyl-2-pentyloxy)-4-oxo-1,2,3,4-tetrahydroquinoline.

$^1$H NMR (60 MHz) $\delta_{CDCl_3}^{TMS}$ (ppm): 12.4 (bs, 1H, phenolic, 8.5 (s, 1H, CHO), 7.2 (m, 6H, aromatic and =CH—), 6.2 (m, 2H, aromatic), 4.5 (s, 2H, —CH2—), 4.4 (m, 1H, —CH—CH3), 2.6 (bt, 2H, —CH2—), 1.7 (m, 5H, remaining protons), 1.3 (d, 3H, —CH—CH3, J=6 Hz).

and d,l-5-hydroxy-2-methyl-7-(4-phenylbutyloxy)-4-oxo-1,2,3,4-tetrahydroquinoline is converted to d,l-1-formyl-5-hydroxy-3-hydroxymethylene-2-methyl-7-(4-phenylbutyloxy)-4-oxo-1,2,3,4-tetrahydroquinoline, m.p. 132°–135° C. (from hexane). Recrystallization from hot methanol provides the analytical sample, m.p. 131°–132° C.

Calc'd for $C_{22}H_{23}O_5N$: C, 69.27; H, 6.08; N, 3.67%. Found: C, 69.25; H, 5.88; N, 3.88%.

m/e - 381 (m+)

$^1$H NMR (60 MHz) $\delta_{CDCl_3}^{TMS}$ (ppm): 12.4–13.6

(m, H, 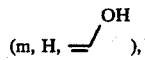), 12.26 (s, 1H, 5—OH), 8.62 (s, 1H, —C(=O)—H), ca. 7.18–7.48

(m, 1H, 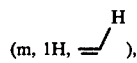), 7.27 (s, 5H, C$_6$H$_5$), 6.26 (bs, 2H, meta H's), 5.46 (q, 1H, CH—N), 3.82–4.23 (m, 3H, —CH$_2$—O), 2.49–2.80 (m, 3H, ArCH$_2$), 1.67–2.02 (m, 4H, —[CH$_2$]$_2$—), 1.27 (d, 3H, CH$_3$).

EXAMPLE 26 dl-1-Formyl-5-hydroxy-2-methyl-7-(5-phenyl-2-pentyloxy)-4-oxo 3-(3-oxobutyl)-1,2,3,4-tetrahydroquinoline To a solution of dl-1-formyl-3-hydroxymethylene-5-hydroxy-2-methyl-7-(5-phenyl-2-pentyloxy)-4-oxo-1,2,3,4-tetrahydroquinoline (229 g., ca. 0.58 mole) in methanol (880 ml.) under a nitrogen atmosphere is added triethylamine (27.2 ml.) with stirring. Methyl vinyl ketone (97.0 ml.) is then added and the mixture stirred overnight at room temperature.

The reaction is complete at this point and comprises a mixture of the title compound and dl-1,3-diformyl-5-hydroxy-2-methyl-7-(5-phenyl-2-pentyloxy)-4-oxo-3-(3-oxobutyl)-1,2,3,4-tetrahydroquinoline. The following steps are required to convert the diformyl compound to the desired title compound.

The reaction mixture is diluted with ether (6 liters) and then washed successively with 10% aqueous sodium carbonate (4×1700 ml.), brine (1×2 liters) and then drid (MgSO$_4$). Concentration of the solution affords 238 g. of a red-brown oil. The oil is dissolved in methanol (1920 ml.) and the solution cooled to 0° C. Potassium carbonate (21.2 g.) is added, the mixture stirred for 3 hours at 0° C. and then treated with acetic acid (18.7 g.). The methanol is removed under reduced pressure and the resultant oil stirred with water (2 liters) and ethyl acetate (2 liters) for 10 minutes. The aqueous phase is separated, extracted with ethyl acetate (1×2 liters) and the combined ethyl acetate solutions washed with water (2×2 liters), brine (1×2 liters) and dried (MgSO$_4$). Concentration under reduced pressure and chromatography of the concentrate on silica gel (1.8 kg.) gives 159 g. of the title product.

m/e - 437 (m+)

$^1$H NMR (60 MHz) $\delta_{CDCl_3}^{TMS}$ (ppm): 12.7 (s, 1H, OH), 8.78 (bs, 1H, —CHO), 7.22 (s, 5H, aromatic), 6.22 (bs, 2H, meta H's), 2.12, 2.07 (s, 3H, —CH$_3$—CO—), 1.31 (d, 3H, —CH$_3$—C—O—), and 1.57–5.23 (m, 13H, remaining protons).

Similar treatment of 35 g. (0.09 mole) of dl-1-formyl-5-hydroxy-3-hydroxymethylene-2-methyl-7-(4-phenylbutyloxy)-4-oxo-1,2,3,4-tetrahydroquinoline gives 22.7 g. (60%) of dl-1-formyl-5-hydroxy-2-methyl-7-(4-phenylbutyloxy)-4-oxo-3-(3-oxobutyl)-1,2,3,4-tetrahydroquinoline, m.p. 101°–103° C. The analytical sample is obtained by recrystallization from methanol, m.p. 104°–105° C.

Calc'd for C$_{25}$H$_{29}$O$_5$N: C, 70.90; H, 6.90; N, 3.31%. Found: C, 70.77; H, 6.81; N, 3.46%.

$^1$H NMR (60 MHz) $\delta_{CDCl_3}^{TMS}$ (ppm): 12.88 (s, 1H, —OH), 9.08 (bs, 1H, —CHO), 7.29 (s, 5H, C$_6$H$_5$), 6.25 (bs, 2H, meta H's), 4.88–5.43 (m, 1H, —CHN), 3.86–4.21 (m, 2H, —CH$_2$—O—), ca. 2.49–3.02 [m, 7H, ArCH$_2$, —(CH$_2$)$_2$—C(=O)—, —CH—C(=O)], 2.18 [s, 3H, CH$_3$—C(=O)], 1.68–2.03 [m, 4H, —(CH$_2$)$_2$—], 1.13 (d, 3H, CH$_3$).

m/e - 423 (m+);

and d,l-1-formyl-5-hydroxyl-3-hydroxymethylene-7-(5-phenyl-2-pentyloxy)-2-propyl-4-oxo-1,2,3,4-tetrahydroquinoline affords d,l-1-formyl-5-hydroxy-7-(5-phenyl-2-pentyloxy)-4-oxo-3-(3-oxobutyl)-1,2,3,4-tetrahydroquinoline which is used as is.

EXAMPLE 27 d,l-1-Formyl-5-hydroxy-2-methyl-7-(2-heptyloxy)-4-oxo-3-(3-oxobutyl)-1,2,3,4-tetrahydroquinoline and d,l-1,3-Diformyl-5-hydroxy-2-methyl-7-(2-heptyloxy)-4-oxo-3-(3-oxobutyl)-1,2,3,4-tetrahydroquinoline To a solution of d,l-5-hydroxy-3-hydroxymethylene-2-methyl-7-(2-heptyloxy)-4-oxo-1,2,3,4-tetrahydroquinoline (13.1 g., 37.7 mmol.), in methanol (56 ml.) and methyl vinyl ketone (5.52 mg., 68 mmol.) is added triethylamine (1.3 ml., 9.3 mmol.). The mixture is stirred for 18 hours under a nitrogen atmosphere at room temperature and is then diluted with ether (550 ml.). The solution is washed with 10% aqueous sodium bicarbonate solution (4×60 ml.) followed by brine (1×100 ml.) and dried (MgSO$_4$). Removal of the ether by evaporation gives a dark oil (16 g.). The oil is dissolved in a minimum volume of benzene and the solution charged to a column of silica gel (500 g.). The column is then eluted with a volume of benzene equal to the volume of the column. The eluting solvent is then changed to 15% ether-benzene and 100 ml. fractions collected when the first color band begins to elute off the column. Fractions 5-13 are combined and concentrated under reduced pressure to give d,l-1,3-diformyl-5-hydroxy-2-methyl-7-(2-heptyloxy)-4-oxo-3-(3-oxobutyl)-1,2,3,4-tetrahydroquinoline as a yellow oil (8.7 g.).

The column is eluted further with 15% ether-benzene. Fractions 19-37 are combined and concentrated under reduced pressure to give d,l-1-formyl-5-hydroxy-2-methyl-7-(2-heptyloxy)-3-(3-oxobutyl)-1,2,3,4-tetrahydroquinoline as an oil (4.6 g.). Additional monoformyl product is obtained in the following manner:

1 g. of diformyl product is stirred with 200 mg. potassium carbonate in methanol (25 ml.) for two hours at 0° C. The solvent is then evaporated in vacuo and the residue suspended in ether and filtered. The filtrate is concentraated and the residue partitioned between ether and water. The organic layer is separated, the aqueous phase acidified with 10% hydrochloric acid and extracted with ether. The combined ether extracts are washed successively with saturated sodium bicarbonate and brine, and then dried (MgSO$_4$), filtered and concentrated to yield additional monoformyl product.

The monoformyl derivative has the following NMR spectrum:

$^1$H NMR (60 MHz) $\delta_{CDCl_3}^{TMS}$ (ppm): 12.73 (S, 1H, ArOH), 8.87 (S, 1H, N—CHO), 6.12 (S, 2H, Aromatic), 4.78–5.50 (M, 1H, N—CH), 4.11–4.72 (M, 1H, —O—CH), 2.21 (S, 3H, CH$_3$—C(=O)—), 0.63–3.12 (M, 22H, remaining hydrogens).

Similarly, the following compounds are prepared from appropriate reactants:

d,l-1-formyl-5-hydroxy-7-(2-heptyloxy)-4-oxo-3-(3-oxobutyl)-1,2,3,4-tetrahydroquinoline, an oil.

¹H NMR (60 MH₂) $\delta_{CDCl_3}^{TMS}$ (ppm): 12.8 (S, 1H, phenolic), 8.7 (S, 1H, N—CHO), 6.1 (S, 2H, aromatic), 4.1-4.6 (m, 1H, —O—CH), 4.1 (d, 2H, J=5H₂, —CH₂—), 2.3-3.0 (m, 3H, CH₂ and CH—C(=O)), 2.2 (S, 3H, —C(=O)—CH₃), 2.3-0.7 (remaining protons).

d,l-1-formyl-5-hydroxy-2-methyl-7-(5-phenyl-2-pentyloxy)-4-oxo-3-(3-oxobutyl)-1,2,3,4-tetrahydroquinoline.

¹H NMR (60 MH₂) $\delta_{CDCl_3}^{TMS}$ (ppm): 12.68 (S, 1H, —OH), 8.82 (b, s, 1H, —C(O)H), 7.20 (b, s, 5H, C₆H₅), 6.18 (b, s, 2H, aromatic), 4.78-5.34 (m, 1H, —N—CH), 4.18-4.68 (m, 1H, —O—CH), 2.17 (S, 3H, —C(O)CH₃), 1.30 (d, 3H, —O—C—CH₃), 1.12 (d, 3H, —N—C—CH₃), 1.4-3.1 (m, 11H, remaining H's).

d,l-1-formyl-5-hydroxy-7-(5-phenyl-2-pentyloxy)-4-oxo-3-(3-oxobutyl)-1,2,3,4-tetrahydroquinoline.

m/e - 423 (m⁺)

Also produced as by-product in each of these preparations is the corresponding 1,3-diformyl derivative.

EXAMPLE 28

Following the procedures of Examples 25 and 27, the 5-hydroxy-2-R₄-7-(Z-W)-4-oxo-1,2,3,4-tetrahydroquinolines of Examples 18, 20 and 23 are converted to compounds having the formula below wherein R₄, R₅, Z and W are as defined in Examples 18, 20 and 23. When R₆ of the tetrahydroquinoline reactants is hydrogen, it is converted to formyl (CHO).

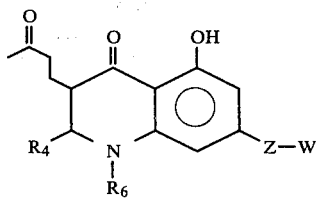

EXAMPLE 29 d,l-5,6,6a,7-Tetrahydro-1-hydroxy-6β-methyl-3-(5-phenyl-2-pentyloxy)benzo[c]quinolin-9(8H)-one A solution of d,l-1-formyl-5-hydroxy-2-methyl-7-(5-phenyl-2-pentyloxy)-4-oxo-3-(3-oxobutyl)-1,2,3,4-tetrahydroquinoline (174 g., 0.398 mole) in methanolic 2N KOH (5.9 liters) and methanol (5.9 liters) is stirred and heated at reflux overnight over a nitrogen atmosphere. To the cooled solution is added acetic acid (708 g.) dropwise with stirring over a 15 minute period. The resulting solution is concentrated by rotary evaporation (in vacuo, water aspirator) to a semisolid which is filtered and washed first with water to remove potassium acetate and then with ethyl acetate until all the black tar is removed. Yield=68 g. (44%) yellow solids, m.p. 188°-190° C. Recrystallization from hot ethyl acetate affords the pure product, m.p. 194°-195° C.

m/e - 391 (m⁺)

Analysis: Calc'd for C₂₅H₂₉O₃N: C, 76.09; H, 7.47; N, 3.58%. Found: C, 76.43; H, 7.48; N, 3.58%.

¹H NMR (60 MHz) $\delta^{TMS}$ (100 mg. dissolved in 0.3 ml. CD₃OD and 0.3 ml. CD₃S(O)CD₃) (ppm): 7.21 (s, 5H, aromatic), 5.80 (s, 2H, meta H's), 1.20 (d, 6H, CH₃—CHO and CH₃—CH—N).

From the mother liquors, a small amount of the corresponding axial methyl derivative is obtained upon evaporation. It is purified by column chromatography on silica gel using benzene/ether (1:1) as eluant. Evaporation of the eluate and recrystallization of the residue from ether/hexane (1:1) affords analytically pure material, m.p. 225°-228° C.

Its R_f value upon thin layer chromatography on silica gel using 2.5% methanol in ether as eluant and visualization with fast blue is 0.34. The 6β-methyl derivative exhibits R_f=0.41.

m/e - 391 (m⁺)

¹H NMR (60 MHz) $\delta^{TMS}$ (100 mg. dissolved in 0.3 ml. CD₃OD and 0.3 ml. CD₃S(O)CD₃) (ppm): 7.19 (s, 5H, aromatic), 5.75 (s, 2H, meta H's), 1.21 (d, 3H, CH₃—CHO—), and 0.95 (d, 3H, CH₃—CH—N).

Similar treatment of 22 g. of d,l-1-formyl-5-hydroxy-2-methyl-7-(4-phenylbutyloxy)-4-oxo-3-(3-oxobutyl)-1,2,3,4-tetrahydroquinolines gives 17.1 g. (87%) of d,l-5,6,6a,7-tetrahydro-1-hydroxy-6β-methyl-3-(4-phenylbutyloxy)benzo[c]quinolin-9(8H)-one, m.p. 222°-224° C. The analytical sample is obtained by recrystallization from methanol, m.p. 224°-225° C.

Calc'd for C₂₄H₂₇O₃N: C, 76.36; H, 7.21; N, 3.71%. Found: C, 76.03; H, 7.08; N, 3.68%.

¹H NMR (60 MHz) [1:1 mixture of (CD₃)₂SO and DC₃OD]: 1.24 (d, 3H, 6β—CH₃)

m/e - 377 (m⁺)

Evaporation of the mother liquor gives 2.8 g. (m.p. 185°-195° C.) of product shown by NMR to be a mixture of the 6β-methyl derivative (ca. 40%) and d,l-5,6,6a,7-tetrahydro-1-hydroxy-6α-methyl-3-(4-phenyl butyloxy)-benzo[c]quinoline-9(8H)-one.

¹H NMR (60 MHz) [1:1 mixture of (CD₃)₂SO and CD₃OD]: 1.24 (d, 1.2H, 6β—CH₃] and 0.95 (d, 1.8H, 6α—CH₃).

EXAMPLE 30 d,l-5,6,6a,7-Tetrahydro-1-hydroxy-6β-methyl-3-(2-hepthyloxy)benzo[c]quinolin-9(8H)-one A solution of d,l-1-formyl-5-hydroxy-2-methyl-7-(2-heptyloxy)-4-oxo-3-(3-oxobutyl)-1,2,3,4-tetrahydroquinoline (4.5 g., 11.5 mmol.) in methanol (150 ml.) is treated with 2N methanolic potassium hydroxide solution (150 ml.). The mixture is stirred for one hour at room temperature and then heated at reflux under a nitrogen atmosphere for 20 hours. The dark red mixture is allowed to cool to room temperature, neutralized with acetic acid and concentrated under pressure to about 100 ml. The concentrate is diluted with water (400 ml.) and the brown-red solid separated by filtration, washed with water and dried (−6 g.). It is triturated first in ether and then in methanol, filtered and dried (1.96 g.); m.p. 223°-229° C. Recrystallization from hot methanol affords crystals melting at 235°-237° C.

Analysis: Calc'd for C₂₁H₂₉O₃N: C, 73.43; H, 8.51; N, 4.08%. Found: C, 73.22; H, 8.30; N, 4.11%.

Additional material is recovered by evaporation of all mother liquors and by chloroform extraction of the aqueous solution from which the brown-red crude product is obtained and subsequent evaporation of the extract. The combined residues are purified by silica gel chromatography using ether as eluant.

In like manner, the following compounds are prepared from appropriate reactants:

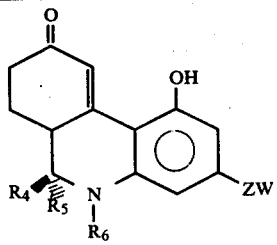

| ZW | R4 | R5 | R6 | m/e (m+) | (°C.) m.p. | Formula | Calc'd C, H, N | Found C, H, N |
|---|---|---|---|---|---|---|---|---|
| —O—CH(CH3)(CH2)3C6H5 | C2H5 | H | H | 405 | 155–6 | C26H31O3N | C - 77.00<br>H - 7.71<br>N - 3.45 | C - 76.86<br>H - 7.62<br>N - 3.45 |
| —O—CH(CH3)(CH2)3C6H5 | C6H13 | H | H | 461 | 139–141 | C30H39O3N | C - 78.05<br>H - 8.52<br>N - 3.03 | C - 78.16<br>H - 8.53<br>N - 3.09 |
| —O—CH(CH3)(CH2)3C6H5 | C5H11 | H | H | 447 | 150–3 | C29H37O3N | C - 77.81<br>H - 8.33<br>N - 3.13 | C - 77.73<br>H - 8.19<br>N - 3.13 |
| —O—CH(CH3)(CH2)3C6H5 | C4H9 | H | H | 433 | 160–2 | C28H35O3N | C - 77.56<br>H - 8.14<br>N - 3.23 | C - 77.28<br>H - 7.92<br>N - 3.18 |
| —O—CH(CH3)(CH2)3C6H5 | H | C4H9 | H | 433 | 95–98 | C28H35O3N | C - 77.56<br>H - 8.14<br>N - 3.23 | C - 77.86<br>H - 8.57<br>N - 3.17 |
| —O—CH(CH3)(CH2)3C6H5 | —(CH2)2—C6H5 | H | H | 481 | 200–201 | C32H35O3N | C - 79.80<br>H - 7.33<br>N - 2.91 | C - 79.64<br>H - 7.34<br>N - 2.93 |
| —O—CH(CH3)(CH2)3C6H5 | CH3 | H | H | 363 | 246–7 | C23H25O3N | C - 76.00<br>H - 6.93<br>N - 3.85 | C - 76.19<br>H - 7.14<br>N - 3.89 |
| —C(CH3)2—C6H3 | CH3 | H | H | 355 | 261–2 | C23H33O2N | C - 77.70<br>H - 9.36<br>N - 3.94 | C - 77.94<br>H - 9.21<br>N - 3.99 |
| —O(CH2)2C6H5 | CH3 | H | H | 349 | 248–250 | C22H23O3N | C - 75.62<br>H - 6.63<br>N - 4.01 | C - 75.26<br>H - 6.66<br>N - 3.93 |
| —OCH(CH3)(CH2)3C6H5 | H | H | H | 377 | 170–173 | C24H27O3N | C - 76.36<br>H - 7.21<br>N - 3.71 | C - 76.38<br>H - 7.21<br>N - 3.85 |
| —O—CH(CH3)(CH2)4CH3 | H | H | H | 329 | 208–209 | C20H27O3N | C - 71.92<br>H - 8.26<br>N - 4.25 | C - 72.92<br>H - 8.31<br>N - 4.42 |
| —O—CH(CH3)(CH2)3C6H5 | n-C3H7 | H | H | — | 164–166 | C27H33O3N | C - 77.29<br>H - 7.93<br>N - 3.34 | C - 76.97<br>H - 7.98<br>N - 3.41 |
| —O—CH(CH3)(CH2)3C6H5[a] | CH3 | H | H | 391 | 176–178 | C25H29O3N | C - 76.69<br>H - 7.47<br>N - 3.58 | C - 76.32<br>H - 7.36<br>N - 3.33 |
| —O—CH(CH3)(CH2)3C6H5[b] | CH3 | H | H | 391 | 172–174 | C25H29O3N | C - 76.69<br>H - 7.47<br>N - 3.58 | C - 76.40<br>H - 7.39<br>N - 3.51 |

[a] l-enantiomer; $[\alpha]_D^{25} = -416.0°$ (C = 0.33, CH3OH)
[b] d-enantiomer; $[\alpha]_D^{25} = +412.9°$ (C = 1.0, CH3OH)

EXAMPLE 31

The compounds of Example 28 are reacted according to the procedure of Example 30, to produce compounds having the formula shown below wherein R4, R5, R6, Z and W are as defined in Example 28.

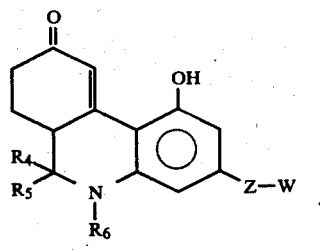

EXAMPLE 32 d,1-5,6,6a,7,10,10a-Hexahydro)benzo-6β-methyl-3-(2-heptyloxy)benzo[c]quinolin-9(8H)-one A suspension of d,1-5,6,6a,7-tetrahydro-1-hydroxy-6β-methyl-3-(2-heptyloxy)benzo[c]quinolin-9(8H)-one (1.0 g., 2.91 mmole) in tetrahydrofuran (20 ml.) is added dropwise via an addition funnel to a rapidly stirred solution of lithium (0.1 g.) in liquid ammonia (75 ml., distilled through potassium hydroxide pellets). The addition funnel is rinsed with tetrahydrofuran (10 ml.). The mixture is stirred for 10 minutes and then solid ammonium chloride is added to discharge the blue color. The excess ammonia is allowed to evaporate and the residue taken up in water (100 ml.) and ethyl acetate (50 ml.). The ethyl acetate layer is separated and the aqueous phase extracted with ethyl acetate (2×50 ml.).

The combined extracts are washed with brine, dried (MgSO4) and concentrated under reduced pressure to a brown semi-solid product (1.35 g.). Trituration of the semi-solid in pentane/ether (1:1) gives a light brown solid (0.884 g.); m.p. 130°–138° C.

The above procedure is repeated but using 1.84 g. (5.36 mmole) of the benzo[c]quinolin-9-one reactant, 0.184 g. of lithium, 140 ml. of liquid ammonia and 45 ml. of tetrahydrofuran. The residue (2.1 g.) remaining after evaporation of the ammonia is dissolved in benzene and charged to a chromatography column (3.8×61 cm) containing silica gel (250 g.). The column is eluted with a volume of degassed benzene equal to the volume of the column and then with 1700 ml. of degassed benzene-ether (9:1). Continued elution (1100 ml.) gives a brilliant red eluate which is concentrated to a light purple solid (580 mg.) under reduced pressure and triturated in benzene-ether (1:1) to give 370 mg. of solid; m.p. 154°–156° C. It is stored under nitrogen and in the dark. The isolated solids are mixtures of the cis- and trans-forms of the title product.

m/e - 345 (m+)

$^1$H NMR (100 MHz) $\delta_{CDCl_3}^{TMS}$ (ppm): 6.85 and 7.49 (1H, broad variable, OH), 5.67, 5.71, 5.85, 5.93 (d, J=2 Hz, 2H total, aromatic hydrogens for cis/trans mixture), 0.90 (t, 3H, terminal CH3), 1.12–4.43 (m, remaining H).

EXAMPLE 33

Following the procedure of Example 32, the compounds of Examples 30 and 31 are converted to products having the formula

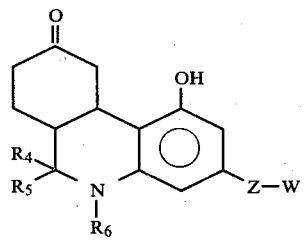

wherein R4, R5, R6, Z and W are as defined in Examples 30 and 31. Both cis- and trans-forms are produced.

EXAMPLE 34

Isomeric 5,6,6a,7,10,10a-Hexahydro-1-acetoxy-6β-methyl-3-(2-heptyloxy)benzo[c]quinolin-9(8H)-ones Pyridine (2.2 ml.) is added to a suspension of 5,6,6a,7,10,10a-hexahydro-1-hydroxy-6β-methyl-3-(2-heptyloxy)benzo[c]quinolin-9(8H)-one (222 mg., 0.642 mmole) in acetic anhydride (2.2 ml.) under a nitrogen atmosphere. The mixture is stirred for 1.5 hours at room temperature and is then poured onto ice (50 ml.). The gum which separates is extracted with ether (3×50 ml.) and the combined extracts washed first with water (4×50 ml.) and then with brine (1×60 ml.). The extract is dried (MgSO4) and evaporated under reduced pressure to a red oil (250 mg.).

The oil is dissolved in a minimum of hot ether and charged to a silica gel (45 g.) column, packed and eluted with pentane-ether (3:1). The column is eluted with pentane-ether (3:1, 200 ml.). Elution is continued and fractions (10 ml.) collected. Fractions 22–32 are combined and concentrated to a foam (113.5 mg.) which is crystallized from petroleum ether as white crystals; m.p. 112°–114° C.

Fractions 33–50 are combined and concentrated to a foam (89.7 mg.) which is recrystallized from petroleum ether as white crystals; m.p. 78°–82° C.

The products are the isomeric mono-acetylated compounds.

By means of this procedure the products of Example 33 are converted to their isomeric 1-acetoxy derivatives. Compounds having the formula below are thus prepared.

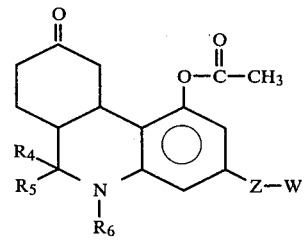

wherein R4, R5, R6, Z and W are as defined in Example 33.

Substitution of acetic anhydride by benzoic anhydride, propionic anhydride, butyric anhydride or valeric anhydride in this procedure affords the corresponding isomeric 1-benzoyloxy, 1-propionyloxy, 1-butyryloxy and 1-valeryloxy derivatives.

EXAMPLE 35 dl-trans-5,6,6aβ,7,10,10aα-hexahydro-1-acetoxy-5-acetyl-6β-methyl-3-(5-phenyl-2-pentyloxy)benzo[c]quinoline-9(8H)-one 3.49 g. (0.008 mole) of dl-trans-5,6,6aβ,7,10,10aα-hexahydro-1-acetoxy-6β-methyl-3-(5-phenyl-2-pentyloxy)-benzo[c]quinolin-9(8H)-one is dissolved in 20 ml. (alcohol-free) chloroform, the solution is cooled in an ice-water-bath then added 14 ml. pyridine (dried over potassium hydroxide pellets) followed by 0.95 ml. (0.013 mole) of acetyl chloride which is dissolved in 5 ml. chloroform. The homogeneous solution is then stirred at ambient temperature for 18 hours. The reaction mixture is poured onto 50 ml. ice-water and extracted twice with chloroform (25 ml. each). The combined organic layers are washed with 25 ml. sat. sodium bicarbonate, 25 ml. water, 25 ml. brine, dried over magnesium sulfate, filtered and evaporated to dryness under reduced pressure. Purification is achieved via chromatography (200 g. Brinkman slica gel, solvent: cyclohexane 3, ether 1) to afford 2.20 g. (83.8% yield) of the above title compound.

Analysis: Calc'd for $C_{29}H_{35}O_5N$: C, 72.90; H, 7.39; N, 2.80%. Found: C, 72.69; H, 7.48; N, 2.49%.

I.R. (KBr): 2.90μ (m), 3.38μ (s), 3.48μ (s), 5.62μ (s), 5.78μ (s), 6.00μ (s), 6.15μ (s), 6.30μ (s).

m/e - 477 (m+).

$^1$HNMR (60 MHz) $\delta_{CDCl_3}^{TMS}$: 7.20 (m, 5H, arom.), 6.53 (d, 1H, $C_{-2}$), 6.39 (d, 1H, $C_{-4}$), 4.71–4.08 (m, 2H, methines), 2.29 (s, 3H, acetate Me), 2.02 & 2.04 (2s, 3H, amide Me), 1.25 & 1.23 (2d, 3H, $C_{-6}$ Me), 1.12 (d, 3H, side chain Me), 3.20–1.36 (variable remaining protons).

In like manner, dl-cis-5,6,6aβ,7,10,10aβ-hexahydro-1-acetoxy-6β- methyl-3-(5-phenyl-2-pentyloxy)benzo[c]quinolin-9(8H)-one is converted to dl-cis-5,6,6aβ,7,10,-10aβ-hexahydro-1-acetoxy-5-acetyl-6β-methyl-3-(5-phenyl-2-pentyloxy)benzo[c]quinolin-9(8H)-one.

m.p. 125°–128° C., yield 82%.

Analysis: Calc'd for $C_{29}H_{35}O_5N$: C, 72.90; H, 7.39; N, 2.80%. Found: C, 72.80; H, 7.35; N, 2.70%.

$^1$HNMR (60 MHz) $\delta_{CDCl_3}{}^{TMS}$: 7.22 (m, 5H, arom.), 6.55 (2d, 2H, $C_2$ & $C_4$), 5.02–4.62 (m, 1H, $C_{-6}$ methine), 4.52–4.12 (m, 1H, side chain methine), 2.28 (s, 3H, acetate Me), 2.11 & 2.13 (3H, amide Me), 1.26 & 1.28 (3H, $C_{-6}$ Me), 1.22 (d, 3H, side chain Me), 3.42–1.65 (variable remaining protons).

I.R. (KBr): 2.95μ (w), 3.43μ (s), 5.65μ (s), 5.81μ (s), 6.02μ (s), 6.16μ (s), 6.32μ (s), 6.70μ (s).

m/e - 477 (m+).

EXAMPLE 36 d,l-5,6,6aβ,7,10,10aα-Hexahydro-1-acetoxy-6β-methyl-3-(2-heptyloxy)benzo[c]quinolin-9(8H)-one The procedure of Example 32 is repeated but using double the quantities of reactants. The product (2.22 g.) is then directly acetylated according to the procedure of Example 34 to give 2.35 g. of acetylated product. This product is triturated in pentane-ether (3:1) to a tan solid (905 mg.) which when recrystallized from ethanol gives 404 mg. of light tan crystals; m.p. 112°–113.5° C.

The mother liquors from which each of the above solids is separated are combined and concentrated. The residue is dissolved in a minimum of benzene-ether-methylene chloride (1:1:1) and charged to a silica gel (275 g.) column (packed and eluted with petroleum ether-ether [3:1]). The column is eluted first with 2 liters of petroleum ether-ether (3:1) followed by 1.5 liters of petroleum ether-ether (2:1) and 2 liters of petroleum ether-ether (1:1). Fractions 2–11 (50 ml. each) of eluate from the 1:1 solvent system are collected and concentrated under reduced pressure to a foam (496 mg.). Crystallization from petroleum ether affords white crystals; m.p. 100°–113° C. (410 mg.). Recrystallization from ethanol-water (1:1) gives d,l-trans-5,6,6aβ,7,10,-10aα-hexahydro-1-acetoxy-6β-methyl-3-(2-heptyloxy)-benzo[c]quinolin-9(8H)-one melting at 111°–112° C.

m/e - 387 (m+)

Analysis: Calc'd for $C_{23}H_{33}O_4N$: C, 71.29; H, 8.58; N, 3.61%. Found: C, 70.95; H, 8.64; N, 3.58%.

Fractions 12–18 and 19–27 (50 ml. each) are collected and concentrated to afford 273 mg. and 208 mg., respectively, of acetylated product. Crystallization of the residue from fractions 19–27 from petroleum ether gives white crystals (119 mg.); m.p. 84°–88° C. Recrystallization from ethyl acetate-hexane (1:10) gives d,l-cis-5,6,6aβ,7,10,10aβ-hexahydro-1-acetoxy-3-(2-heptyloxy)-6β-methyl-benzo[c]quinolin-9(8H)-one, m.p. 84°–86° C.

Analysis: Calc'd for $C_{23}H_{33}O_4N$: C, 71.29; H, 8.58; N, 3.61%. Found: C, 71.05; H, 8.48; N, 3.56%.

Similarly, the following compounds are prepared from appropriate reactants:

d,l-trans-5,6,6aβ,7,10,10aα-hexahydro-1-acetoxy-6β-methyl-3-(5-phenyl-2-pentyloxy)benzo[c]quinolin-9(8H)-one, m.p. 80°–82° C.

m/e - 435 (m+)

Analysis: Calc'd for $C_{27}H_{33}O_4N$: C, 74.45; H, 7.64; N, 3.22%. Found: C, 74.43; H, 7.73; N, 3.28%.

d,l-cis-5,6,6aβ,7,10,10aβ-hexahydro-1-acetoxy-6β-methyl-3-(5-phenyl-2-pentyloxy)benzo[c]quinolin-9(8H)-one, m.p. 172°–176° C. as the hydrochloride salt from acetone-ether (1:1).

Analysis: Calc'd for $C_{27}H_{33}O_4N\cdot HCl$: C, 68.71; H, 7.26; N, 2.97%. Found: C, 68.86; H, 7.16; N, 2.97%.

d,l-trans-5,6,6aβ,7,10,10aα-hexahydro-1-acetoxy-3-(5-phenyl-2-pentyl-oxy)-6β-propylbenzo[c]quinolin-9(8H)-one; m.p. 79°–80° C.

m/e - 463 (m+)

d,l-cis-5,6,6aβ,7,10,10aβ-hexahydro-1-acetoxy-3-(5-phenyl-2-pentyloxy)-6β-propylbenzo[c]quinolin-9(8H)-one; m.p. 144°–146° C., as the HCl salt.

m/e - 463 (m+)

d-cis-5,6,6aβ,7,10,10aβ-hexahydro-1-acetoxy-3-(5-phenyl-2-pentyloxy)-6β-methylbenzo[c]quinolin-9(8H)-one; m.p. 90°–94° C. (dec.) as the hydrochloride salt.

$[\alpha]_D{}^{25} = +22.8°$ (c=0.31, $CH_3OH$)

m/e - 435 (m+)

Analysis: Calc'd for $C_{27}H_{33}O_4N\cdot HCl$: C, 68.71; H, 7.26; N, 2.97%. Found: C, 69.24; H, 7.30; N, 3.01%.

d-trans-5,6,6aβ,7,10,10aβ-hexahydro-1-acetoxy-3-(5-phenyl-2-pentyloxy)-6β-methylbenzo[c]quinolin-9(8H)-one; m.p. 90°–95° C. (dec.) as the hydrochloride salt.

$[\alpha]_D{}^{25} = +78.46°$ (c=0.13, $CH_3OH$).

m/e - 435 (m+)

Analysis: Calc'd for $C_{27}H_{33}O_4N\cdot HCl$: C, 68.71; H, 7.26; N, 2.97%. Found: C, 70.20; H, 7.23; N, 3.07%.

l-cis-5,6,6aβ,7,10,10aβ-hexahydro-1-acetoxy-3-(5-phenyl-2-pentyloxy)-6β-methylbenzo[c]quinolin-9(8H)-one; m.p. 90°–92° C. as the hydrochloride.

$[\alpha]_D{}^{25} = -20.5°$ (c=0.19, $CH_3OH$)

m/e - 435 (m+)

Analysis: Calc'd for $C_{27}H_{33}O_4N\cdot HCl$: C, 68.71; H, 7.26; N, 2.97%. Found: C, 68.92; H, 7.23; N, 3.09%.

l-trans-5,6,6aβ,7,10,10aβ-hexahydro-1-acetoxy-3-(5-phenyl-2-pentyloxy)-6β-methylbenzo[c]quinolin-9(8H)-one; m.p. 92°–96° C. as the hydrochloride $[\alpha]_D{}^{25} = -79.0°$ (c=0.10, $CH_3OH$)

m/e - 435 (m+)

Analysis: Calc'd for $C_{27}H_{33}O_4N\cdot HCl$: C, 68.71; H, 7.26; N, 2.97%. Found: C, 68.67; H, 7.23; N, 3.02%.

EXAMPLE 37 d,l-5,6,6a,7,10,10a-Hexahydro-1-acetoxy-6β-methyl-3-(5-phenyl-2-pentyloxy)benzo[c]quinolin-9(8H)-one, trans- and cis-isomers Ammonia (1150 ml.) is condensed directly into a flame-dried 3 liter/3 neck flask (under a nitrogen atmosphere) equipped with mechanical stirrer, a 500 ml. dropping funnel and solid $CO_2$/acetone cooling (~ −75° C.). Lithium wire (2.2 g., cut into ¼″ pieces) is added and a characteristic blue color forms immediately. To the stirred blue solution at −78° C. is added d,l-5,6,6a,7-tetrahydro-1-hydroxy-6β-methyl-3-(5-phenyl-2-pentyloxy)benzo[c]quinolin-9(8H)-one (21.5 g., 0.055 mole) dissolved in tetrahydrofuran (250 ml.) dropwise over a 10 minute period. After an additional 5 minutes of stirring at −78° C., the reaction mixture is quenched by the addition of dry ammonium chloride (20 g.). The cooling is then discontinued and the reaction mixture warmed slowly on a steam bath to evaporate the ammonia. When almost dry, ethyl acetate (2 liters) and water (1 liter) are added and the mixture stirred for 10 minutes. The layers are then separated and the aqueous phase is extracted once more with ethyl acetate (500 ml.). The combined organic extracts are washed once with water (1 liter), dried ($MgSO_4$) and concentrated to a brown semi-solid (~28 g.). This residue is immediately dissolved in methylene chloride (200 ml.), 4-dimethylaminopyridine (7.5 g., 0.061 mole) and triethylamine (6.1 g., 0.061 mole) added and the stirred solution cooled to 0° C. (ice/water cooling) under a nitrogen atmosphere. Acetic anhydride (6.1 g., 0.061 mole) is then added dropwise over 5 minutes with good stirring. After an additional 30 minutes of stirring at 0° C., the reaction mixture is diluted with ethyl acetate (2 liters) and water (1 liter) and stirred for 10 minutes. The aqueous is extracted once more with water and the combined organics washed successively with water (4×1 liter), saturated sodium bicarbonate (1×1 liter), brine (1×1 liter), dried (MgSO4) and concentrated to a light brown oil (~27 g.). The residue is chromatographed on 1.8 kg. of silica gel using benzene 15/ethyl acetate as the eluting solvent. One liter fractions are collected.

After elution of less polar impurities, fractions 16–20 are combined and evaporated to a residue which is crystallized from ether/petroleum ether to yield 5.6 g. (23.4%) of the trans-isomer of the title product. Fractions 21–27 are combined to give 7.6 g. (31.8%) of a mixture of the trans- and cis-isomers, and fractions 28–32 are combined to give 2.5 g. (10.4%) of the cis-isomer of the title product.

The trans-isomer exhibits the following characteristics:

m/e - 435 (m+)

$^1$H NMR (60 MHz) $\delta_{CDCl_3}^{TMS}$ (ppm): 7.24 (s, 5H, aromatic), 5.97 (s, 2H, meta H's), 2.28 (s, 3H, CH$_3$—COO), 1.23 (d, 3H, CH$_3$—CH—O—), 1.20 (d, 3H, CH$_3$—CH—N), 1.3–4.5 (m, 17H, remaining protons).

M.P. - 81°–83° C.

Analysis: Calc'd for C$_{27}$H$_{33}$O$_4$N: C, 74.45; H, 7.64; N, 3.22%. Found: C, 74.15; H, 7.68; N, 3.18%.

The cis-isomer has the following characteristics:

m/e - 435 (m+)

M.P. of HCl salt - 172°–176° C. (dec.) (from acetone-ether).

Analysis: Calc'd for C$_{27}$H$_{33}$O$_4$N.HCl: C, 68.71; H, 7.26; N, 2.97%. Found: C, 68.86; H, 7.16; N, 2.97%.

EXAMPLE 38 d,l-5,6,6a,7,10,10a-Hexahydro-1-acetoxy-6β-methyl-3-(4-phenylbutyloxy)benzo[c]quinolin-9(8H)-one, trans- and cis-isomers Following the procedure of Example 36, d,l-5,6,6a,7-tetrahydro-1-hydroxy-6β-methyl-3-(4-phenylbutyloxy)benzo[c]quinolin-9(8H)-one is first reduced with lithium and ammonia and then acylated to yield the desired hexahydro isomers. Separation by column chromatography on silica gel using ether as eluant provides first d,l-trans-5,6,6aβ,7,10,10aα-hexahydro-1-acetoxy-6β-methyl-3-(4-phenylbutyloxy)benzo[c]quinolin-9(8H)-one, m.p. 155°–156° C. after recrystallization from ethyl acetate/pentane (1:5).

Analysis: Calc'd for C$_{26}$H$_{31}$O$_4$N: C, 74.08; H, 7.41; N, 3.32%. Found: C, 74.00; H, 7.47; N, 3.22%.

m/e - 421 (m+)

Further purification of later fractions by additional column chromatography on silica gel using cyclohexane-ether (1:1) as eluant yields the isomeric d,l-cis-5,6,6aβ,7,10,10aβ-hexahydro-1-acetoxy-6β-methyl-3-(4-phenylbutyloxy)benzo[c]quinolin-9(8H)-one, m.p. 95°–96° C. after recrystallization from ethyl acetate/hexane (1:5).

m/e - 421 (m+)

Analysis: Calc'd for C$_{26}$H$_{31}$O$_4$N: C, 74.08; H, 7.41; N, 3.32%. Found: C, 73.95; H, 7.51; N, 3.31%.

EXAMPLE 39 d,l-5,6,6aβ,7,10,10a-hexahydro-1-acetoxy-3-(2-heptyloxy)benzo[c]quinolin-9(8H)-one A solution of d,l-5,6,6a,7-tetrahydro-1-hydroxy-3-(2-heptyloxy)benzo[c]quinolin-9(8H)-one (9.0 g.) in tetrahydrofuran (100 ml.) is added dropwise to a rapidly stirred solution of lithium (0.1 g.) in liquid ammonia (750 ml.). An additional 0.1 g. of lithium is added portionwise during the addition to insure a blue color. The mixture is stirred for 10 minutes and then the blue color discharged by addition of excess ammonium chloride. The excess ammonia is allowed to evaporate and the residue is taken up in a mixture of water and ethyl acetate. The organic layer is separated and the aqueous phase extracted twice more with ethyl acetate. The combined extracts are washed with water, brine, dried (MgSO4) and evaporated to give 8.45 g. of crude product as a brown solid.

The crude product (8.0 g.) is suspended in methylene chloride (48 ml.) at 0° C. and treated with N,N-dimethyl-4-aminopyridine (3.24 g.) and triethylamine (3.72 ml.) Acetic anhydride (2.52 ml.) is then added to the mixture which is then stirred for 30 minutes as 0° C. It is diluted with methylene chloride (300 ml.) and the methylene chloride layer separated, washed with water (3×150 ml.), saturated sodium bicarbonate (1×100 ml.), brine (1×100 ml.), and dried (MgSO4). Evaporation of the methylene chloride gives 13.7 g. of dark oil which is chromatographed on a silica gel (450 g.) column. The column is eluted sequentially with ether-hexane (1:1), ether-hexane (2:1) and ether. Fractions of 18 ml. each are collected. Fractions 176–224 are combined and concentrated to an oil which is crystallized from hexane to give 3.24 g. (32%) yield of the trans-isomer of the title compound as light yellow crystals; m.p. 65.5°–68° C.

m/e-373 (m+)

IR (KBr): 5.82 (ketone C═O), 5.75 (ester C═O), 295 (NH) μ.

Fractions 246–290 are combined and concentrated to give 0.55 g. (5%) of crude cis-isomer of the title compound as an oil. It is purified further by column chromatography as described above to give the pure cis-isomer as an oil.

m/e-373 (m+)

IR (CHCl$_3$): 5.82 (ketone C═O), 5.67 (ester C═O), 2.92 (NH) μ.

Analysis: Calc'd for C$_{22}$H$_{31}$O$_4$N: C, 70.75; H, 8.37; N, 3.75%. Found: C, 70.90; H, 8.54; N, 3.79%.

Fractions 225–245 are combined and evaporated to give 2.69 g (26%) of a mixture of cis- and trans-isomers which are separated by the procedure described above.

The following compounds are similarly prepared from d,l-5,6,6a, 7-tetrahydro-1-hydroxy-3-(5-phenyl-2-pentyloxy)benzo[c]quinolin-9(8H)-one:

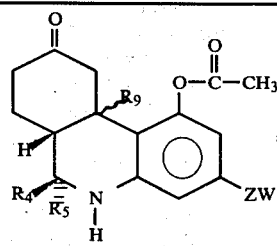

| ZW | R₄ | R₅ | R₉ | (°C.) m.p. | m/e (m+) | Formula | Calc'd C, H, N | Found C, H, N |
|---|---|---|---|---|---|---|---|---|
| —O—CH(CH₃)(CH₂)₃C₆H₅ | C₂H₅ | H | ◂H | 125–130 | 449 | C₂₈H₃₅O₄N·HCl | C-69.18<br>H- 7.47<br>N- 2.88 | C-68.89<br>H- 7.45<br>N- 2.90 |
| —O—CH(CH₃)(CH₂)₃C₆H₅ | C₂H₅ | H | ⦀H | 153–155 | 449 | C₂₈H₃₅O₄N·HCl | C-69.18<br>H- 7.47<br>N- 2.88 | C-69.18<br>H- 7.32<br>N- 2.93 |
| —O—CH(CH₃)(CH₂)₃C₆H₅ | C₆H₁₃ | ⦀H | ⦀H | 103–104 | 505 | C₃₂H₄₃O₄N | C-76.00<br>H- 8.57<br>N- 2.77 | C-75.88<br>H- 8.47<br>N- 2.84 |
| —O—CH(CH₃)(CH₂)₃C₆H₅ | C₆H₁₃ | H | ◂H | 100–101 | 505 | C₃₂H₄₃O₄N | C-76.00<br>H- 8.57<br>N- 2.77 | C-75.62<br>H- 8.39<br>N- 2.63 |
| —O—CH(CH₃)(CH₂)₃C₆H₅ | CH₂CH₂<br>\|<br>C₆H₅ | H | ⦀H | 100–105 | 525 | C₃₄H₃₉O₄N | C-77.68<br>H- 7.48<br>N- 2.66 | C-77.54<br>H- 7.40<br>N- 2.65 |
| —O—CH(CH₃)(CH₂)₃C₆H₅ | CH₂CH₂<br>\|<br>C₆H₅ | H | ◂H | 118–119 | 525 | C₃₄H₃₉O₄N | C-77.68<br>H- 7.48<br>N- 2.66 | C-77.62<br>H- 7.61<br>N- 2.64 |
| —O—CH(CH₃)(CH₂)₃C₆H₅ | C₅H₁₁ | H | ⦀H | 99–100 | 491 | C₃₁H₄₁O₄N | C-75.73<br>H- 8.41<br>N- 2.85 | C-75.82<br>H- 8.31<br>N- 3.12 |
| —O—CH(CH₃)(CH₂)₃C₆H₅ | C₅H₁₁ | H | ◂H | 129–130 | 491 | C₃₁H₄₁O₄N | C-75.73<br>H- 8.41<br>N- 2.85 | C-75.68<br>H- 8.26<br>N- 2.95 |
| —O—CH(CH₃)(CH₂)₃C₆H₅ | C₄H₉ | H | ⦀H | 86–88 | 477 | C₃₀H₃₉O₄N | C-75.44<br>H- 8.23<br>N- 2.93 | C-75.50<br>H- 8.12<br>N- 2.91 |
| —O—CH(CH₃)(CH₂)₃C₆H₅ | C₄H₉ | H | ◂H | 104–106 | 477 | C₃₀H₃₉O₄N | C-75.44<br>H- 8.23<br>N- 2.93 | C-75.76<br>H- 8.26<br>N- 3.02 |
| —O(CH₂)₃C₆H₅ | CH₃ | H | ⦀H | 132–134 | 407 | C₂₅H₂₉O₄N | C-73.68<br>H- 7.17<br>N- 3.44 | C-73.93<br>H- 7.05<br>N- 3.41 |
| —O—(CH₂)₃C₆H₅ | CH₃ | H | ⦀H | 110–112 | 407 | C₂₅H₂₉O₄N | C-73.68<br>H- 7.17<br>N- 3.44 | C-73.45<br>H- 7.23<br>N- 3.39 |
| —O—CH(CH₃)(CH₂)₃C₆H₅ | H | H | ◂H | oil | 421 | C₂₆H₃₁O₄N | C-74.08<br>H- 7.41<br>N- 3.32 | C-74.16<br>H- 7.59<br>N- 3.20 |
| —O—CH(CH₃)(CH₂)₃C₆H₅ | H | H | ⦀H | oil | 421 | C₂₆H₃₁O₄N | C-74.08<br>H- 7.41<br>N- 3.32 | C-74.04<br>H- 7.49<br>N- 3.54 |
| —O—CH(CH₃)(CH₂)₃C₆H₅ | H | CH₃◂H | | 107–110⁽ᵃ⁾ | 435 | C₂₇H₃₃O₄N·HCl | C-68.71<br>H- 7.26<br>N- 2.96 | C-68.92<br>H- 7.17<br>N- 2.86 |
| —O—CH(CH₃)(CH₂)₃C₆H₅ | H | CH₃ | ⦀H | 94–102⁽ᵇ⁾ | 435 | C₂₇H₃₃O₄N·HCl | C-68.71<br>H- 7.26<br>N- 2.96 | C-68.71<br>H- 7.26<br>N- 3.12 |

⁽ᵃ⁾ and ⁽ᵇ⁾Transformed to hydrochloride salts by general procedure of salt formation. On thin-layer chromatography in benzene/ether (1:1) R_f of ⁽ᵃ⁾ = 0.74 and R_f of ⁽ᵇ⁾ = 0.72.

EXAMPLE 40 d,l-Trans-5,6,6aβ,7,8,9,10aα-octahydro-1-acetoxy-9-hydroxy-6β-methyl-3-(2-heptyloxy)benzo[c]quinoline To a stirred suspension of 150 mg. (0.39 mmole) d,l-trans-5,6,6aβ,7,10,10aα-hexahydro-1-acetoxy-6β-methyl-3-(2-heptyloxy)-benzo[c]quinolin-9(8H)-one in ethanol (10 ml.) at 0° C. is added 40 mg. of sodium borohydride. After 0.5 hr., the reaction mixture is poured into a mixture of ice cold 5% acetic acid (50 ml.) and ether (75 ml.). After separation of the ether layer, the aqueous phase is extracted further with ether (2×50 ml.). The combined ether extracts are washed successively with water (2×50 ml.), saturated sodium bicarbonate (1×50 ml.), brine (1×75 ml.), dried (MgSO₄), filtered and concentrated under reduced pressure to yield 156 mg. of a white foam containing a mixture of the axial (minor amount) and equatorial (major amount) alcohols of d,l-trans-5,6,6aβ,7,8,9,10,10aα-octahydro-1-acetoxy-9-hydroxy-6β-methyl-3-(2-heptyloxy)benzo[c]quinoline.
m/e-389 (m+)

IR (CHCl₃) 5.72μ(ester carbonyl).

NMR (60 MHz, $\delta_{CDCl_3}^{TMS}$)-showed a characteristic singlet at 2.28 ppm for the acetate methyl.

The major and minor isomers are separated in the following manner: 180 mg. of the alcohols of d,l-trans-5,6,6aβ,7,8,9,10,10aα-octahydro-1-acetoxy-9-hydroxy-6β-methyl-3-(2-heptyloxy)-benzo[c]quinoline are charged to a column containing 15 grams of silica gel and eluted with a solvent mixture of 3 parts benzene to 1 part ether. 15 ml. Fractions are collected. Fractions 6–8 are combined and concentrated under reduced pressure to yield 13 mg. of d,l-trans-5,6,6aβ,7,8,9,10,10aα-octahydro-1-acetoxy-9α-hydroxy-6β-methyl-3-(2-heptyloxy)benzo[c]quinoline.

Fractions 11–16 are combined and concentrated to yield 83 mg. of d,l-trans-5,6,6aβ,7,8,9,10,10aα-octahydro-1-acetoxy-9β-hydroxy-6β-methyl-3-(2-heptyloxy)-benzo[c]quinoline.

Other compounds prepared from appropriate reactants by the above procedure include the following:

d,l-trans-5,6,6aβ,7,8,9,10,10aα-octahydro-1-acetoxy-9-hydroxy-6β-methyl-3-(5-phenyl-2-pentyloxy)benzo[c]quinoline.

m/e - 437 (m+)

IR (CHCl₃) - 5.70μ (ester carbonyl)

Conversion to the hydrochloride yielded a solid (m.p. 188°–190° C.). Recrystallization from acetone/methanol/ether (25:1:100) affords an analytical sample of the 9β-alcohol, m.p. 193°–194° C.

Analysis: Calc'd for C₂₇H₃₅O₄N.HCl: C, 68.42; H, 7.66; N, 2.96%. Found: C, 68.48; H, 7.70; N, 2.89%.

Conversion to the methanesulfonate (with methanesulfonic acid in dichloromethane) gives a solid which is recrystallized from ethyl acetate to yield white crystals, m.p. 110°–114° C.

IR (CHCl₃): 2.95, 3.70, 3.95, 5.60, 6.06, 6.19 and 6.27μ.

Analysis: Calc'd for C₂₇H₃₅O₄N.CH₄O₃S: C, 63.02; H, 7.37; N, 2.63%. Found: C, 62.90; H, 7.31; N, 2.74%.

d,l-cis-5,6,6aβ,7,8,9,10,10aβ-octahydro-1-acetoxy-9-hydroxy-6β-methyl-3-(5-phenyl-2-pentyloxy)benzo[c]quinoline.

m/e - 437 (m+)

IR (CHCL₃)-5.71 μ (ester carbonyl)

l-trans-5,6,6aβ,7,8,9,10,10aα-octahydro-1-acetoxy-9β-hydroxy-6β-methyl-3-(5-phenyl-2-pentyloxy)benzo[c]quinoline; m.p. 120°–125° C. (dec.) as the hydrochloride salt.

$[\alpha]_D^{25} = -98.57°$ (c=0.351, CH₃OH)

m/e - 437 (m+)

Analysis: Calc'd for C₂₇H₃₅O₄N.HCl: C, 68.42; H, 7.66; N, 2.96%. Found: C, 68.24; H, 7.68; N, 3.00%.

d-trans-5,6,6aβ,7,8, 9, 10,10aα-octahydro-1-acetoxy-9β-hydroxy-6β-methyl-3-(5-phenyl-2-pentyloxy)benzo[c]quinoline; m.p. 120°–125° C. (dec.) as the hydrochloride salt.

$[\alpha]_D^{25} = +99.33°$ (c=0.30, CH₃OH)

m/e - 437 (m+)

Analysis: Calc'd for C₂₇H₃₅O₄N.HCl: C, 68.42; H, 7.66; N, 2.96%. Found: C, 68.41; H, 7.54; N, 2.95%.

In like manner, the compounds tabulated below are prepared from appropriate reactants.

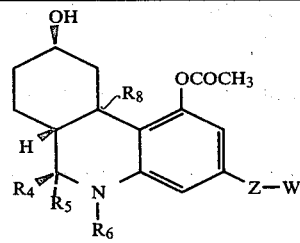

| Z—W | R₄ | R₅ | R₆ | R₈ | Salt* | M.P. (°C.) | m/e (m+) | Formula | Calc'd C | Calc'd H | Calc'd N | Found C | Found H | Found N |
|---|---|---|---|---|---|---|---|---|---|---|---|---|---|---|
| 5-phenyl-2-pentyloxy | H | CH₃ | H | ⫼H | HCl | 110–130 | 437 | C₂₇H₃₅O₄N.HCl | 68.42 | 7.66 | 2.96 | 68.45 | 7.60 | 3.08 |
| 5-phenyl-2-pentyloxy | H | CH₃ | H | ◂H | oil | | 437 | | | | | | | |
| 5-phenyl-2-pentyloxy | CH₃ | H | CH₃ | ◂H | HCl | 78–82 | 451 | | | | | | | |
| 5-phenyl-2-pentyloxy | CH₃ | H | CH₃ | ⫼H | HCl | 163.5–165 | 451 | | | | | | | |
| 4-phenylbutoxy | CH₃ | H | CH₃ | ⫼H | | 134–135 | 437 | C₂₇H₃₅O₄N | 74.11 | 8.06 | 3.20 | 73.59 | 8.07 | 3.24 |
| 4-phenylbutoxy | CH₃ | H | H | ⫼H | HCl | 187–188 | 423 | C₂₆H₃₃O₄N.HCl | 67.89 | 7.45 | 3.04 | 67.85 | 7.37 | 2.97 |
| 2-heptyloxy | H | H | H | ⫼H | oil | | 375 | C₂₁H₂₂O₄N | 70.37 | 8.86 | 3.73 | 69.85 | 8.87 | 3.63 |
| 2-heptyloxy | H | H | H | ◂H | oil | | 375 | C₂₂H₃₃O₄N | 70.37 | 8.86 | 3.73 | 70.55 | 8.70 | 3.71 |
| 5-phenyl-2-pentyloxy | H | H | H | ◂H | oil | | 423 | | | | | | | |
| 5-phenyl-2-pentyloxy | C₃H₇ | H | H | ◂H | HCl | 205–206 | 465 | | | | | | | |

*Prepared by addition of HCl gas to ether solution of base form.

EXAMPLE 41 d,l-trans-5,6,6aβ,7,8,9,10,10aα-octahydro-1-acetoxy-9β-hydroxy-6β-methyl-3-(5-phenyl-2-pentyloxy)benzo[c]quinoline Method A Sodium borohydride (7.57 g., 0.20 mole) is added to methanol (200 ml.) under a nitrogen atmosphere and cooled in an acetone/dry ice bath to about −75° C. The mixture is stirred for about 20 minutes to dissolve most, if not all, the sodium borohydride. A solution of d,l-trans-5,6,6aβ,7,10,10aα-hexahydro-1-acetoxy-6β-methyl-3-(5-phenyl-2-pentyloxy)benzo[c]quinolin-9(8H)-one (8.71 g., 0.02 mole) in tetrahydrofuran (88 ml.) is cooled to about −50° C. and then added dropwise over a 5–10 minute period to the sodium borohydride solution. The reaction mixture is stirred at about −70° C. for 30 minutes and is then poured onto a mixture of water (1000 ml.) containing ammonium chloride (45 g., 0.80 mole), crushed ice (250 ml.) and ethyl acetate (250 ml.). The layers are separated and the aqueous extracted with ethyl acetate (3×200 ml.). The combined extracts are washed with water (1×100 ml.) and dried (MgSO₄). The dried extract is cooled to about 5° C. A solution of ethyl acetate (15 ml.)/HCl, 1.5N (0.025 mole) is then added dropwise over a 15 minute period. Upon stirring the mixture at 0°-5° C., the hydrochloride salt of the title product precipitates. The mixture is stirred for a half-hour, filtered and the salt dried at 25° C./0.055 mm. to give 6.378 g. (67.3%) of product, m.p. 195°-198° C. (dec.).

The following compounds are prepared from appropriate reactants in like manner.

title product as a white solid. It is filtered, washed with ethyl acetate, and dried.

Similarly prepared are the following compounds:

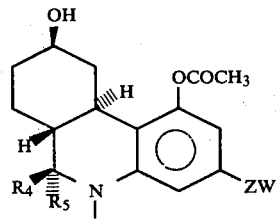

| ZW | $R_4$ | $R_5$ | $R_6$ | (°C.) m.p. | m/e (m+) | Formula | Calc'd C, H, N | Found C, H, N |
|---|---|---|---|---|---|---|---|---|
| —O—CH(CH$_3$)(CH$_2$)$_3$C$_6$H$_5$ | C$_5$H$_{11}$ | H | H | 209–210 | 493 | C$_{34}$H$_{41}$O$_4$H.HCl | C-70.23<br>H- 8.37<br>N- 2.64 | C-70.04<br>H- 8.16<br>N- 2.59 |
| —O—CH(CH$_3$)(CH$_2$)$_3$C$_6$H$_5$ | C$_4$H$_9$ | H | H | 159–160 | 479 | C$_{30}$H$_{41}$O$_4$N.HCl | C-69.82<br>H- 8.20<br>N- 2.71 | C-70.05<br>H- 8.44<br>N- 2.66 |
| —O—CH(CH$_3$)(CH$_2$)$_3$C$_6$H$_5$ | CH$_3$ | H | H | 130–138 | 409 | C$_{25}$H$_{31}$O$_4$N.HCl | C-67.33<br>H- 7.23<br>N- 3.14 | C-67.60<br>H- 7.22<br>N- 3.06 |
| —O—CH(CH$_3$)(CH$_2$)$_3$C$_6$H$_5$ | (CH$_2$)$_2$C$_6$H$_5$ | H | H | 199–200 | 527 | C$_{34}$H$_{41}$O$_4$N.HCl | C-72.39<br>H- 7.51<br>N- 2.48 | C-72.33<br>H- 7.38<br>N- 2.50 |
| —O—CH(CH$_3$)(CH$_2$)$_3$C$_6$H$_5$ | C$_3$H$_7$ | H | H | 193–195 | 465 | C$_{29}$H$_{39}$O$_4$N.HCl | C-69.35<br>H- 8.03<br>N- 2.79 | C-69.89<br>H- 8.36<br>N- 3.05 |
| —O—CH(CH$_3$)(CH$_2$)$_3$C$_6$H$_5$ | C$_2$H$_5$ | H | H | 154–157 | 451 | C$_{28}$H$_{37}$O$_4$N.HCl | C-68.88<br>H- 7.85<br>N- 2.87 | C-68.58<br>H- 7.52<br>N- 2.79 |
| —O—CH(CH$_3$)(CH$_2$)$_3$C$_6$H$_5$ | C$_6$H$_{13}$ | H | H | 196–199 | 507 | C$_{32}$H$_{45}$O$_4$N.HCl | C-70.61<br>H- 8.53<br>N- 2.58 | C-69.75<br>H- 8.19<br>N- 2.51 |
| —O—CH(CH$_3$)(CH$_2$)$_3$C$_6$H$_5$ | C$_3$H$_7$ | H | CH$_3$ | 154–156 | 479 | C$_{30}$H$_{41}$O$_4$N.HCl | C-69.79<br>H- 8.21<br>N- 2.72 | C-69.76<br>H- 8.16<br>N- 2.74 |
| —O—(CH$_2$)$_2$C$_6$H$_5$ | CH$_3$ | H | H | 210–212 (dec.) | 395 | C$_{24}$H$_{29}$O$_4$N.HCl | C-66.73<br>H- 7.00<br>N- 3.24 | C-66.37<br>H- 6.93<br>N- 3.18 |
| C(CH$_3$)$_2$—(CH$_2$)$_5$CH$_3$ | CH$_3$ | H | H | 114–115 | 401 | C$_{25}$H$_{39}$O$_3$N | C-74.77<br>H- 9.79<br>N- 3.49 | C-74.47<br>H- 9.24<br>N- 3.24 |

(a) = cis 6a,10a

Alternatively, the title compound is prepared by the following procedure (Method B).

d,l-trans-5,6,6aβ,7,8,9,10,10aα-octahydro-1-acetoxy-9β-hydroxy-6β-methyl-3-(5-phenyl-2-pentyloxy)benzo[c]quinoline A heterogeneous mixture of d,l-5,6,6a,7-tetrahydro-1-acetoxy-6β-methyl-3-(5-phenyl-2-pentyloxy)benzo[c]quinolin-9(8H)-one (3.0 g., 7 mmole) and palladium-on-carbon (5%, 3.0 g.) in methanol (30 ml.) is hydrogenated at room temperature in a Parr apparatus under 50 p.s.i. hydrogen for three hours. The catalyst is then filtered and the methanol filtrate evaporated under reduced pressure to give the title product.

The product is taken up in ethyl acetate (300 ml.) and the resulting solution cooled to 0° C. An excess of a saturated solution of hydrogen chloride in ethyl acetate is then added to precipitate the hydrochloride salt of the

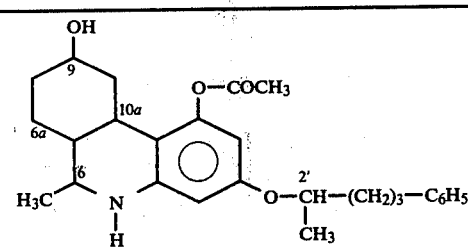

.HCl

| Configuration | (°C.) m.p. | m/e$^{(b)}$ (m+) | Analysis$^{(c)}$ | | | |
|---|---|---|---|---|---|---|
| | | | C | H | N | $[\alpha]_D^{25(d)}$ |
| (−)2'R,6S,6aR, 9R,10aR | 145–154 (dec.) | 437 | 68.41 | 7.66 | 2.95 | −100 |
| (−)2'S,6S,6aR, 9R,10aR | 224–225 (dec.) | 437 | 68.09 | 7.47 | 2.94 | −118 |
| +2'S,6R,6aS, 9S,10aS | 135–140 (dec.) | 437 | 67.29 | 7.56 | 3.02 | +110 |
| +2'R,6R,6aS, 9S,10aS | 218–220 (dec.) | 437 | 67.75 | 7.58 | 2.89 | +110 |

$^{(b)}$100%
$^{(c)}$Calc'd for C$_{27}$H$_{35}$O$_4$N.HCl: C, 68.41; H, 7.66; N, 2.95
$^{(d)}$C = 1.0, CH$_3$OH The d,l-5,6,6a,7-tetrahydro-1-acetoxy-6-β-methyl-3-(5-phenyl-2-pentyloxy)benzo[c]quinolin-9(8H)-one is prepared as follows:

To a stirred solution of d,l-5,6,6a,7-tetrahydro-1-hydroxy-6β-methyl-3-(5-phenyl-2-pentyloxy)benzo[c]quinolin-9(8H)-one (4.5 g., 0.0115 mole) in pyridine (45 ml.) at room temperature is added acetic anhydride (45 ml.). The resulting solution is stirred for 3.5 hours and is then poured onto ice-water (250 ml.) and the mixture extracted with diisopropyl ether (2×250 ml.). The combined extracts are washed with water (3×200 ml.), dried (MgSO$_4$) and evaporated under reduced pressure to a yellow-brown oil which solidifies on scratching the walls of the flask containing it. Trituration of the solid with n-heptane gives 2.0 g. of the 1-acetoxy derivative (40% yield). It is purified by recrystallization from hot chloroform-n-hexane (1:4) to give the pure ester; m.p. 136°–140° C.

m/e - 433 (m+).

$^1$H NMR (60 MHz) $\delta_{CDCl_3}^{TMS}$ (ppm): 7.21 (bs, 5H, aromatic), 6.62 (d, J=1.5 Hz, 1H, C=C—H), 5.97 (d, J=3 Hz, 1H, meta H), 5.86 (d, J=3 Hz, 1H, meta H), 2.27 [s, 3H, CH$_3$—C(=O)], 1.21 (d, J=7 Hz, 6H, CH$_3$-C-N, CH$_3$—C—O), 1.49–4.51 (m, 14H, remaining protons).

The following tetrahydro-1-acetoxy-3-(5-phenyl-2-pentyloxy)benzo[c]quinolin-9(8H)-ones are similarly prepared from appropriate reactants according to the above procedures.

2.296 mmole) dropwise over a period of five minutes. The reaction mixture is stirred an additional 30 minutes at −78° C. and is then poured, with stirring, into a solution of 5% acetic acid (250 ml.) and ether (500 ml.) pre-cooled to 0° C. The layers are separated and the aqueous layer extracted with additional ether (250 ml.). The combined ether extracts are washed successively with water (2×250 ml.), saturated sodium bicarbonate solution (1×250 ml.) and brine (1×250 ml.), dried (MgSO$_4$) and concentrated in vacuo to give a yellow oil (1.4 g.). The crude oil is chromatographed on silica gel (100 g.) using benzene/ether (3:1) as eluant. After elution of less polar impurities, the title compound is isolated as a clear oil (700 mg.). The oil is dissolved in ether (35 ml.) and treated with ether saturated with HCl gas to give the hydrochloride salt of the title compound (448 mg.), m.p. 115°–124° C. after recrystallization from ether/chloroform.

MS (mol.ion)=437.

IR (KBr): 5.58 μ (ester >C=O).

Analysis: Calc'd for C$_{27}$H$_{35}$O$_4$N.HCl: C, 68.41; H, 7.66; N, 2.96%. Found: C, 68.52; H, 7.91; N, 2.73%.

The following compounds are prepared in like manner from appropriate reactants:

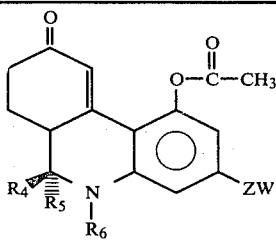

| ZW | R$_4$ | R$_5$ | R$_6$ | (°C.) m.p. | m/e (m+) | Formula | Calc'd C, H, N | Found C, H, N |
|---|---|---|---|---|---|---|---|---|
| —C(CH$_3$)$_2$C$_6$H$_{13}$ | CH$_3$ | H | H | 108–112 | 397 | C$_{25}$H$_{35}$NO$_3$ | C-75.53<br>H- 8.87<br>N- 3.52 | C-75.62<br>H- 8.73<br>N- 3.52 |
| —OCH(CH$_3$)(CH$_2$)$_3$C$_6$H$_5$ [6R,6aR] | H | CH$_3$ | H | 125–130 | 433 | C$_{27}$H$_{31}$O$_4$N | C-74.80<br>H- 7.21<br>N- 3.23 | C-74.96<br>H- 7.11<br>N- 3.19 |
| —OCH(CH$_3$)(CH$_2$)$_3$C$_6$H$_5$ [6S,6aR] | CH$_3$ | H | H | 145–146 | 433 | C$_{27}$H$_{31}$O$_4$N | C-74.80<br>H- 7.21<br>N- 3.23 | C-74.91<br>H- 7.20<br>N- 3.24 |
| —OCH(CH$_3$)(CH$_2$)$_3$C$_6$H$_5$ [2'S,6S,6aR] | CH$_3$ | H | H | 167–168 | 433 | C$_{27}$H$_{31}$O$_4$N | C-74.80<br>H- 7.21<br>N- 3.23 | C-74.66<br>H- 7.20<br>N- 3.33 |
| —OCH(CH$_3$)(CH$_2$)$_3$C$_6$H$_5$ [2'R,6S,6aR] | CH$_3$ | H | H | 120–121 | 433 | C$_{27}$H$_{31}$O$_4$N | C-74.80<br>H- 7.21<br>N- 3.23 | C-74.58<br>H- 7.19<br>N- 3.27 |
| —OCH$_2$CH$_2$C$_6$H$_5$ | CH$_3$ | H | H | 159–160 | 391 | C$_{24}$H$_{25}$O$_4$N | C-73.63<br>H- 6.44<br>N- 3.58 | C-73.38<br>H- 6.41<br>N- 3.59 |

EXAMPLE 42 dl-cis-5,6,6aβ,7,8,9,10,10aβ-octahydro-1-acetoxy-9α-hydroxy-6β-methyl-3-(5-phenyl-2-pentyloxy)benzo[c]quinoline To a solution of dl-cis-5,6,6aβ,7,10,10aβ-hexahydro-1-acetoxy-6β-methyl-3-(5-phenyl-2-pentyloxy)benzo[c]quinolin-9(8H)-one (1.0 g., 2.296 mmole in dry tetrahydrofuran (100 ml.) at −78° C. is added, with stirring, potassium tri-sec-butyl borohydride (4.6 ml. of 0.5M,

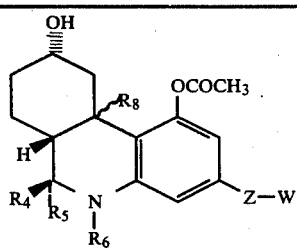

| −Z−W | R4 | R5 | R6 | R8 | M.P. (°C.) | MS (m+) |
|---|---|---|---|---|---|---|
| 5-phenyl-2-pentyloxy | CH3 | H | H | ⫽H | 168–170*(a) | 437 |
| 5-phenyl-2-pentyloxy | H | CH3 | H | ⫽H | oil | |
| 5-phenyl-2-pentyloxy | H | CH3 | H | ⫽H | oil | 437 |
| 5-phenyl-2-pentyloxy | CH3 | H | CH3 | ⫽H | 159–162*(b) | 451 |

*HCl salt. Analysis:
(a)Calc'd. for C27H35O4N.HCl: C, 68.41; H, 7.66; N, 2.96%
Found: C, 68.48; H, 7.57; N, 2.93%
(b)Calc'd. for C28H37O4N.HCl: C, 68.88; H, 7.85; N, 2.87%
Found: C, 68.42; H, 7.78; N, 2.75%

EXAMPLE 43

Following the procedure of Example 40 but using the appropriate 5,6,6a,7,10,10a-hexahydro-1-acyloxy-6-R4-3-(Z-W)-benzo[c]quinolin-9(8H)-ones of Examples 35, 37, 47 and 49 and the appropriate acid anhydride affords the isomeric alkanoyloxy compounds having the formula

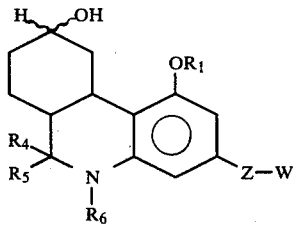

wherein R4, R5, R6, Z and W are as defined in Examples 35, 37, 47 and 49 and R1 is acetyl, propionyl, butyryl, valeryl or benzoyl.

EXAMPLE 44 dl-trans-5,6,6aβ,7,8,9,10,10aα-octahydro-1,9-diacetoxy-6β-methyl-3-(2-heptyloxy)benzo[c]quinoline 1.2 g. of the unchromatographed reduction product of dl-trans-5,6,6aβ,7,8,9,10,10aα-octahydro-1-acetoxy-9-hydroxy-6β-methyl-3-(2-heptyloxy)benzo[c]quinoline from Example 40 is stirred with excess acetic anhydride and pyridine overnight at room temperature. The mixture is poured into ice water, the aqueous mixture extracted with ether (3×100 ml.) and the combined extracts washed with water, brine, then dried (MgSO4) and evaporated. The residue is subjected to column chromatography (40 g. silica gel, benzene/ether [9:1] as eluting solvent) to give 680 mg. of the desired dl-trans-5,6,6aβ,7,8,9,10,10aα-octahydro-1,9-diacetoxy-6β-methyl-3-(2-heptyloxy)benzo[c]quinoline, which crystallizes on addition of hexane and ethyl acetate, m.p. 86°–87° C.

m/e - 431 (m+)

IR (KBr)-5.73 μ(ester carbonyls).

$^1$H NMR (60 MHz) $\delta_{CDCl_3}^{TMS}$ (ppm): 5.88 (bs, H2, H4-2H), 2.28 and 2.05 [2 three-proton singlets, CH3—C(=O)—], and ca. 0.8–5.0 (multiplets, remaining protons).

Analysis: Calc'd for C25H37O5N: C, 69.57; H, 8.64; N, 3.25%. Found: C, 69.51; H, 8.54; N, 3.14%.

Similar treatment of 60 mg. dl-trans-5,6,6aβ,7,8,9,10,10aα-octahydro-1-acetoxy-9β-hydroxy-6β-methyl-3-(4-phenylbutyloxy)benzo[c]quinoline in pyridine (1 ml.) and acetic anhydride (1 ml.) for 1 hour at room temperature yields the desired dl-trans-5,6,6aβ,7,8,9,10,10aα-octahydro-1,9β-diacetoxy-6β-methyl-3-(4-phenylbutyloxy)benzo[c]quinoline, m.p. 146°–147° C. after recrystallization from ethyl acetate/hexane (1:1).

m/e - 465 (m+)

Analysis: Calc'd for C28H35O5N: C, 72.23; H, 7.58; N, 3.01%. Found: C, 72.17; H, 7.61; N, 3.08%.

Similarly, acylation of the compounds of Examples 40, 43 and 61 with the appropriate acid anhydride affords 1,9-diacyloxy derivatives having the formula below wherein R1, R4, R5, R6, Z and W are as defined in Examples 40, 43 and 61 and R' is acetoxy, propionyloxy, butyryloxy, valeryloxy or benzoyloxy.

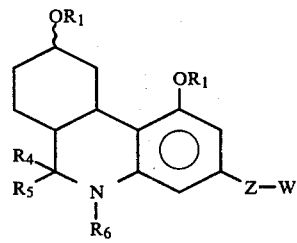

EXAMPLE 45

The 1-acyloxy derivatives of Examples 40 and 43 acylated at the 9-position according to the procedure of Example 44 but using an acid anhydride which provides an acyl moiety different from that of the acyl moiety at the 1-position. In this manner, diacyloxy derivatives having different acyloxy groups at the 1- and 9-positions are prepared.

EXAMPLE 46 d,l-trans-5,6,6aβ,7,8,9,10,10aα-octahydro-1,9-dihydroxy-6β-methyl-3-(2-heptyloxy)-benzo[c]quinoline A solution of 130 mg. d,l-trans-5,6,6aβ,7,8,9,10,10aα-octahydro-1-acetoxy-9-hydroxy-6β-methyl-3-(2-heptyloxy)-benzo[c]quinoline and 46 mg. potassium carbonate in 35 ml. methanol is stirred at room temperature. After 30 minutes, the reaction mixture is neutralized with acetic acid and concentrated under reduced pressure. The residue is dissolved in ether (100 ml.), washed successively with water (2×35 ml.), saturated sodium bicarbonate (1×35 ml.), brine (1×40 ml.), dried (MgSO4) and concentrated under reduced pressure to give 96 mg. d,l-trans-5,6,6aβ,7,8,9,10,10aα-octahydro-1,9-dihydroxy-6β-methyl-3-(2-heptyloxy)-benzo[c]quinoline as an amorphous solid, m.p. 80°–100° C. (dec.).

m/e - 347 (m+)

The NMR (CDCl3, 60 MHz) shows no absorption for the acetate methyl and the IR (CHCl3) had no absorption for an ester carbonyl.

In like manner, the following compound is prepared from the corresponding 1-acetoxy derivative of Example 41.

d,l-trans-5,6,6aβ,7,8,9,10,10aα-octahydro-1,9-dihydroxy-6β-methyl-3-(5-phenyl-2-pentyloxy)benzo[c]quinoline.

m/e-395 (m+)

Conversion to the hydrochloride gives a powder, m.p. 151°–156° C.

IR (KBr): 3.00, 4.00 (HN⊕=), 6.10 and 6.25μ.

Similarly, d,l-trans-5,6,6aβ,7,10,10aα-hexahydro-1-acetoxy-5-methyl-6β-methyl-3-(2-heptyloxy)benzo[c]quinolin-9(8H)-one is hydrolyzed to the corresponding 1-hydroxy compound; m.p. 157°–160° C.

m/e - 359 (m+)

Analysis: Calc'd for $C_{22}H_{33}O_3N$: C, 73.50; H, 9.25; N, 3.90%. Found: C, 73.16; H, 9.14; N, 3.85%.

Hydrolysis of the 1-acyloxy derivatives of Example 43 according to the above procedure affords compounds having the formula below wherein $R_4$, $R_5$, $R_6$, Z and W are as defined in Example 43.

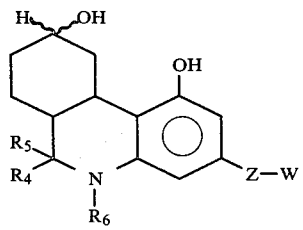

EXAMPLE 47 d,l-trans-5,6,6aβ,7,10,10aα-hexahydro-1-acetoxy-3-(2-heptyloxy)-5-benzoyl-6β-methylbenzo[c]quinolin-9(8H)-one To a stirred solution of the product of Example 36, d,l-trans-5,6,6aα,7,10,10aα-hexahydro-1-acetoxy-6β-methyl-3-(2-heptyloxy)-benzo[c]quinolin-9(8H)-one (812 mg.) in 2.5 ml. pyridine is added 421 mg. benzoyl chloride in 5 ml. chloroform. After two hours, the reaction mixture is poured onto ice and extracted twice with ether. The combined ether extracts are washed with water, sodium bicarbonate, dried (MgSO4) and filtered to yield, after concentration and crystallization from ether/petroleum ether, d,l-trans-5,6,6aβ,7,10,10aα-hexahydro-1-acetoxy-3-(2-heptyloxy)-5-benzoyl-6β-methylbenzo[c]quinolin-9(8H)-one, m.p. 108°–110° C.

m/e - 491 (m+)

Repetition of this procedure but using an equivalent amount of acetyl chloride in place of benzoyl chloride and the appropriate benzo[c]quinoline affords the following compound:

d,l-trans-5,6,6aβ,7,10,10aα-hexahydro-1-acetoxy-3-(2-heptyloxy)-5-acetyl-6β-methylbenzo[c]quinolin-9(8H)-one.

m/e - 433 (m+)

In like manner, the remaining compounds of Example 36 and those of Example 34 are converted to their corresponding benzoyl, acetyl, propionyl, butyryl, valeryl, 2-phenylacetyl and 4-phenylbutyryl derivatives by reaction with the appropriate acyl chloride. The compounds have the formula

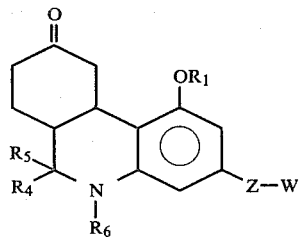

wherein $R_4$, $R_5$, Z, W and $R_1$ are as defined in Examples 34 and 36 and $R_6$ is benzoyl, acetyl, propionyl, butyryl, valeryl, 2-phenylacetyl or 4-phenylvaleryl

EXAMPLE 48 d,l-trans-5,6,6aβ,7,10,10aα-hexahydro-1-acetoxy-5-methyl-6β-methyl-3-(2-heptyloxy)-benzo[c]quinolin-9(8H)-one To a stirred solution of 387 mg. d,l-trans-5,6,6aβ,7,10,10aβ-hexahydro-1-acetoxy-6β-methyl-3-(2-heptyloxy)-benzo[c]quinolin-9(8H)-one in 3 ml. acetonitrile cooled to 15° C. is added 0.5 ml. 37% aqueous formaldehyde followed by 100 mg. sodium cyanoborohydride. Acetic acid is added to maintain a neutral pH until the reaction is complete as evidenced by no remaining starting material by thin layer chromatography. The product is isolated in the following manner.

Ice water and ether is added to the reaction mixture, the ether layer separated and the aqueous extracted once more with ether. The combined ether layers are combined, dried and evaporated to yield the desired, d,l-trans-5,6,6aβ,7,10,10aα-hexahydro-1-acetoxy-5-methyl-6β-methyl-3-(2-heptyloxy)benzo[c]quinolin-9(8H)-one as an oil.

$^1$H NMR (60 MHz, CDCl$_3$) shows a characteristic absorption at 2.85 ppm for >N—CH$_3$.

In like manner, the following compounds are prepared from appropriate reactants:

d,l-trans-5,6,6aβ,7,10,10aα-hexahydro-1-acetoxy-5-methyl-3-(2-heptyloxy)benzo[c]quinolin-9(8H)-one, an oil.

d,l-trans-5,6,6aβ,7,8,9,10,10aα-octahydro-1,9-diacetoxy-5-methyl-6β-methyl-3-(2-heptyloxy)benzo[c]quinoline, an oil.

m/e - 445 (m+) In addition, the following compounds are similarly prepared:

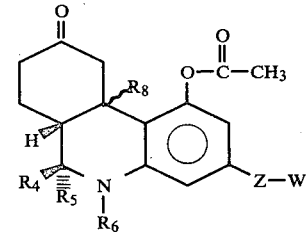

| —Z—W | $R_4$ | $R_5$ | $R_6$ | $R_8$ | M.P. | m/e (m+) |
|---|---|---|---|---|---|---|
| CH$_3$<br>\|<br>—O—CH—(CH$_2$)$_3$C$_6$H$_5$ | CH$_3$ | H | CH$_3$ | H | 94°–97° C.$^1$ | 449 |
| CH$_3$<br>\|<br>—O—CH—(CH$_2$)$_3$C$_6$H$_5$ | CH$_3$ | H | CH$_3$ | H | oil$^2$ | 449 |

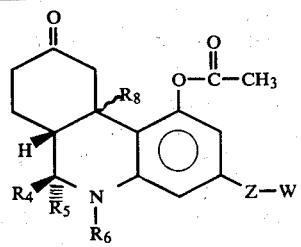

| —Z—W | R4 | R5 | R6 | R8 | M.P. | m/e (m+) |
|---|---|---|---|---|---|---|
| —O—(CH2)4C6H5 | CH3 | H | CH3 | H | 102°–103° C.[3] | 435 |

[1] As the HCl salt.
Analysis:
Calc'd for $C_{28}H_{35}O_4N\cdot HCl$: C, 69.19; H, 7.47; N, 2.88%
Found: C, 68.72; H, 7.18; N, 2.74%
[2] Analysis:
Calc'd for $C_{28}H_{35}O_4N$: C, 74.80; H, 7.85; N, 3.12%
Found: C, 74.66; H, 8.05; N, 2.66%
m.p. 69°–75° C. as the HCl salt.
[3] Analysis:
Calc'd for $C_{27}H_{33}O_4N$: C, 74.45; H, 7.64; N, 3.22%
Found: C, 73.89; H, 7.51; N, 3.04%

EXAMPLE 49

Repetition of the procedure of Example 48 but using the compounds of Examples 34 and 36–39 as reactants affords compounds having the formula below wherein $R_4$, $R_5$, $R_1$, Z and W are as defined in said Examples:

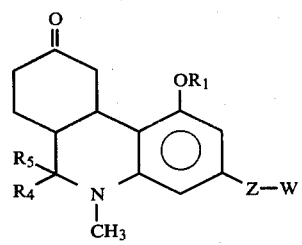

EXAMPLE 50 d,l-trans-5,6,6aβ,7,8,9,10,10aα-octahydro-1,9-dihydroxy-5-ethyl-6β-methyl-3-(2-heptyloxy)benzo[c]quinoline To a solution of 100 mg. lithium aluminum hydride in 5 ml. dry tetrahydrofuran (cooled in an ice/water bath) is added dropwise a solution of 90 mg. d,l-trans-5,6,6aβ,7,8,9,10,10aα-octahydro-1,9-dihydroxy-5-acetyl-6β-methyl-3-(2-heptyloxy)benzo[c]quinoline in 3 ml. tetrahydrofuran. After the addition is complete, the reaction mixture is heated at reflux for one hour and is then allowed to cool to room temperature. Equivalent amounts of water, followed by 3N potassium hydroxide are added, the resultant precipitate filtered and the filtrate concentrated in vacuo to yield the desired N-ethyl derivative as an oil.

m/e-375 (m+)

Similarly, the 5-acyl derivatives of Example 47 are reduced to the corresponding aralkyl or alkyl derivatives having the formula:

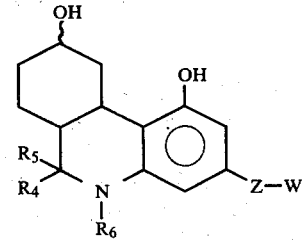

wherein $R_4$, $R_5$, Z and W are as defined in said Example and $R_6$ is aralkyl or alkyl.

EXAMPLE 51 d,l-trans-5,6,6aβ,7,8,9,10,10aβ-octahydro-1-acetoxy-9-hydroxy-5-methyl-3-(5-phenyl-2-pentyloxy)benzo[c]quinoline Formaldehyde (1.1 ml. of 37% aqueous) is added to a solution of d,l-trans-5,6,6aβ,7,10,10aα-hexahydro-1-acetoxy-3-(5-phenyl-2-pentyloxy)benzo[c]quinolin-9(8H)-one in acetonitrile (15 ml.) at room temperature, followed by sodium cyanoborohydride (0.262 g.). The reaction mixture is stirred for one hour during which time the pH is maintained at neutral pH by addition of acetic acid as needed. Additional sodium cyanoborohydride (0.262 g.) and methanol (15 ml.) are added to the reaction mixture, which is then acidified to pH 3, stirred for two hours, and concentrated under reduced pressure to an oil. The oil is diluted with water (50 ml.), the pH then adjusted to 9–10 by means of aqueous sodium hydroxide, and the alkaline mixture extracted with ether (3×200 ml.). The combined ether extracts are washed with brine, dried ($Na_2SO_4$) and concentrated under reduced pressure to a clear oil. The oil is then dissolved in 50% ether-hexane and charged to a silica gel column. The column is eluted first with 50% ether-hexane followed by 60%, 70% and 75% ether-hexane. The eluate is monitored by thin layer chromatography (ether-10, hexane-1). The first product collected is d,l-trans-5,6,6a,7,10,10a-hexahydro-1-acetoxy-5-methyl-3-(5-phenyl-2-pentyloxy)benzo[c]quinolin-9(8H)-one (0.125 g.)

m/e-435 (m+)

Analysis: Calc'd for $C_{27}H_{33}O_4N$: C, 74.45; H, 7.64; N, 3.22%. Found: C, 74.06; H, 7.77; N, 3.31%.

The second product is the 9α-hydroxy diastereomer of the title compound (25 mg.).

m/e-437 (m+)

Analysis: Calc'd for $C_{27}H_{35}O_4N$: C, 74.11; H, 8.06; N, 3.20%. Found: C, 73.96; H, 8.34; N, 3.00%.

The third product is the 9β-hydroxy diastereomer of the title compound (0.7 g.).

m/e-437 (m+)

Analysis: Calc'd for $C_{27}H_{35}O_4N$: C, 74.11; H, 8.06; N, 3.20%. Found: C, 73.56; H, 7.86; N, 3.21%.

Similarly, d,l-trans-5,6,6aβ,7,10,10aα-hexahydro-1-acetoxy-3-(2-heptyloxy)benzo[c]quinolin-9(8H)-one is treated with sodium cyanoborohydride to give:

d,l-trans-5,6,6aβ,7,10,10aα-hexahydro-1-acetoxy-5-methyl-3-(2-heptyloxy)benzo[c]quinolin-9(8H)-one as an oil.

m/e-387 (m+)

IR (CHCl3): 5.80 (ketone C=O), 5.65 (ester C=O), μ.

Analysis: Calcd for $C_{23}H_{33}O_4N$: C, 71.29; H, 8.58; N, 3.61%. Found: C, 70.78; H, 8.71; N, 3.27%.

d,l-trans-5,6,6aβ,7,8,9,10,10aα-octahydro-1-acetoxy-9β-hydroxy-5-methyl-3-(2-heptyloxy)benzo[c]quinoline, an oil.

m/e-389 (m+)

IR (CHCl₃): 280 (O—H); 5.70 (ester C=O),μ.

Analysis: Calc'd for C₂₃H₃₅O₄N: C, 70.92; H, 9.06; N, 3.60%. Found: C, 70.56; H, 8.95; N, 3.56%.

and d,l-trans-5,6,6aβ,7,10,10aα-hexahydro-1-acetoxy-6β-methyl-3-(5-phenyl-2-pentyloxy)benzo[c]quinolin-9(8H)-one is converted to:

d,l-trans-5,6,6aβ,7,10,10aα-hexahydro-1-acetoxy-5-methyl-6β-methyl-3-(5-phenyl-2-pentyloxy)benzo[c]quinolin-9(8H)-one;

d,l-trans-5,6,6aβ,7,8,9,10,10aα-octahydro-1-acetoxy-9β-hydroxy-5-methyl-6β-methyl-3-(5-phenyl-2-pentyloxy)benzo[c]quinoline, which is isolated as the hydrochloride salt; m.p. 163°–165° C.

m/e-451 (m+)

EXAMPLE 52 d,l-trans-5,6,6aβ,7,10,10aα-hexahydro-1-acetoxy-5-isobutyryl-3-(5-phenyl-2-pentyloxy)benzo[c]quinolin-9(8H)-one A solution of isobutyryl chloride (114 mg., 1.07 mmole) in chloroform (20 ml.) is slowly added with stirring to a solution of d,l-trans-5,6,6aβ,7,10,10aα-hexahydro-1-acetoxy-3-(5-phenyl-2-pentyloxy)benzo[c]quinolin-9(8H)-one (450 mg., 1.07 mmole) in dry pyridine (1.5 ml.) at 0° C. and under a nitrogen atmosphere. The reaction mixture is stirred for five hours and is then poured into ice/water (50 ml.). The chloroform layer is separated and the aqueous layer extracted with chloroform (2×20 ml.). The chloroform extracts are combined and washed with 10% hydrochloric acid (2×10 ml.), followed by brine (1×10 ml.), and then dried (MgSO₄). Concentration of the chloroform solution in vacuo gives a yellow oil which solidifies upon standing. Trituration of the solid with hexane affords a white crystalline solid, which is recovered by filtration and dried (400 mg.), m.p. 128°–129° C.

Concentration of the hexane filtrate gives 121 mg. of oil.

EXAMPLE 53 d,l-trans-5,6,6aβ,7,8,9,10,10α-octahydro-1-acetoxy-9β-hydroxy-5-isobutyryl-3-(5-phenyl-2-pentyloxy)benzo[c]quinoline Sodium borohydride (38 mg., 1.0 mmole) is slowly added to a solution of d,l-trans-5,6,6aβ,7,10,10aα-hexahydro-1-acetoxy-5-isobutyryl-3-(5-phenyl-2-pentyloxy)benzo[c]quinolin-9(8H)-one (260 mg., 0.529 mmole) in absolute ethanol (20 ml.) 5°–10° C. under a nitrogen atmosphere. The reaction mixture is stirred for one hour and is then acidified with 10% hydrochloric acid. The ethanol is removed by concentration under reduced pressure. Water (10 ml.) is added to the remaining solution which is then extracted with ethyl acetate (2×50 ml.). The extracts are combined, washed with brine and then dried (MgSO₄). Concentration in vacuo affords the title compound as an amorphous solid (213 mg.) which is used without further purification.

EXAMPLE 54 d,l-trans-5,6,6aβ,7,8,9,10,10aα-octahydro-1,9β-diacetoxy-5-isobutyl-3-(5-phenyl-2-pentyloxy)benzo[c]quinoline Under a nitrogen atmosphere, a solution of d,l-trans-5,6,6aβ,7,8,9,10,10aα-octahydro-1-acetoxy-9β-hydroxy-5-isobutyryl-3-(5-phenyl-2-pentyloxy)benzo[c]quinoline (213 mg., 0.432 mmole) in tetrahydrofuran (5 ml.) is added to a slurry of lithium aluminum hydride (100 mg., 2.6 mmole) in tetrahydrofuran (5 ml.) at room temperature. The mixture is stirred overnight and then water (0.1 ml.), 15% sodium hydroxide solution (0.1 ml.) and water (0.3 ml.) are added. It is then filtered under nitrogen and the filter cake washed with tetrahydrofuran (2×5 ml.). The combined filtrate and wash solution are concentrated to a reddish oil (0.174 g.).

The oil is dissolved under nitrogen in pyridine (1 ml.) and the solution cooled to 0° C. Acetic anhydride (1 ml.) is added, with stirring, to the pyridine solution and the reaction mixture stirred for 30 minutes at 0° C. It is then poured into water (25 ml.) and extracted with ethyl acetate (3×25 ml.). The extracts are combined, washed with brine, dried (MgSO₄) and concentrated to a brown oil (184 mg.). The oil is flushed with nitrogen and chromatographed on silica gel (40 g.) using benzene/ether (9:1) as eluant. Fractions of 10 ml. each are collected. Fractions 2–10 are combined and concentrated to an oil (109 mg.).

m/e-521 (m+)

Analysis: Calc'd for C₃₂H₄₃O₅N: C, 73.67; H, 8.31; N, 2.68%. Found: C, 74.33; H, 8.89; N, 2.23%.

¹H NMR (60 MHz) $\delta_{CDCl_3}^{TMS}$ (ppm): 7.22 (s, 5H, aromatic), 6.05 (d, 1H, aromatic), 5.90 (d, 1H, aromatic), 4.90 (bs, 1H), 4.30 (bs, 1H), 3.10 (d, 2H, N—CH₂), 2.90 (d, 2H, N—CH₂), 2.70 (bs, 2H), 2.40 and 2.15 (s, 6H, 2—CH₃—COO—), 1.85 (bs, 2H, H₇ H₈), 1.5 (m), 1.05

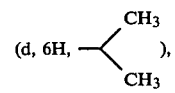

1.0–3.0 (variable, remaining protons).

EXAMPLE 55 d,l-trans-5,6,6aβ,7,10,10aα-Hexahydro-1-hydroxy-5-acetyl-6β-methyl-9-methylene-3-(2-heptyloxy)benzo[c]quinoline A. Triphenylmethyl phosphonium bromide (742 mg., 2.12 mmole) is added to a solution of sodium hydride (0.95 g., 2.0 mmole) in dimethyl sulfoxide (50 ml.) at 50° C. The reaction mixture is then heated at 70° C. for three hours after which d,l-trans-5,6,6aβ,7,10,10aα-hexahydro-1-acetoxy-5-acetyl-6β-methyl-3-(2-heptyloxy)-benzo[c]quinolin-9(8H)-one (0.858 g., 2.0 mmole) in dimethyl sulfoxide (50 ml.) is added. The reaction mixture is heated at 70° C. overnight, and then cooled and poured into a mixture of ice and water containing sodium bicarbonate (12.5 g.). The aqueous mixture is extracted with benzene, dried (Na₂SO₄) and evaporated under reduced pressure to give the crude product. It is purified by column chromatography over silica gel in hexanebenzene (1:1).

B. d,l-trans-5,6,6aβ,7,10,10aα-hexahydro-5-acetyl-1-hydroxy-6β-methyl-9-methylene-3-(5phenyl-2-pentyloxy)benzo[c]quinoline.

A slurry of 0.94 g. (0.039 mole) of sodium hydride (obtained by washing 1.87 g. of 50% sodium hydride in mineral oil dispersion with dry pentane) in 57 ml. dimethylsulfoxide is heated at 50° C. for 2.5 hours. After the addition of 15.32 g. (0.043 mole) of triphenylmethylphosphonium bromide, the reaction is heated for 2 hours at 60° C. A solution of 1.86 g. (0.004 mole) of d,l-trans-5,6,6aβ,7,10,10aα-hexahydro-1-acetoxy-5-acetyl-6β-methyl-3-(5-phenyl-2-pentyloxy)benzo[c]quinoline-9(8H)-one, in 57 ml. dimethylsulfoxide is added and the reaction is heated at 60° C. for 30 minutes. The cooled reaction mixture is poured into 200 ml. ice-water containing 20 g. sodium bicarbonate. This is extracted twice with ethylacetate (50 ml. each), the combined organic layers are washed with 50 ml. water, 50 ml. brine, over magnesium sulfate, filtered and evaporated the solvent to afford an orange colored oil (contains triphenylphosphine oxide by thin-layer chromatography). Purification is achieved via chromatography (Brinkman silica-gel 125 g.; solvent; cyclohexane 3, ether 1) to afford the title compound, 1.251 g. (74% yield), m.p. 174°-176° C.

Analysis: Calc'd. for $C_{28}H_{35}O_3N$: C, 77.56; H, 8.14; N, 3.23%. Found: C, 77.29; H, 7.96; N, 3.22%.

I.R. (KBr): 2.98μ (s), 3.34μ (m), 3.38μ (m), 3.44μ (m), 6.10μ (s), 6.24μ (s) 6.58μ (s), 6.90μ (s).

m/e - 433 (m+).

$^1$HNMR (60 MHz) $\delta_{CDCl_3}^{TMS}$: 8.80 (s, 1H, phenol), 7.16 (m, 5H, arom.), 6.32 (d, 1H, C-2H), 6.09 (d, 1H, C-4H), 4.64 (broad s, 2H, vinyl), 1.96 & 1.93 (2s, 3H, amide—CH$_3$), 1.27 & 1.25 (2d, 3H, C$_6$—CH$_3$), 1.02, d, 3H (side chain CH$_3$), 0.9-4.5 (variable remaining protons).

Similarly prepared from the appropriate starting material is: dl-cis-5,6,6aβ,7,10,10aβ-hexahydro-5-acetyl-1-hydroxy-6β-methyl-9-methylene-3-(5-phenyl-2-pentyloxy)benzo[c]quinoline.

m.p. 168-169.5, yield: 88%.

Analysis: Calc'd. for $C_{28}H_{35}O_3N$: C, 77.56; H, 8.14; N, 3.23%. Found: C, 77.25; H, 8.14; N, 3.12%.

$^1$HNMr (60 MHz) $\delta_{CDCl_3}^{TMS}$: 8.82 (s, 1H, phenol), 7.16 (m, 5H, arom.), 6.36 (d, 1H, C-2H), 6.12 (d, 1H, C-4H), 4.68 (broad s, 2H, vinyl), 2.08 & 2.06 (2S, 3H, amide-CH-$_3$), 1.22 & 1.20 (2d, 3H, C-$_6$CH$_3$), 1.10 d, 3H, side chain CH$_3$), 1.50-4.50 (variable remaining protons).

I.R. (KBr): 2.95μ (m), 3.36μ (s), 6.10μ (s), 6.33μ (s), 6.88μ (s), 7.20μ (s), 7.35μ (s), 8.50μ (s).

m/e - 433 (m+).

Similarly, the remaining keto derivatives described herein are converted to their corresponding 9-methylene derivatives.

EXAMPLE 56 d,l-trans-5,6,6aβ,7,8,9,10,10aα-octahydro-1-hydroxy-5-ethyl-9-hydroxymethyl-6β-methyl-3-(2-heptyloxy)benzo[c]quinoline To a solution of d,l-trans-5,6,6aβ,7,10,10aα-hexahydro-1-hydroxy-5-acetyl-6β-methyl-9-methylene-3-(2-heptyloxy)benzo[c]quinoline (0.855 g., 2 mmole) in tetrahydrofuran (30 ml.) at 0°-5° C., is added dropwise a 1M solution of diborane in tetrahydrofuran (borane-tetrahydrofuran complex) 6 ml.). After the addition the reaction mixture is held at room temperature for 30 minutes and then treated with water to decompose excess hydride.

The reaction mixture is then warmed to 50° C. on a water bath and 3N sodium hydroxide (3 ml.) added followed by dropwise addition of 30% hydrogen peroxide (3 ml.). After addition, the mixture is held at room temperature for one hour, potassium carbonate (1.5 g.) added and the tetrahydrofuran layer separated. The aqueous phase is extracted with tetrahydrofuran (3×10 ml.), the extracts combined, dried (MgSO$_4$) and concentrated to give the product. Purification is achieved by column chromatography on silica gel using ether-hexane.

In like manner, the remaining 9-methylene compounds of formulae II, III and IV wherein the 1-hydroxy groups are protected by acetylation and compounds of formulae II and III wherein the 5-NH groups are protected by acetylation or alkylation are converted to their corresponding methylene derivatives. The N-acetyl groups are, of course, converted to N-ethyl groups and acetyloxy groups are converted to hydroxy groups.

EXAMPLE 57 d,l-7,10-dihydro-1-hydroxy-3-(2-heptyloxy)benzo[c]quinolin-9(8H)-one ethylene ketal and d,l-5,6,6a,7,10,10a-hexahydro-1-hydroxy-3-(2-heptyloxy)benzo[c]quinolin-9(8H)-one ethylene ketal A suspension of d,l-trans-5,6,6aβ,7-tetrahydro-1-hydroxy-3-(2-heptyloxy)benzo[c]quinolin-9(8H)-one (0.50 g., 1.52 mmoles), ethylene glycol (0.43 ml., 7.70 mmoles) and p-toluenesulfonic acid monohydrate (0.28 g., 1.46 mmoles) in benzene (25 ml.) is heated at reflux for 45 minutes. The by-product water is azeotropically removed. The dark suspension thus produced is taken up in a mixture of ether and saturated sodium bicarbonate solution. The organic layer is separated, washed with saturated aqueous sodium bicarbonate solution, dried (MgSO$_4$), and concentrated to an oil which is then chromatographed on silica gel (50 g.) using ether as eluant. Fractions of 10 ml. each are collected.

Fractions 12-18 are combined and evaporated to give 203 mg. of the ethylene ketal of the hexahydro derivative.

m/e - 375 (m+)

IR (CHCl$_3$): 2.98μ (superposition of N—H and O—H stretch).

$^1$H NMR (60 MHz) $\delta_{CDCl_3}^{TMS}$ (ppm): 5.7 (s, 2H, aromatic), 4.0 (s, 4H, ketal ethylene) and absorption for remaining protons.

Fractions 42-65 are combined and concentrated to afford 146 mg. of a yellow solid. Trituration of the solid in ether-pentane (1:1) gives 85 mg. of 7,10-dihydro-1-hydroxy-3-(2-heptyloxy)benzo[c]quinolin-9(8H)-one ethylene ketal, m.p. 171°-173° C.

m/e - 371 (m+); IR (KBr): 2.98μ (O—H).

$^1$H NMR (60 MHz) $\delta_{CDCl_3}^{TMS}$ (ppm): 8.6 (s, 1H, C-6 aromatic), 6.6 and 7.0 (bd, 2H, aromatic), 4.1 (bs, 4H, ethylene ketal), 3.9 (bs, 2H, C-10 methylene), 3.1 (t, 2H, C-7 ethylene) and other absorptions for remaining protons.

Analysis: Calc'd for $C_{22}H_{29}O_4N$: C, 71.13; H, 7.87; N, 3.77%. Found: C, 71.19; H, 7.67; N, 3.61%.

In like manner, d,l-5,6,6a,7,10,10a-hexahydro-1-hydroxy-3-(2-heptyloxy)-6-methylbenzo[c]quinolin-9(8H)-one ethylene ketal is converted to d,l-7,10-dihydro-1-hydroxy-3-(2-heptyloxy)-6-methylbenzo[c]quinolin-9(8H)-one ethylene ketal.

m/e - 385 (m+)

$^1$H NMR (60 MHz) $\delta_{CDCl_3}^{TMS}$ (ppm): 6.8 and 6.4 (two 1H doublets, aromatic 5.7 (bs, 1H, phenolic), 4.0 (bs, 4H, ethylene ketal), 3.9 (bs, 2H, C-10 —CH$_2$—) 3.1 (bt, 2H, C-8 —CH$_2$—), 2.5 (s, 3H, 6—CH$_3$), 2.0 (bt, 2H, C-7 —CH$_2$—), and other absorptions for remaining protons.

In like manner, the compounds of Examples 29–31 are converted to compounds having the formulae:

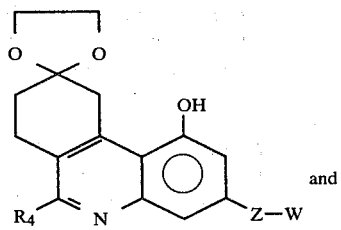

and

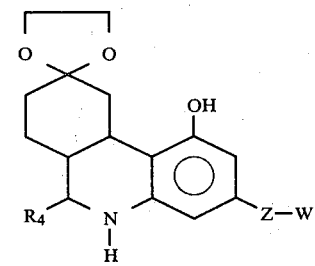

EXAMPLE □ d,l-5,6,6aβ,7,10,10aα-Hexahydro-1-hydroxy-6β-methyl-3-(2-heptylsulfinyl)benzo[c]quinolin-9(8H)-one Equimolar amounts of m-chloroperbenzoic acid and d,l-5,6,6aβ,7,10,10aα-hexahydro-1-hydroxy-6β-methyl-3-(2-heptylthio) benzo[c]quinolin-9(8H)-one are added to a mixture of chloroform and acetic acid (2:1) and the reaction mixture stirred for one hour at room temperature. The organic phase is then separated, washed with water, dried (MgSO$_4$) and evaporated to dryness to give the title product.

In like manner, the thio ethers of Examples 31, 33, 34, 43–47, 49, and 50 are oxidized to the corresponding sulfoxides.

EXAMPLE 59 d,l-trans-5,6,6a,7,10,10a-Hexahydro-1-hydroxy-6β-methyl-3-(2-heptylsulfonyl)benzo[c]quinolin-9(8H)-one The procedure of Example 58 is repeated but using two equivalents of m-chloroperbenzoic acid or oxidizing agent per mole of thio ether reactant to give the title compound.

Similarly, the thio ethers of Examples 31, 33, 34, 43–47, 49 and 50 are oxidized to their sulfonyl derivatives.

EXAMPLE 60

Following the procedure of Example 57 but using the appropriate ketone compound of formula II, III or IV and the appropriate alkylene glycol or alkylene dithiol having formula H—X'-alkylene-X'—H wherein X' is oxygen or sulfur and alkylene has from 2 to 4 carbon atoms affords compounds having the formulae:

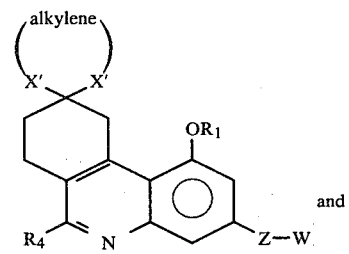

and

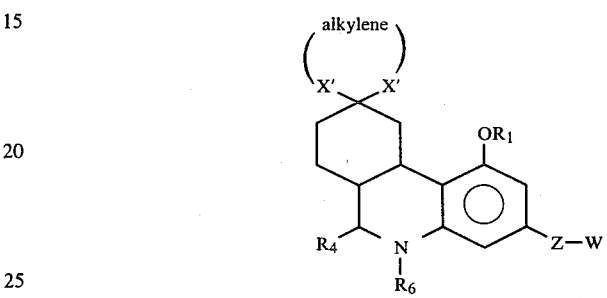

EXAMPLE 61 (2'R,6S,6aR, 9R,10aR)-(—)-1-Acetoxy-5,6,6a,7,8,9,10,10a-octahydro-9-hydroxy-5,6-dimethyl-3-(5-phenyl-2-pentyloxy)-benzo[c]quinoline To a stirred solution of 1.0 g. (0.0021 moles) (2'R,6S,6aR,9R,10aR)-(—)-1-acetoxy-5,6,6a,;7,8,9,10,-10a-octahydro-9-hydroxy-6-methyl-3-(5-phenyl-2-pentyloxy)-benzo[c]quinoline hydrochloride in 30 ml. CHCl$_3$ is added 30 ml. saturated NaHCO$_3$ solution, and the mixture stirred 5 minutes at room temperature. The layers are separated and the aqueous layer re-extracted with 20 ml. CHCl$_3$. The combined chloroform layers are dried (MgSO$_4$), filtered and the solvent removed in vacuo to yield the free base as a colorless foam.

This foam is dissolved in 40 ml. tetrahydrofuran and combined with 1.0 g. 5% Pd/C, 1.05 ml (0.018 moles=8.7 equiv.) glacial acetic acid and 15.8 ml. (0.20 moles=100 equiv.) 37% aqueous formaldehyde. The mixture is placed in a Parr apparatus at 50 p.s.i. and hydrogenated for 50 minutes. The catalyst is filtered through diatomaceous earth, washing well with ethyl acetate. The filtrate is diluted to 150 ml. with ethyl acetate then washed successively 3X with 100 ml. saturated NaHCO$_3$ solution, 75 ml. H$_2$O 3X, 75 ml. brine 1X, and dried over MgSO$_4$. The solvent is filtered and removed in vacuo yielding a yellow viscous oil which is chromatographed on 50 g. silica gel (0.04–0.63 mm.) and eluted with toluene/diethyl ether (1:1). Similar fractions are combined and removed in vacuo to yield a colorless oil which is redissolved in 50 ml. diethyl ether and dry HCl bubbled in under a nitrogen atmosphere with stirring. The resulting white solid is filtered under a nitrogen atmosphere and dried in vacuo (0.1 mm.) for 24 hours at room temperature to yield 0.45 g. (44%) of the title product, m.p. 90°–95° C. (d).

NMR (CDCl$_3$) - 2.73 ppm, singlet, 3H (N—CH$_3$).
IR (KBr) - 4.25μ

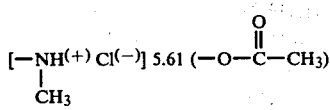

[—NH(+) Cl(−)] 5.61 (—O—C(=O)—CH₃)

Calc. for $C_{28}H_{37}O_4N·HCl$: C, 68.90; H, 7.85; N, 2.87% Found: C, 68.60; H, 7.92; N, 2.77%.
$[a]_D^{25} = -73°$ (C, 1.0, methanol).
Mass spectrum m/e=451 (m+).

The following compounds are similarly prepared:
dl-1-acetoxy-5,6,6aβ,7,8,9,10,10aα-octahydro-9β-hydroxy-5,6β-dimethyl-3-(1,1-dimethylheptyl) benzo[c]quinoline hydrochloride.
m.p. 129°–130° C. (d).
m/e=415 (m+, 100%).
IR (KBr)—5.67μ

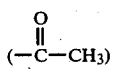

(—C(=O)—CH₃)

and dl-1-acetoxy-5,6,6aβ,7,8,9,10,10aα-octahydro-9β-hydroxy-5-methyl-6β-n-butyl-3-(5-phenyl-2-pentyloxy)benzo[c]quinoline hydrochloride.
m.p. 106°–108° C.
m/e=493.
$C_{31}H_{43}O_4N·HCl$: Calc'd.: C, 70.21; H, 8.37; N, 2.6% Found: C, 71.02; H, 8.43; N, 2.6%.

EXAMPLE 62

Preparation of dl-5,6,6aβ,7,8,9α,10,10aα-octahydro-1-acetoxy-5-benzoyl-9-benzoyloxy-6β-methyl-3-(1-methyl-4-phenylbutoxy)benzo[c]quinoline A stirred suspension of 47.4 g. (0.10 mol) of dl-5,6,6aβ,7,8,9α,-10,10aα-octohydro-1-acetoxy-9-hydroxy-6β-methyl-3-(1-methyl-4-phenylbutoxy)benzo[c]quinoline, hydrochloride and 500 ml. of CHCl₃ under a N₂ atmosphere is cooled to 0° C. and treated with 250 ml. pyridine followed by 58 ml. (0.50 mole) benzoyl chloride in 500 ml. chloroform. The resultant homogeneous solution is then refluxed on a steam bath for one hour. The reaction mixture is poured onto crushed ice and extracted with chloroform. The organic extracts are combined, washed successively with water (2×500 ml.), 10% hydrochloric acid, saturated sodium bicarbonate solution (500 ml.) and saturated brine solution (500 ml.), dried over MgSO₄, filtered and concentrated to give 119 g. of a light yellow oil. Chromatography on 2000 g. silica gel (20% EtOAc-cyclohexane) affords 50.5 g. (78%) of dl-5,6,6aβ,7,8-,9α,10,10α-octahydro-1-acetoxy-5-benzoyl-9-benzoyloxy-6β-methyl-3-(1-methyl-4-phenylbutoxy)benzo[c]quinoline, m.p. 125°–30° C.

Anal. Calcd. for $C_{41}H_{43}O_6N$: C, 76.24; H, 6.72; N, 2.17%. Found: C, 76.35; H, 6.92; N, 2.19%.

Separation of dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline and dl-5,6,6aβ,7,8,9α,10,10aα-octahydro-1-acetoxy-5-benzoyl-9-benzoyloxy-6β-methyl-3-(1α-methyl-4-phenylbutoxy)-benzo[c]quinoline Recrystallization of 50.5 g. dl-5,6,6aβ,7,8,9α,10,10aα-octahydro-1-acetoxy-5-benzoyl-9-benzoyloxy-6β-methyl-3-(1-methyl-4-phenylbutoxy)-benzo[c]quinoline from 2 l. 2-propanol yielded 23.8 of white solids, m.p. 136°–8°, which are recrystallized twice more from 2-propanol and once from acetonitrile to yield 5.7 g. of dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline, m.p. 148°–9° C.

The filtrate from the original 2-propanol recrystallization of dl-5,6,6aβ,7,8,9α,10,10aα-octahydro-1-acetoxy-5-benzoyl-9-benzoyloxy-6β-methyl-3-(1methyl-4-phenylbutoxy)benzo[c]quinoline is evaporated to a white foam and triturated with 500 ml. ether to yield 12.9 g. of white solids, m.p. 129°–132°. These solids are triturated twice again with ether to yield 3.8 g. of dl-5,6,6aβ,7,8,9α,10,10aα-octahydro-1-acetoxy-5-benzoyl-9-benzoyloxy-6β-methyl-3-(1α-methyl-4-phenylbutoxy)benzo[c]quinoline, m.p. 139°–141° C.

Preparation of dl-5,6,6aβ,7,8,9α,10,10aα-octahydro-1-acetoxy-9-hydroxy-6β-methyl-3-(1β-methyl-4-phenylbutoxy)benzo[c]quinoline, hydrochloride To a stirred solution of 2.0 g. (5.3 mmol) lithium aluminum hydride in 150 ml. tetrahydrofuran under a nitrogen atmosphere is added a solution of 5.7 g. (8.8 mmole) dl-5,6,6aβ,7,8,9α,10,10aα-octahydro-1-acetoxy-5-benzoyl-9-benzoyloxy-6β-methyl-3-(1β-methyl-4-phenylbutoxy)benzo[c]quinoline in 112 ml. tetrahydrofuran dropwise over a five minute period. The resultant mixture is heated at reflux for 45 minutes, cooled and poured carefully onto an ice cold mixture of 1125 ml. 5% acetic acid in water and 2250 ml. ether. This biphasic mixture is stirred for ten minutes and the layers separated. The aqueous layer is extracted with an additional 500 ml. ether and the combined ether extracts are washed successively with water (3×500 ml.), saturated sodium bicarbonate solution (2×500 ml.) and saturated brine solution (1×500 ml.), dried over MgSO₄, filtered and evaporated to yield 5.4 g. dl-5-benzyl-5,6,6aβ,7,8,9α,10,10aα-octahydro-1,9-dihydroxy-6β-methyl-3-(1β-methyl-4-phenylbutoxy)benzo[c]quinoline as a light purple oil.

dl-5-benzyl-5,6,6aβ,7,8,9α,10,10aα-octahydro-1,9-dihydroxy-6β-methyl-3-(1β-methyl-4-phenylbutoxy)-benzo[c]quinoline is immediately taken up in 450 ml. methanol and hydrogenated at atmospheric pressure over 4.27 g. Pd/C for 3 hours to yield dl-5,6,6aβ,7,8-,9α,10,10aα-octahydro-1,9-dihydroxy-6β-methyl-3-(1β-methyl-4-phenylbutoxy)benzo[c]quinoline after filtration of the catalyst and evaporation of the methanol.

dl-5,6,6aβ,7,8,9α,10,10aα-octahydro-1,9-dihydroxy-6β-methyl-3-(1β-methyl-4-phenylbutoxy)benzo[c]quinoline is immediately dissolved in 210 ml. methylene chloride, cooled to 0° C. under a nitrogen atmosphere, and treated successively with 1.35 ml. triethylamine, 1.19 g. (9.7 mmol) of 4-dimethylaminopyridine and finally with 0.834 ml. (8.8 mmol) of acetic anhydride. After stirring for 30 minutes, the reaction mixture is poured onto 250 ml. of water and the organic layer separated. The aqueous layer is extracted once more with methylene chloride and the combined methylene chloride layers washed successively with a saturated sodium bicarbonate solution (2×150 ml.), water (150 ml.) and a saturated brine solution, dried over MgSO₄, filtered, evaporated and chromatographed on 300 g. silica gel using 33% ether-toluene as eluent to give 1.4 g. dl-5,6,6aβ,7,8,9α,10,10aα-octahydro-1-acetoxy-9-hydroxy-6β-methyl-3-(1β-methyl-4-phenylbutoxy)benzo[c]quinoline, hydrochloride as the free base. Treatment of dl-5,6,6aβ,7,8,9α,10,10aα-octahydro-1-acetoxy-9-hydroxy-6β-methyl-3-(1β-methyl-4-phenylbutoxy)-benzo[c]quinoline, hydrochloride in ether with HCl (gas) yields 795 mg. dl-5,6,6aβ,7,8,9α,10,10aα-octahydro-1-acetoxy-9-hydroxy-6β-methyl-3-(1β-methyl-4-phenylbutoxy)benzo[c]quinoline, hydrochloride, m.p. 213°–215° C. after filtration and trituration in acetone, m/e=437 (m+, 100%). Anal. calcd. for $C_{27}H_{35}O_4N \cdot HCl$: C, 68.42; H, 7.66; N, 2.96. Found C, 68.48; H, 7.63; N, 3.05.

Similarly prepared from 3.8 g. dl-5,6,6aβ,7,8,9α,10,-10aα-octahydro-1-acetoxy-5-benzoyl-9-benzoyloxy-6β-methyl-3-(1α-methyl-4-phenylbutoxy)benzo[c]quinoline is 1.1 g. dl-5,6,6aβ,7,8,9α,10,10aα-octahydro-1-acetoxy-9-hydroxy-6β-methyl-3-(1α-methyl-4-phenylbutoxy)benzo[c]quinoline hydrochloride, m.p. 202°–205° (d.), m/e=437 (100%, m+).

Anal. Calcd. for $C_{27}H_{35}O_4N \cdot HCl$: C, 68.42; H, 7.66; N, 2.96. Found: C, 68.20; H, 7.56; N, 3.04.

EXAMPLE 63 d,l-5,6,6a,7-Tetrahydro-1-(4-morpholinobutyryloxy)-6β-methyl-3-(2-heptyloxy)benzo[c]quinolin-9(8H)-one To a solution of d,l-5,6,6a,7-tetrahydro-1-hydroxy-6β-methyl-3-(2-heptyloxy)benzo[c]quinolin-9(8H)-one (0.51 g., 1.5 mmole) in dry methylene chloride (25 ml.) is added 4-morpholinobutyric acid hydrochloride (0.315 g., 1.5 mmole) and the mixture stirred at room temperature under a nitrogen atmosphere. A 0.1 M solution of dicyclohexylcarbodiimide in methylene chloride (12.5 ml., 1.5 mmole) is added dropwise and the mixture stirred for 24 hours. It is then filtered and evaporated to give the title product which is purified by column chromatography on silica gel.

Repetition of this procedure but using the appropriate reactants of formula III and the appropriate alkanoic acid or acid of formula $HOOC\text{-}(CH_2)_p\text{—}NR_2R_3 \cdot HCl$ affords the following compounds:

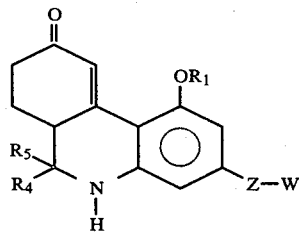

wherein $R_1, R_4, R_5$, Z and W are as defined in Examples 29, 30 and 31.

R₁

COCH₂CH₃
CO(CH₂)₂CH₃
CO(CH₂)₃CH₃
COCH₂NH₂
CO(CH₂)₂NH₂
CO(CH₂)₄NH₂
CO(CH₂)N(CH₃)₂
CO(CH₂)₂NH(C₂H₅)
CO(CH₂)₄NHCH₃
CONH₂
CON(C₂H₅)₂
CON(C₄H₉)₂
CO(CH₂)₃NH(C₃H₇)
CO(CH₂)₂N(C₄H₉)₂
COCH₂-piperidino
COCH₂-pyrrolo
CO(CH₂)₂-morpholino
CO(CH₂)₂-N-butylpiperazino
CO(CH₂)₃-pyrrolidino
CO-piperidino
CO-morpholino
CO-pyrrolo
CO—N—(methyl)piperazino
CO—C₆H₅
COCH(CH₃)(CH₂)₂-piperidino Basic esters are obtained as their hydrochloride salts. Careful neutralization with sodium hydroxide affords the free basic esters.

EXAMPLE 64 d,l-trans-5,6,6aβ,7,8,9,10,10aα-Octahydro-1-(4-N-piperidylbutyryloxy)-9-hydroxy-6β-methyl-3-(5-phenyl-2-pentyloxy)benzo[c]quinoline hydrochloride To a 25° C. solution of d,l-trans-5,6,6aβ,7,8,9,10,-10aα-octahydro-1,9-dihydroxy-6β-methyl-3-(5-phenyl-2-pentyloxy)benzo[c]quinoline (1.0 g., 2.53 mmoles) in methylene chloride (20 ml.) is added 4-N-piperidylbutyric acid hydrochloride (0.524 g., 2.53 mmoles) and dicyclohexylcarbodiimide (0.573 g., 2.78 mmoles). The reaction mixture is stirred at 25° C. for 6 hours and then cooled for 12 hours and filtered. Evaporation of the filtrate and trituration of the residue with ether gives 1.3 g. of solid of the monohydrochloride salt.

IR (KBr): 2.95, 3.70, 5.65 (ester C=O), 6.13 and 6.27μ.

Preparative layer chromatography of a portion of this solid on 0.5 mm. thick silica gel and elution with 10% methanol-methylene dichloride affords the free base, d,l-trans-5,6,6aβ,7,8,9,10,10aα-octahydro-1-(4-N-piperidylbutyryloxy)-9-hydroxy-6β-methyl-3-(5-phenyl-2-pentyloxy)benzo[c]quinoline.

¹H NMR (60 MHz) $\delta_{CDCl_3}^{TMS}$(ppm): 1.12 (d, J=7 Hz, C-3 side-chain methyl), 1.25 (d, J=6 Hz, C-6 methyl), 5.84 (s, two ArH) and 7.16 (s, 5H).

Treatment of this free base with excess hydrogen chloride in ether yields the dihydrochloride salt as a hygroscopic powder.

EXAMPLE 65 d,l-5,6,6a,7-Tetrahydro-1-(4-N-piperidylbutyryloxy)-6β-methyl-methyl-3-(5-phenyl-2-pentyloxy)benzo[c]quinolin-9(8H)-one hydrochloride To a 25° C. solution of d,l-5,6,6a,7-tetrahydro-1-hydroxy-6β-methyl-3-(5-phenyl-2-pentyloxy)benzo[c]quinoline-9(8H)-one (550 mg., 1.41 mmole) in methylene chloride (26 ml.) is added 4-N-piperidylbutyric acid hydrochloride (291 mg., 1.41 mmole) and dicyclohexylcarbodiimide (319 mg., 1.55 mmole). This reaction mixture is stirred for 18 hours and is then cooled to 0° C. and filtered. Evaporation of the filtrate and trituration of the residue with ether gives 800 mg. of d,l-5,6,6a,7-tetrahydro-1-(4-N-piperidylbutyryloxy)-6β-methyl-3-(5-phenyl-2-pentyloxy)benzo[c]quinoline-9(8H)-one hydrochloride as a hygroscopic yellow powder.

IR (CHCl₃): 2.92, 4.14 (HN⊕=), 5.69 (ester), 6.00, 6.20 and 6.40μ.

In like manner, d,l-trans-5,6,6aβ,7,8,9,10,10aα-octahydro-1-(4-N-morpholinobutyryloxy)-9-hydroxy-6β-methyl-3-(5-phenyl-2-pentyloxy)benzo[c]quinoline hydrochloride is prepared from 4-N-morpholinobutyric acid and d,l-trans-5,6,6aβ,7,8,9,10,10aα-octahydro-1,9-dihydroxy-6β-methyl-3-(5-phenyl-2-pentyloxy)benzo[c]quinoline:

IR (KBr): 3.00, 3.75, 5.67 (ester C=O), 6.15 and 6.30μ.

Similarly, the remaining compounds of formulae I, II, III and IV described herein are converted to basic esters of the hydroxy group at the 1-position. Esters wherein the $R_1$ moiety has the following values are prepared:
—CON(CH$_3$)$_2$
—CO(CH$_2$)$_2$N(C$_4$H$_9$)$_2$  —CO(CH$_2$)$_3$N(CH$_3$)$_2$  —CO(CH$_2$)$_3$pyrrolidino
—CO(CH$_2$)$_2$—N—(methyl)piperazino
—CO—CH$_2$—pyrrolo

EXAMPLE 66 d,l-7,10-Dihydro-1-hydroxy-3-(2-heptyloxy)-6-methyl-benzo[c]quinolin-9(8H)-one Ethylene Ketal A solution of d,l-7,10-dihydro-1-hydroxy-3-(2-heptyloxy)benzo[c]quinolin-9(8H)-one ethylene ketal (371 mg., 1.0 mmole) in ether (50 ml.) is slowly added to an ice-cold solution of methyl-lithium (44 mg., 2.0 mmole) in ether (25 ml.) The 5-lithio-6-methyl derivative thus obtained is dissolved in dry ether and treated with dry oxygen to give, after filtration and evaporation of the solvent, the title compound.

Hydrolysis of the ketal according to standard procedures affords the 9-ketone.

Repetition of this procedure but using the compounds of Example 57 and the appropriate alkyl lithium, aralkyl lithium reactant or, when $R_4$ is hydrogen, lithium aluminum hydride, affords compounds having the formula

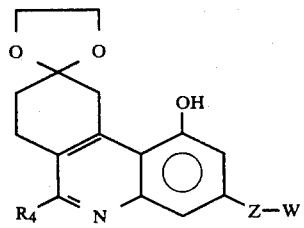

wherein Z and W are as defined in Example 57 and $R_4$ is methyl, n-butyl, n-hexyl, benzyl, phenethyl, 4-phenylbutyl or hydrogen.

EXAMPLE 67

General Hydrochloride Salt Formation

Excess hydrogen chloride is passed into a solution of the appropriate benzo[c]quinoline of formulae I or II and the resulting precipitate separated and recrystallized from an appropriate solvent, e.g. methanol-ether (1:10).

In this manner the following salt is prepared:
d,l-trans-5,6,6aβ,7,8,9,10,10aα-octahydro-1-acetoxy-9β-hydroxy-6β-methyl-3-(5-phenyl-2-pentyloxy)benzo[c]quinoline, m.p. 191°–193° C.
m/e - 437 (m+)
Analysis: Calc'd for C$_{27}$H$_{36}$O$_4$NCl: C, 68.48; H, 7.70; N, 2.89%. Found: C, 68.42; H, 7.66; N, 2.96%.

The remaining compounds of formulae I and II are converted to their hydrochlorides in like manner.

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts are prepared.

EXAMPLE 68

One hundred mg. of d,l-trans-5,6,6aβ,7,8,9,10,10aα-octahydro-1-acetoxy-9-hydroxy-5-methyl-6β-methyl-3-(5-phenyl-2-pentyloxy)benzo[c]quinoline are intimately mixed and ground with 900 mg. of starch. The mixture is then loaded into telescoping gelatin capsules such that each capsule contains 10 mg. of drug and 90 mg. of starch.

EXAMPLE 69

A tablet base is prepared by blending the ingredients listed below:

| | |
|---|---|
| Sucrose | 80.3 parts |
| Tapioca starch | 13.2 parts |
| Magnesium stearate | 6.5 parts |

Sufficient d,l-cis-5,6,6aβ,7,10,10aα-hexahydro-1-acetoxy-6β-methyl-3-(5-phenyl-2-pentyloxy)benzo[c]quinolin-9(8H)-one is blended into this base to provide tablets containing 0.1, 0.5, 1, 5, 10 and 25 mg. of drug.

EXAMPLE 70

Suspensions of d,l-trans-5,6,6aβ,7,8,9,10,10aα-octahydro-1-acetoxy-9-hydroxy-6β-methyl-3-(5-phenyl-2-pentyloxy)benzo[c]quinoline are prepared by adding sufficient amounts of drug to 0.5% methylcellulose to provide suspensions having 0.05, 0.1, 0.5, 1, 5 and 10 mg. of drug per ml.

PREPARATION A

2-Bromo-5-phenylpentane

To phosphorous pentabromide, prepared by addition of bromine (9.0 g.) in methylene chloride (10 ml.) to phosphorous tribromide (15.0 g.) in methylene chloride (15 ml.) at 0° C., is added 5-phenyl-2-pentanol (812 g.) in methylene chloride at 0° C. The mixture is stirred for 2.5 hours at 0° C. and is then allowed to warm to room temperature. Water (50 ml.) is added, the mixture stirred for one hour and the methylene chloride layer separated. The extraction is repeated and the combined extracts washed with water, saturated sodium bicarbonate solution, brine and then dried over magnesium sulfate. Concentration of the dried extracts gives 12.4 g. of title product as a light yellow oil.

NMR: $\delta_{CDCl_3}^{TMS}$ 1.6 (D,3,methyl,J=7 Hz), 1.6–2.0 (M,4,ethylene), 2.3–3.0 (bd,T,2,benzylic-methylene), 3.7–4.2 (M,1,methine), 6.9–7.4(M,5, aromatic).

PREPARATION B 2-(3,5-Dimethoxyphenyl)-5-phenylpentane

A solution of 1-bromopropylbenzene (51.7 g.) in ether (234 ml.) is added dropwise over a 2-hour period to a refluxing mixture of magnesium (7.32 g.) in ether (78 ml.). The reaction mixture is refluxed for 30 minutes longer and then a solution of 3,5-dimethoxy-acetophenone (50 g.) in ether (78 ml.) is added dropwise and heated to reflux for 1.5 hours. The reaction is quenched by addition of saturated ammonium chloride (234 ml.), the ether layer is separated and the aqueous phase extracted with ether (3×200 ml.). The combined ether extracts are dried over magnesium sulfate and concentrated under vacuum to yield 81 g. of an oil. Forty grams of the oil is hydrogenated in a mixture containing ethanol (300 ml.), concentrated hydrochloric acid (2 ml.) and 5% palladium-on-carbon (5 g.). The catalyst is filtered off and the ethanol removed under vacuum. The residue is distilled under vacuum yielding 28 g. of 2-(3,5-dimethoxyphenyl)-5-phenylpentane (b.p. 0.125 mm., 154°–159° C.).

NMR: $\delta_{CDCl_3}^{TMS}$ 1.25 (d,3,α-CH$_3$), 1.3–2.1 (M,4,ethylene), 2.2–2.9 (M,3,benzylic-methylene,methinyl), 3.45 (S,6,methoxyl), 6.2–6.7 (M,3,aromatic), 7.2 (S,5,aromatic).

PREPARATION C

2-(3,5-Dihydroxyphenyl)-5-phenylpentane

A mixture of 2-(3,5-dimethoxyphenyl)-5-phenylpentane (22g.) and pyridine hydrochloride (94 g.) under nitrogen is heated to 190° C. for 2 hours with vigorous stirring. The reaction mixture is cooled, dissolved in 6 N hydrochloric acid (200 ml.) and diluted with water to 600 ml. The aqueous solution is extracted with ethyl acetate (4×100 ml.), the ethyl acetate extracts dried over sodium sulfate and concentrated under vacuum to yield 24 g. of crude product. The product is purified by silica gel chromatography to yield 19.2 g. of 2-(3,5-dihydroxyphenyl)-5-phenylpentane as an oil.

NMR: $\delta_{CDCl_3}^{TMS}$ 1.1 (d,3,α-methyl), 1.35–1.65 (M,4,ethylene), 2.2–2.8 (M,3,benzylic-methylene,methinyl), 6.1–6.5 (M,3,aromatic), 6.65 (bd.S, 2, hydroxyl), 7–7.4 (M,5,aromatic).

Following the procedures of Preparations B and C, the compounds listed below are prepared by substituting the appropriate 1-bromoalkylbenzene for 1-bromopropylbenzene:

2-(3,5-dihydroxyphenyl)-6-phenylhexane—

NMR: $\delta_{CDCl_3}^{TMS}$ 1.1 (D,3,α-methyl, J-7 cps), 1.0–1.9 [M,6,ØCH$_2$(CH$_2$)$_3$CH(CH$_3$)—Ar], 2.2–2.8 (M,3,benzylic methylene,methinyl), 6.0 (bd.S, 2,phenolic OH), 6.2–6.4 (M,3,aromatic), 7.1–7.4 (M,5,aromatic).

1-(3,5-dihydroxyphenyl)-2-phenylethane—
m.p.: 76°–77° C.

2-(3,5-dihydroxyphenyl)-4-phenylbutane (an oil)—

NMR: $\delta_{CDCl_3}^{TMS}$ 1.1, 1.25 (d,2,methyl), 1.45–2.0 (M,2,methylene), 2.15–2.7 (M,3,benzylic-methylene,-methinyl), 6.3 (S,3,aromatic), 6.85 (S,2, hydroxyl-D$_2$O overlay), 7.1 (S,5,aromatic).

The following compounds are prepared in like manner from the appropriate alcohol and 3,5-dimethoxybenzaldehyde or 3,5-dimethoxyacetophenone by the methods of Preparations A, B and C:

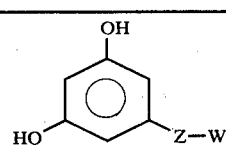

| Z | W |
|---|---|
| CH(CH$_3$)CH$_2$ | C$_5$H$_9$ |
| CH(CH$_3$)(CH$_2$)$_2$ | C$_5$H$_9$ |
| CH(CH$_3$)CH$_2$ | C$_3$H$_5$ |
| CH(CH$_3$)CH(CH$_3$) | C$_6$H$_{11}$ |
| CH(CH$_3$)(CH$_2$)$_3$ | C$_6$H$_{11}$ |

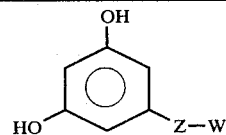

| Z | W |
|---|---|
| CH(CH$_3$)(CH$_2$)$_4$ | C$_5$H$_9$ |
| CH(CH$_3$)(CH$_2$)$_5$ | C$_6$H$_{11}$ |
| CH(C$_2$H$_5$)(CH$_2$)$_2$ | C$_6$H$_{11}$ |
| (CH$_2$)$_3$ | C$_5$H$_9$ |
| CH(C$_2$H$_5$)(CH$_2$)$_3$ | C$_6$H$_5$ |
| C(CH$_3$)$_2$ | C$_6$H$_5$ |
| (CH$_2$)$_4$ | C$_6$H$_5$ |
| (CH$_2$)$_2$CH(C$_2$H$_5$) | C$_6$H$_5$ |
| CH(CH$_3$)CH$_2$CH(C$_2$H$_5$) | C$_6$H$_5$ |

PREPARATION D

1-(3,5-Dihydroxyphenyl)-2-methyl-4-phenylbutane

A solution of n-butyl lithium (29 ml. of 2.2 M) is added dropwise to 3,5-dimethoxybenzyl triphenylphosphonium bromide (31.5 g.) in tetrahydrofuran (200 ml.) with stirring and the resulting deep red solution is stirred for one-half hour. Benzyl acetone (9.4 g.) is added dropwise and the reaction mixture stirred for 12 hours. It is then adjusted to pH 7 by addition of acetic acid and concentrated under reduced pressure. The residue is extracted with methylene chloride and the extract evaporated to give crude 1-(3,5-dimethoxyphenyl)-2-methyl-4-phenyl-1-butene as an oil. It is purified by chromatography on silica gel (400 g.) and elution with benzene. Yield: 10 g. as an oil.

NMR: $\delta_{CDCl_3}^{TMS}$ 1.95 (S,3), 2.3–3.1 (M,4), 3.8 (S,6), 6.15–6.6 (M,3), 7.1–7.5 δ(M,6).

The 1-(3,5-dimethoxyphenyl)-2-methyl-4-phenyl-1-butene (9.4 g.) thus prepared is dissolved in ethanol (250 ml.) and catalytically hydrogenated at 45 p.s.i. in the presence of palladium-on-charcoal (1 g. of 10%) and concentrated hydrochloric acid (1 ml.). Yield: 9.4 g. of 1-(3.5-dimethoxyphenyl)-2-methyl-4-phenylbutane as an oil.

NMR: $\delta_{CDCl_3}^{TMS}$ 0.9 (d,3), 1.35–1.95 (M,3), 2.2–2.9 (M,4), 3.75 (S,6), 6.35 (S,3), 7.25 δ(S,5).

It is demethylated according to the procedure of Preparation C to give 1-(3,5-dihydroxyphenyl)-2-methyl-4-phenylbutane.

The 3,5-dimethoxybenzyl triphenylphosphonium bromide is prepared by refluxing a mixture of 3,5-dimethoxybenzyl bromide (12 g.) and triphenylphosphine (14.2 g.) in acetonitrile (200 ml.) for one hour. The reaction mixture is then cooled and the crystalline product recovered by filtration, washed with ether and dried (20 g.); m.p. 269°–270° C.

PREPARATION E

2-Methyl-2-(3,5-dihydroxyphenyl)-5-phenylpentane

To a solution of the Grignard reagent prepared from 2-phenylbromoethane (5.5 g.), magnesium (0.8 g.) and dry ether (60 ml.) is added a solution of 2-methyl-2-(3,5-dimethoxyphenyl)propionitrile (2.75 g.) in dry ether (20 ml.). The ether is distilled off and replaced by dry benzene (50 ml.) and the mixture refluxed for 48 hours. It is then decomposed by careful treatment with dilute sulfuric acid and heated on a steam bath for one hour. The mixture is then extracted with ether, the extract dried (MgSO$_4$) and concentrated to an oil. Distillation of the oil in vacuo affords 2-methyl-2-(3,5-dimethoxyphenyl)-5-phenyl-3-pentanone; b.p. 168° C./0.2 mm. (Yield: 2.32 g., 60%)

The thus-produced pentanone (58 g.) is dissolved in ethanol (400 ml.) and treated with sodium borohydride (10 g.) at room temperature. The reaction mixture is stirred for 12 hours and is then cooled and neutralized with 6 N hydrochloric acid. The ethanol is removed under reduced pressure and the residue extracted with ether. The extract is dried (MgSO$_4$) and concentrated to give 2-methyl-2-(3,5-dimethoxyphenyl)-5-phenyl-3-pentanol as an oil (52 g., 88% yield).

The pentanol (16 g.) is taken up in ether (100 ml.) and reacted with powdered potassium (2.5 g.) in ether (200 ml.). Carbon disulfide (equimolar to the potassium) is added and the mixture stirred for a half-hour. Methyl iodide (9.0 g.) is then added and the reaction mixture stirred for 6 hours. The resulting suspension is filtered and the filtrate concentrated under reduced pressure. The residue is taken up in ethanol (150 ml.), Raney nickel added (25 g.) and the mixture refluxed for 18 hours. Evaporation of the alcohol and distillation of the residue gives 2-methyl-2-(3,5-dimethoxyphenyl)-5-phenyl-3-pentene.

The pentene derivative is catalytically hydrogenated according to the procedure of Preparation D and the resulting 2-methyl-2-(3,5-dimethoxyphenyl)-5-phenyl-3-pentane demethylated via the procedure of Preparation C to give the product.

PREPARATION F

3,5-Dibenzyloxyacetophenone

Over a period of 1.5 hours, methyl lithium (531 ml. of a 2 molar solution, 1.06 M) is added under a nitrogen atmosphere to a rapidly stirring solution of 3,5-dibenzyloxybenzoic acid (175 g., 0.532 M) in ether (250 ml.)tetrahydrofuran (1400 ml.) maintained at 15°-20° C. After stirring an additional 0.75 hour at 10°-15° C., water (600 ml.) is slowly added keeping the reaction temperature below 20° C. The aqueous layer is separated and extracted with ether (3×250 ml.). The organic phases are combined, washed with saturated sodium chloride solution (4×300 ml.), dried over sodium sulfate, and concentrated under vacuum to give an oil which slowly crystallized from isopropyl ether. The crude product is recrystallized from ether-hexane to yield 104.7 g. (59%) of product; m.p. 59°-61° C.

PREPARATION G

Ethyl 3-(3,5-dibenzyloxyphenyl)crotonate (Wittig Reaction)

A mixture of 3,5-dibenzyloxyacetophenone (43.2 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of triphenyl phosphine oxide removed by filtration. The filtrate is concentrated under vacuum to an oily residue which is chromatographed over silica gel (1500 g.) and eluted with benzene: hexane solutions of increasing benzene concentration beginning with 40:60 and ending with 100% benzene. Concentration of appropriate fractions gives an oily residue which is crystallized from hexane. Yield: 40.2 g. (77%); m.p. 73°-75° C.

Analysis: Calc'd for C$_{26}$H$_{26}$O$_4$: C, 77.58; H, 6.51%. Found: C, 77.72; H, 6.60%.

In like manner, ethyl 3-(3,5-dimethoxyphenyl)crotonate is prepared from 3,5-dimethoxyacetophenone (51.7 g.) and carbethoxymethylene triphenylphosphorane (200 g.). Yield=61.8 g., 86%, b.p. 146°-162° C. at 0.3 mm.).

PREPARATION H

3-(3,5-Dibenzyloxyphenyl)-1-butanol

A solution of ethyl 3-(3,5-dibenzyloxyphenyl)crotonate (24.1 g., 60 mM) in ether (250 ml.) is added to a mixture of lithium aluminum hydride (3.42 g., 90 mM) and ether (250 ml.). Aluminum chloride (0.18 g., 1.35 mM) is added and the mixture refluxed for 12 hours and then cooled. Water (3.4 ml.), sodium hydroxide (3.4 ml. of 6 N) and water (10 ml.) are then added successively to the reaction mixture. The inorganic salts which precipitate are filtered off and the filtrate is then concentrated in vacuo to give the desired alcohol as an oil - 2.4 g. (98%).

R$_f$=0.25 [silica gel:benzene(18):ethyl acetate(1)].
m/e - 362 (m+)

Analysis: Calc'd for C$_{24}$H$_{26}$O$_3$: C, 79.53; H, 7.23%. Found: C, 79.37; H, 7.11%.

In like manner, ethyl 3-(3,5-dimethoxyphenyl)crotonate (60.4 g.) is reduced to 3-(3,5-dimethoxyphenyl)-butanol (48.0 g., 90%).

PREPARATION I

3-(3,5-Dibenzyloxyphenyl)butyl Tosylate

Tosyl chloride (11.1 g., 58.1 mM) is added to a solution of 3-(3,5-dibenzyloxyphenyl)-1-butanol (20.7 g., 57 mM) in pyridine (90 ml.) at −45° C. The reaction mixture is held at −35° C. for 18 hours and is then diluted with cold 2 N hydrochloric acid (1500 ml.) and extracted with ether (5×250 ml.). The combined extracts are washed with saturated sodium chloride solution (4×250 ml.) and then dried (Na$_2$SO$_4$). Concentration of the dried extract affords the product as an oil. It is crystallized by treatment with ether-hexane. Yield: 24.63 g. (84%).

Analysis: Calc'd for C$_{31}$H$_{32}$O$_5$S: C, 72.06; H, 6.24%. Found: C, 72.05; H, 6.29%.

PREPARATION J

3-(3,5-Dibenzyloxyphenyl)-1-phenoxybutane

A solution of phenol (4.56 g., 48.6 mM) in dimethylformamide (40 ml.) is added under a nitrogen atmosphere to a suspension of sodium hydride (2.32 g., 48.6 mM of 50% previously washed with pentane) in dimethylformamide (70 ml.) at 60° C. The reaction mixture is stirred for one hour at 60°-70° C., after which a solution of 3-(3,5-dibenzyloxyphenyl)butyl tosylate (23.93 g., 46.3 mM) in dimethylformamide (80 ml.) is added. The reaction mixture is stirred at 80° C. for a half-hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and then dried (Na$_2$SO$_4$). Removal of the solvent under reduced pressure affords the product as an oil. The oily residue is dissolved in benzene and filtered through silica gel (100 g.). Concentration of the filtrate under reduced pressure gives the product as an oil. Yield: 14.86 g. (73%).

$R_f=0.7$ (silica gel, benzene).

m/e-438 (m+)

Analysis: Calc'd for $C_{30}H_{30}O_3$: C, 82.16; H, 6.89%. Found: C, 82.07; H, 6.84%.

Repetition of Procedures G through J, but using the 3,5-dibenzyloxy derivatives of benzaldehyde, acetophenone or propiophenone, the appropriate carbethoxy (or carbomethoxy) alkylidene triphenyl phosphorane; and the appropriate alcohol, phenol, thiophenol, hydroxypyridine or hydroxypiperidine as reactants affords the following compounds:

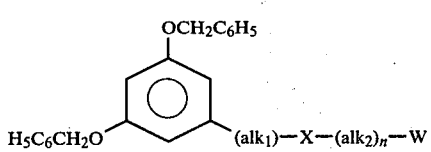

For convenience, the various values of W for given values of $-(alk_1)-X-(alk_2)_n-$ are collectively tabulated.

60 p.s.i. hydrogen in the presence of 10% palladium-on-carbon (1.5 g.). Removal of the catalyst by filtration and concentration of the filtrate gives an oil. The oil is purified by chromatography on silica gel (100 g.) and eluting with benzene-ethyl acetate consisting of 0–10% ethyl acetate. The middle fractions are combined and concentrated to give the title product: 7.8 g. (80%), as an oil.

$R_f=0.25$ [silica gel, benzene(4), methanol(1)].

m/e - 258 (m+)

Analysis: Calc'd for $C_{16}H_{18}O_3$: C, 74.39; H, 7.02%. Found: C, 74.13; H, 7.00%.

In like manner, the remaining ethers (X=O) of Preparation J are debenzylated to afford the corresponding 3,5-dihydroxy derivatives.

The thio ethers are debenzylated by treatment with trifluoroacetic acid. The procedure comprises stirring a solution of the dibenzyl ether (X=S) in trifluoroacetic acid at room temperature for two hours. The reaction mixture is evaporated to dryness and the residue taken up in ether. The ether solution is washed with water, dried (MgSO₄) and evaporated to give the debenzylated compound.

| alk₁ | X | alk₂ | n | W |
|---|---|---|---|---|
| (CH₂)₃ | O | — | 0 | C₆H₅, 4-FC₆H₄, C₄H₇, 4-ClC₆H₄, C₆H₁₁, 4-pyridyl, 3-pyridyl, 4-(C₆H₅)C₆H₁₀, 4-piperidyl, CH₃, 4-(4-FC₆H₄)C₆H₁₀. |
| (CH₂)₃ | O | CH₂ | 1 | C₆H₅, 4-FC₆H₄, C₆H₁₁, 4-piperidyl, CH₃. |
| (CH₂)₃ | O | (CH₂)₂ | 1 | C₆H₅, CH₃, 4-ClC₆H₄, 4-pyridyl. |
| (CH₂)₃ | O | CH(CH₃) | 1 | C₆H₅, 4-FC₆H₄, CH₃, 4-piperidyl, 2-pyridyl. |
| (CH₂)₃ | O | CH(CH₃)(CH₂)₂ | 1 | C₆H₅, 4-pyridyl, CH₃. |
| CH(CH₃)(CH₂)₂ | O | — | 0 | C₆H₅, 4-FC₆H₄, C₆H₁₁, C₃H₅, 4-pyridyl, C₇H₁₃, 3-piperidyl, CH₃, 4-(C₆H₅)C₆H₁₀, 2-(4-ClC₆H₄)C₄H₆. |
| CH(CH₃)(CH₂)₂ | O | CH₂ | 1 | C₆H₅, 4-FC₆H₄, 4-pyridyl, 2-piperidyl, CH₃. |
| CH(CH₃)(CH₂)₂ | O | (CH₂)₂ | 1 | C₆H₅, 4-FC₆H₄, 4-pyridyl, 4-piperidyl, CH₃, C₅H₉. |
| CH(CH₃)(CH₂)₂ | O | (CH₂)₄ | 1 | C₆H₅, 4-pyridyl, 2-piperidyl, CH₃, 4-(C₆H₅)C₆H₁₀. |
| CH(CH₃)(CH₂)₂ | O | (CH₂)₂CH(CH₃) | 1 | C₆H₅, 4-FC₆H₄, CH₃, C₃H₅. |
| CH(CH₃)(CH₂)₂ | O | CH(CH₃) | 1 | C₆H₅, 4-ClC₆H₄, CH₃, 3-piperidyl, C₇H₁₃. |
| CH(CH₃)(CH₂)₂ | O | CH₂CH(C₂H₅) | 1 | C₆H₅, CH₃, C₆H₁₁. |
| CH(C₂H₅)(CH₂)₂ | O | — | 0 | C₆H₅, 4-FC₆H₄, 2-pyridyl, CH₃, 4-piperidyl, C₃H₅, 2-(4-FC₆H₄)C₇H₁₂. |
| CH(C₂H₅)(CH₂)₂ | O | (CH₂)₂ | 1 | C₆H₅, 4-FC₆H₄, 4-pyridyl, C₆H₁₁, 2-piperidyl, CH₃. |
| CH(C₂H₅)(CH₂)₂ | O | (CH₂)₄ | 1 | C₆H₅, 4-FC₆H₄, 4-pyridyl, C₃H₅, C₅H₉. |
| CH(C₂H₅)(CH₂)₂ | O | CH(CH₃) | 1 | C₆H₅, 4-FC₆H₄, CH₃, 4-piperidyl, C₆H₁₁H₅, C₅H₉. |
| CH(C₂H₅)(CH₂)₂ | O | CH(CH₃) | 1 | C₆H₅, 4-FC₆H₄, CH₃, 2-pyridyl, 4-piperidyl, C₆H₁₁. |
| CH(C₂H₅)(CH₂)₂ | O | (CH₂)₂CH(CH₃) | 1 | C₆H₅, 4-FC₆H₄, C₇H₁₃. |
| (CH₂)₄ | O | — | 0 | C₆H₅, 4-FC₆H₄, 4-ClC₆H₄, 4-pyridyl, C₄H₇, 2-piperidyl, CH₃. |
| (CH₂)₄ | O | CH₂ | 1 | C₆H₅, 4-FC₆H₄, 4-pyridyl, 3-pyridyl, 4-piperidyl, CH₃, C₆H₁₁. |
| (CH₂)₄ | O | CH₂CH(CH₃) | 1 | C₆H₅, 4-FC₆H₄, 4-(C₆H₅)C₆H₁₀. |
| (CH₂)₄ | O | CH(CH₃)CH₂ | 1 | C₆H₅, CH₃, 2-pyridyl, 3-piperidyl, 4-piperidyl, 4-FC₆H₄. |
| (CH₂)₄ | O | (CH₂)₅ | 1 | C₆H₅, 4-pyridyl, 3-piperidyl, 4-ClC₆H₄. |
| (CH₂)₃ | S | — | 0 | C₆H₅, 4-FC₆H₄, 4-ClC₆H₄, 4-pyridyl, 2-pyridyl, 2-piperidyl, 4-piperidyl, CH₃, C₃H₅, C₅H₉, C₆H₁₁, 4-(ClC₆H₄)C₆H₁₀. |
| (CH₂)₃ | S | CH₂ | 1 | C₆H₅, 4-FC₆H₄, CH₃, 2-pyridyl, 4-pyridyl, 3-piperidyl, C₅H₉. |
| (CH₂)₃ | S | (CH₂)₂ | 1 | C₆H₅, 4-ClC₆H₄, 4-pyridyl, CH₃, C₃H₅. |
| (CH₂)₃ | S | (CH₂)₄ | 1 | C₆H₅, 4-FC₆H₄, 4-pyridyl, CH₃, 4-piperidyl, C₆H₁₁. |
| CH(CH₃)(CH₂)₂ | S | — | 0 | C₆H₅, 4-FC₆H₄, C₆H₁₁, CH₃, 4-pyridyl, 3-pyridyl, 4-piperidyl, C₃H₇, 4-(C₆H₅)C₆H₁₀. |
| CH(CH₃)(CH₂)₂ | S | CH₂ | 1 | C₆H₅, 4-FC₆H₄, CH₃, 2-pyridyl. |
| CH(CH₃)(CH₂)₂ | S | (CH₂)₂ | 1 | C₆H₅, 4-ClC₆H₄, CH₃, 4-pyridyl, 3-piperidyl. |
| CH(CH₃)(CH₂)₂ | S | (CH₂)₄ | 1 | C₆H₅, CH₃, 4-pyridyl. |
| CH(C₂H₅)(CH₂)₂ | S | — | 0 | C₆H₅, 4-FC₆H₄, 4-(C₆H₅)C₆H₁₀, 4-pyridyl, 3-pyridyl, 2-piperidyl, C₆H₁₁. |
| CH(C₂H₅)(CH₂)₂ | S | CH(CH₃) | 1 | C₆H₅, 4-ClC₆H₄, CH₃, 4-piperidyl. |
| CH(C₂H₅)(CH₂)₂ | S | (CH₂)₂CH(CH₃) | 1 | C₆H₅, CH₃, 4-pyridyl. |
| CH(CH₃)(CH₂)₃ | O | — | 0 | C₆H₅, CH₃, 4-FC₆H₄, 4-pyridyl, C₃H₅, C₇H₁₃, 2-(4-FC₆H₄)C₅H₈. |
| CH(CH₃)(CH₂)₃ | O | (CH₂)₂ | 1 | C₆H₅, CH₃, 3-pyridyl, 4-piperidyl, C₆H₁₁. |
| CH(CH₃)(CH₂)₃ | S | — | 0 | C₆H₅, CH₃, 4-ClC₆H₄, 2-pyridyl, C₆H₁₁, 3-(4-ClC₆H₄)C₆H₁₀. |
| CH(CH₃)(CH₂)₃ | S | (CH₂)₄ | 1 | CH₃, C₆H₅, 4-F₆C₄, 4-pyridyl. |

PREPARATION K

3-(3,5-Dihydroxyphenyl)-1-phenoxybutane

A solution of 3-(3,5-dibenzyloxyphenyl)-1-phenoxybutane (14.7 g., 133.5 mM) in a mixture of ethyl acetate (110 ml.), ethanol (110 ml.) and concentrated hydrochloric acid (0.7 ml.) is hydrogenated for 2 hours under

PREPARATION L

1-Bromo-3-(3,5-dimethoxypheyl)butane

A solution of phosphorous tribromide (5.7 ml., 0.06 mole) in ether (30 ml.) is added to a solution of 3-(3,5- dimethoxyphenyl)-1-butanol (30.0 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried (Na$_2$SO$_4$). Removal of the ether and vacuum distillation of the residue affords the title product; 25 g. (55% yield); b.p. 125°–132° C. at 0.4 mm.

The following compounds are prepared from 3,5-dimethoxybenzaldehyde, 3,5-dimethoxyacetophenone and 3,5-dimethoxypropiophenone and the appropriate carbethoxyalkylidene triphenylphosphorane by the procedures of Preparation G, H and L.

| Z |
| --- |
| (CH$_2$)$_3$ |
| (CH$_2$)$_4$ |
| C(C$_2$H$_5$)CH$_2$ |

PREPARATION M

4-(3,5-Dihydroxyphenyl)-1-(4-pyridyl)pentane

A mixture of 3-(3,5-dimethoxyphenyl)butyl triphenylphosphonium bromide (19.0 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°–5° C. Following completion of addition, the mixture is stirred for one hour at 0°–5° C. and then concentrated under reduced pressure. The concentrate is diluted with water (200 ml.) and then acidified with 6N HCl. The aqueous acid solution is extracted with benzene (4×50 ml.). It is then made basic and extracted with ethyl acetate (3×50 ml.). Evaporation of the combined extracts after drying (MgSO$_4$) affords 4-(3,5-dimethoxyphenyl)-1-(4-pyridyl)-1-pentene (7.1 g., 70%) as an oil.

Catalytic hydrogenation of the thus-produced pentene derivative according to the procedure given in Preparation D gives 4-(3,5-dimethoxyphenyl)-1-(4-pyridyl)pentane in quantitative yield; m.p. 131°–133° C.

The pentane derivative thus obtained is demethylated by heating a mixture of the compound (7.15 g., 25 mmoles) and pyridine hydrochloride (35 g.) under a nitrogen atmosphere at 210° C. for 8 hours. The hot mixture is poured into water (40 ml.) and the resulting solution made basic with 6N sodium hydroxide. Water and pyridine are removed by distillation in vacuo. Ethanol (50 ml.) is added to the residue and the inorganic salts which precipitate are filtered off. The filtrate is concentrated in vacuo and the residue chromatographed on silica gel (150 g.) using as eluting agents 5% ethanol/benzene (4 liters), 10% ethanol/benzene (1 liter), 13% ethanol/benzene (1 liter) and 16% ethanol/benzene (5 liters). The product is isolated as a glassy solid by concentration of appropriate fractions of the eluate. Yield=5.0 g. (78%).

The 3-(3,5-dimethoxyphenyl)butyltriphenylphosphonium bromide is prepared by refluxing a mixture of 1-bromo-3-(3,5-dimethoxyphenyl)butane (21.5 g., 78.5 mmoles) and triphenyl phosphine (20.5 g., 78.5 mmoles) in xylene (60 ml.) for 18 hours. The reaction mixture is then cooled to room temperature and filtered. The filter cake is washed with ether and dried in a vacuum desiccator to give 36.4 g. (86%) yield of product; m.p. 190°–200° C.

Repetition of this procedure but using the appropriate bromo-(3,5-dimethoxyphenyl)alkane and the appropriate aldehyde or ketone affords the following compounds.

| Z | W |
| --- | --- |
| (CH$_2$)$_3$ | 2-pyridyl |
| (CH$_2$)$_3$ | 3-pyridyl |
| (CH$_2$)$_3$ | 4-pyridyl |
| (CH$_2$)$_3$ | 2-piperidyl |
| (CH$_2$)$_3$ | 4-piperidyl |
| (CH$_2$)$_4$ | 2-pyridyl |
| (CH$_2$)$_4$ | 4-pyridyl |
| (CH$_2$)$_4$ | 3-piperidyl |
| (CH$_2$)$_4$ | 4-piperidyl |
| CH$_2$CH(CH$_3$)CH$_2$ | 2-pyridyl |
| CH$_2$CH(CH$_3$)CH$_2$ | 4-piperidyl |
| CH(CH$_3$)CH(CH$_3$)CH$_2$ | 3-pyridyl |
| CH(CH$_3$)CH(CH$_3$)CH$_2$ | 4-pyridyl |
| CH(CH$_3$)CH(CH$_3$)CH$_2$ | 3-piperidyl |
| CH(CH$_3$)(CH$_2$)$_2$ | 2-pyridyl |
| CH(CH$_3$)(CH$_2$)$_2$ | 3-pyridyl |
| CH(CH$_3$)(CH$_2$)$_2$ | 4-piperidyl |
| CH(CH$_3$)(CH$_2$)$_3$ | 3-pyridyl |
| CH(CH$_3$)(CH$_2$)$_3$ | 4-piperidyl |
| CH(CH$_3$)CH(C$_2$H$_5$)CH$_2$ | 4-pyridyl |
| CH(C$_2$H$_5$)(CH$_2$)$_2$ | 2-piperidyl |
| CH(C$_2$H$_5$)(CH$_2$)$_2$ | 4-piperidyl |
| CH$_2$CH(C$_2$H$_5$)CH$_2$ | 3-pyridyl |
| CH(C$_2$H$_5$)(CH$_2$)$_3$ | 3-pyridyl |
| CH(C$_2$H$_5$)(CH$_2$)$_3$ | 4-piperidyl |
| CH(C$_2$H$_5$)CH(CH$_3$)CH$_2$ | 2-pyridyl |
| CH(C$_2$H$_5$)CH(C$_2$H$_5$)CH$_2$ | 4-pyridyl |
| CH(C$_2$H$_5$)CH(C$_2$H$_5$)CH$_2$ | 2-piperidyl |
| (CH$_2$)$_3$ | C$_6$H$_{11}$ |
| CH(CH$_3$)(CH$_2$)$_3$ | C$_6$H$_{11}$ |
| (CH$_2$)$_4$ | C$_3$H$_5$ |
| (CH$_2$)$_2$ | C$_4$H$_7$ |
| CH$_2$CH(CH$_3$)CH$_2$ | C$_5$H$_9$ |
| CH(CH$_3$)(CH$_2$)$_2$ | C$_7$H$_{13}$ |
| CH(CH$_3$)CH(CH$_3$)CH$_2$ | C$_6$H$_{11}$ |
| (CH$_2$)$_6$ | C$_6$H$_5$ |
| (CH$_2$)$_7$ | C$_6$H$_5$ |
| (CH$_2$)$_8$ | C$_6$H$_5$ |
| CH(CH$_3$)(CH$_2$)$_6$ | C$_6$H$_5$ |
| CH(CH$_3$)(CH$_2$)$_7$ | C$_6$H$_5$ |
| CH(CH$_3$)(CH$_2$)$_3$ | 4-FC$_6$H$_4$ |
| C(CH$_3$)$_2$(CH$_2$)$_3$ | C$_6$H$_5$ |
| CH(CH$_3$)(CH$_2$)$_3$ | 4-ClC$_6$H$_4$ |
| CH(CH$_3$)(CH$_2$)$_4$ | 4-ClC$_6$H$_4$ |
| CH(CH$_3$)(CH$_2$) | 4-ClC$_6$H$_4$ |
| CH(CH$_3$)(CH$_2$) | 4-FC$_6$H$_4$ |
| CH(CH$_3$)(CH$_2$)$_2$ | 4-FC$_6$H$_4$ |
| CH(CH$_3$)(CH$_2$)$_2$ | 4-ClC$_6$H$_4$ |
| (CH$_2$)$_3$CH(CH$_3$) | C$_6$H$_{11}$ |
| CH(CH$_3$)(CH$_2$)$_2$CH(CH$_3$) | C$_6$H$_5$ |
| CH(CH$_3$)(CH$_2$)$_2$CH(CH$_3$) | C$_6$H$_{11}$ |
| CH(CH$_3$)(CH$_2$)$_2$CH(CH$_3$) | 4-piperidyl |
| CH(CH$_3$)(CH$_2$)$_3$ | C$_6$H$_{11}$ |
| CH(CH$_3$)(CH$_2$)$_2$CH(CH$_3$) | C$_6$H$_{11}$ |
| (CH$_2$)$_3$ | C$_6$H$_{11}$ |

-continued

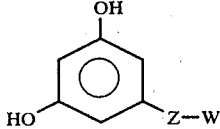

| Z | W |
|---|---|
| (CH$_2$)$_4$ | C$_6$H$_{11}$ |
| (CH$_2$)$_8$ | C$_6$H$_{11}$ |

PREPARATION N

3,5-Dimethoxy-α-methylstyrene Oxide

To a solution of dimethylsulfoxonium methylide (69.4 mM) in dimethyl sulfoxide (65 ml.) at room temperature is added solid 3,5-dimethoxyacetophenone (10 g., 55.5 mM). The reaction mixture is stirred for one hour at 25° C., for one-half hour at 50° C. and is then cooled. The mixture is diluted with water (50 ml.) and added to a mixture of ice water (200 ml.)—ether (250 ml.)—low boiling petroleum ether (25 ml.). The organic extract is washed twice with water (250 ml.), dried (MgSO$_4$) and evaporated to an oil. Fractional distillation of the oil yields 8.0 g. (75%) of 3,5-dimethoxy-α-methylstyrene oxide, b.p. 93°-97° C., 0.2 mm.

IR (CCl$_4$): 2780, 1595, 1196, 1151, 1058 cm$^{-1}$.
UV (95% ethanol): λ$_{max}$=279 nm (ε=2068).
m/e - 194 (m+)
PMR (CDCl$_3$) (60 MHz): δ1.70 (S,CH$_3$—), 2.76 (d,J = 6 Hz, —CH(O)—H), 2.95 (d,J = 6Hz, —CH(O)—H), 3.81 (S,CH$_3$O—), 6.41 (t,J=2Hz, ArH) and 6.58 (d,J=2Hz, ArH).

Analysis: Calc'd for C$_{11}$H$_{14}$O$_3$: C, 68.02; H, 7.27%. Found: C, 67.96; H, 7.28%.

PREPARATION O

2-(3,5-Dimethoxyphenyl)-2-hydroxypropyl-2-phenylethyl Ether

A mixture of dry 2-phenylethanol (30 ml., 251 mM) and sodium metal (690 mg., 30 mM) is heated at 110° C. for 30 minutes. The resulting 1M solution of sodium 2-phenylethoxide is cooled to 60° C., 3,5-dimethoxy-α-methylstyrene oxide (2 g., 10.3 mM) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. −65° C., 0.1 mm) leaving a 3.5 g. residue. The residue is purified via column chromatography on Merck silica gel 60 (300 g.) and eluted in 15 ml. fractions with 60% ether-pentane. Fractions 52–88 yielded 2.9 g. (89%) of 2-(3,5-dimethoxyphenyl)-2-hydroxypropyl 2-phenylethyl ether.

IR (CCl$_4$): 3534, 1595, 1202, 1153 cm$^{-1}$.
UV (95% ethanol): λ$_{max}$=278 (ε=1830), 273 (ε=1860).
m/e - 316 (m+)
PMR (CDCl$_3$, 60 MHz): δ1.46 (S,CH$_3$—), 2.86 (S,OH), 2.86 (t,J=7Hz, —CH$_2$—Ph), 3.53 (S,—CH$_2$O), 3.71 (t,J=7Hz,—CH$_2$O), 3.80 (S,OCH$_3$), 6.38 (t,J=2Hz, ArH), 6.61 (d,J=2Hz, ArH) and 7.23 (S,PhH).

Analysis: Calc'd for C$_{19}$H$_{24}$O$_4$: C, 72.12; H, 7.65%. Found: C, 71.92; H, 7.63%.

PREPARATION P

2-(3,5-Dimethoxyphenyl)propyl 2Phenylethyl Ether

To a 0° C. solution of 2-(3,5-dimethoxyphenyl)-2-hydroxypropyl 2-phenylethyl ether (550 mg., 1.74 mM) in pyridine (2 ml.) is added dropwise phosphorous oxychloride (477 ml., 5.22 mM). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3×50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases (26.5 ml., 20 min.), the reaction is filtered through diatomaceous earth and the filtrate evaporated to an oil. The oil is purified via preparative layer chromatography on silica gel plates, eluted twice with 6:1 pentane:ether to yield 211 mg. (40%) of 2-(3,5-dimethoxyphenyl)propyl 2-phenylethyl ether.

IR (CCl$_4$): 1600, 1205, 1155, 1109 cm$^{-1}$.
m/e - 300 (m+)
PMR (CDCl$_3$,60MHz) δ1.22 (d,J=7Hz, CH$_3$—), 2.82 (t,J=7Hz, CH$_2$Ph), −2.8 (H—C—Me), −3.6 (—CH$_2$—O—CH$_2$—), 3.75 (S,OCH$_3$), 6.35 (m,ArH) and 7.18 (S,PhH).

PREPARATION Q

2-(3,5-Dihydroxyphenyl)propyl 2-Phenylethyl Ether

A mixture of 2-(3,5-dimethoxyphenyl)propyl 2-phenylethyl ether (195 mg., 0.65 mM), pyridine (0.4 ml., 4.96 mM) and dry pyridine hydrochloride (4 g., 34.6 mM) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield 65.8 mg. (37%) of 2-(3,5-dihydroxyphenyl)propyl 2-phenylethyl ether.

IR (CHCl$_3$): 3559, 3279, 1605, 1147, 1105 cm$^{-1}$.
m/e - 272 (m+)
PMR (CDCl$_3$, 60 MHz) δ1.18 (d,J=7Hz, CH$_3$—), 2.80 (t,J=7Hz, —CH$_2$Ph), 2.80 (H—C—Me), 3.4–3.8 (—CH$_2$OCH$_2$—), 6.08 (t,J=2Hz, ArH), 6.21 (d,J=2Hz, ArH) and 7.16 (S,PhH).

The following compounds are prepared from appropriate alkanols by the methods of Procedures O and P.

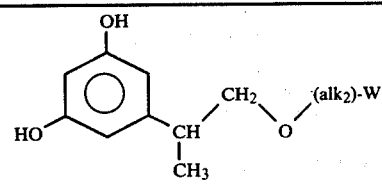

| (alk₂) | W |
|---|---|
| —(CH₂)₆— | CH₃ |
| —(CH₂)₆— | C₆H₅ |
| —(CH₂)₄— | CH₃ |
| —CH(CH₃)CH₂— | CH₃ |
| —CH(CH₃)(CH₂)₄— | CH₃ |
| —(CH₂)— | 4-FC₆H₄ |
| —(CH₂)₂— | 4-pyridyl |
| —(CH₂)₂— | 2-piperidyl |
| —CH(CH₃)CH₂— | 4-piperidyl |
| —(CH₂)₂CH(CH₃)(CH₂)₂— | CH₃ |
| —CH(CH₃)— | CH₃ |
| —C(CH₃)₂— | CH₃ |

PREPARATION R

4-(3,5-Dihydroxyphenyl)-1-phenoxypentane

Under a nitrogen atmosphere a mixture of 3,5-dibenzyloxyacetophenone (50.0 g., 0.15 M) in tetrahydrofuran (175 ml.) and 3-phenoxypropyltriphenylphosphonium bromide (7.18 g., 0.15 M) in dimethylsulfoxide (450 ml.) is added dropwise over 1.75 hours to a suspension of 50% sodium hydride (7.89 g., 0.165 M) (previously washed with pentane) in tetrahydrofuran (75 ml.) maintained at 0°–5° C. After stirring for 4 hours at 0°–5° C. the reaction is allowed to warm to room temperature and is then carefully stirred into ice water (2000 ml.), acidified with concentrated hydrochloric acid, and extracted with ethyl acetate (5×400 ml.). The combined organic phases are washed with saturated sodium chloride solution (3×300 ml.), dried over sodium sulfate and concentrated under vacuum to yield an oil which is triturated with ether to precipitate triphenylphosphine oxide. Filtration, followed by concentration of the filtrate, gives an oily residue which is chromatographed over silica gel (1300 g.) eluting with benzene-hexane consisting of 30% to 100% benzene. From the middle fractions 51 g. (75%) of 4-(3,5-dibenzyloxyphenyl)-1-phenoxypent-3-ene is isolated as an oil; $R_f$=0.8 (silica gel, 2-benzene:1-hexane); m/e - 450 (m⁺).

Analysis: Calc'd for $C_{31}H_{30}O_3$: C, 82.63; H, 6.71%. Found: C, 82.90; H, 6.69%.

A solution of 4-(3,5-dibenzyloxyphenyl)-1-phenoxypent-3-ene (51 g., 0.113 M) in a mixture of absolute ethanol (160 ml.), ethyl acetate (160 ml.) and concentrated hydrochloric acid (0.2 ml.) is hydrogenated for 12 hours under 55 lbs. hydrogen in the presence of 10% Pd/C. Removal of the catalyst by filtration and concentration of the filtrate under vacuum yields 30.8 g. (100%) of product as a viscous oil.

Analysis: Calc'd for $C_{17}H_{20}O_3$: C, 74.97; H, 7.40%. Found: C, 74.54; H, 7.45%.

PREPARATION S

3,5-Dimethoxy-β-methylstyrene oxide

To a −78° C. solution of diphenylsulfonium ethylide (1.0 mole) in tetrahydrofuran (one liter) is slowly added 3,5-dimethoxybenzaldehyde (1.0 mole). The reaction mixture is stirred at −78° C. for 3 hours and then allowed to warm to room temperature. It is then added to ether-water and the ether phase separated. The ether phase is washed with water, dried (MgSO₄) and evaporated. Fractional distillation of the residue gives the title product.

PREPARATION T

3-(3,5-Dihydroxphenyl)-2-propylbutyl Ether

To a solution of sodium butoxide in butanol (0.5 liters of 1M) is added 3,5-dimethoxy-β-methylstyrene oxide (6.33 M). The mixture is heated for 18 hours at 70° C. and is then cooled and added to a mixture of ether-water. The ether solution is separated, dried (MgSO₄) and evaporated to give 3-(3,5-dimethoxyphenyl)-3-hydroxy-2-propylbutyl ether. It is purified by column chromatography on silica gel with ether-pentane elution.

By means of the procedure of Preparation P the title product is produced.

Similarly, the following are prepared from appropriate alcohols:

| (alk₂) | W |
|---|---|
| CH₂ | CH₃ |
| (CH₂)₆ | CH₃ |
| (CH₂)₃ | C₆H₅ |
| (CH₂)₂ | 4-FC₆H₄ |
| (CH₂)₂ | 4-pyridyl |
| CH(CH₃)CH₂ | CH₃ |
| CH(C₂H₅)—(CH₂)₂ | CH₃ |
| CH(CH₃)CH₂ | C₆H₅ |

PREPARATION U

Alkylation of 3,5-Dihydroxyphenylmercaptan

A solution of 3,5-dihydroxyphenylmercaptan (3.5 g., 0.01 mole) in absolute ethanol (50 ml.) is made just alkaline with sodium ethoxide. The appropriate bromide of formula Br-(alk₂)ₙ-W (0.01 mole) is added and the mixture refluxed for 3 hours. It is then concentrated under reduced pressure and the residue extracted with ether. Evaporation of the ether affords the product.

The following compounds are thus prepared:

| n | (alk₂) | W |
|---|---|---|
| 1 | —CH(CH₃)(CH₂)₅— | CH₃ |
| 1 | —CH(CH₃)CH(CH₃)(CH₂)₄— | CH₃ |
| 1 | —C(CH₃)₂(CH₂)₅— | CH₃ |
| 1 | —(CH₂)₈— | CH₃ |
| 1 | —(CH₂)₄— | CH₃ |
| 1 | —CH₂— | C₆H₅ |
| 1 | —(CH₂)₂— | C₆H₅ |
| 1 | —CH(CH₃)(CH₂)₃— | C₆H₅ |
| 1 | —CH₂— | C₃H₅ |
| 1 | —CH₂— | C₅H₉ |
| 1 | —CH₂— | C₆H₁₁ |
| 1 | —(CH₂)₂— | C₅H₉ |

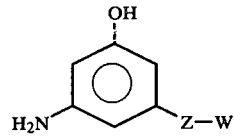

| n | (alk₂) | W |
|---|---|---|
| 1 | —(CH₂)₃— | C₅H₉ |
| 1 | —(CH₂)₅— | C₆H₁₁ |
| 1 | —(CH₂)₄— | C₅H₉ |
| 1 | —(CH₂)₃CH(C₂H₅)— | C₆H₁₁ |
| 1 | —(CH₂)₇— | C₅H₉ |
| 1 | —(CH₂)₄— | C₇H₁₃ |
| 1 | —(CH₂)₂— | C₇H₁₃ |
| 1 | —(CH₂)₅— | C₄H₇ |
| 1 | —(CH₂)₅— | C₃H₅ |
| 1 | —(CH₂)— | 2-piperidyl |
| 1 | —(CH₂)₃— | 4-piperidyl |
| 1 | —(CH₂)— | 2-pyridyl |
| 1 | —(CH₂)₃— | 3-pyridyl |
| 1 | —(CH₂)₄— | 2-pyridyl |
| 1 | —CH(CH₃)(CH₂)₂— | 2-pyridyl |
| 1 | —CH(CH₃)(CH₂)₃— | 4-pyridyl |
| 1 | —CH(C₂H₅)(CH₂)₂— | 4-piperidyl |
| 1 | —(CH₂)₄— | 4-FC₆H₄ |
| 1 | —CH(CH₃)(CH₂)₂— | 4-ClC₆H₄ |
| 1 | —CH(CH₃)(CH₂)₃— | 4-FC₆H₄ |
| 0 | — | C₆H₅ |
| 0 | — | 4-FC₆H₄ |
| 0 | — | 4-ClC₆H₄ |
| 0 | — | C₃H₅ |
| 0 | — | C₅H₉ |
| 0 | — | C₆H₁₁ |
| 0 | — | C₇H₁₃ |
| 0 | — | 4-pyridyl |
| 0 | — | 2-piperidyl |
| 0 | — | 2-pyridyl |
| 0 | — | 2-(C₆H₅)C₃H₄ |
| 0 | — | 4-(C₆H₅)C₆H₁₀ |
| 0 | — | 3-(C₆H₅)C₇H₁₂ |
| 0 | — | CH₃ |

PREPARATION V

3-Hydroxy-5-pentylaniline

Olivetol (1.8 g., 0.01M), ammonium chloride (2.65 g., 0.05M), sodium bisulfite (5.2 g., 0.05M) and ammonium hydroxide (12.5 ml.) are combined and heated in a steel bomb at 230° C. for a half-hour. The bomb is then cooled, the contents dissolved in ethyl acetate (350 ml.). Hydrochloric acid (300 ml. of 10%) is added, the mixture stirred and then the organic layer separated. The extraction is repeated two more times. The aqueous acid solution is neutralized with 6N sodium hydroxide and then extracted with chloroform (3×300 ml.). The combined chloroform extracts are dried and concentrated. The residue is taken up in ethyl acetate, decolorized with charcoal and concentrated. The addition of hexane to the residue causes it to crystallize: 270 mg.; m.p. 88°–91° C. When recrystallized from hot ethyl acetate-hexane (1—1) it melts at 95°–96° C.

Analysis: Calc'd for $C_{11}H_{17}ON$: C, 73.70; H, 9.56; N, 7.81%. Found: C, 73.64; H, 9.62; N, 7.91%.

In like manner, the compounds of Preparations C, D, E, K, M, Q, R, T, U and CC are converted to the corresponding aniline derivatives having the formula wherein Z and W are as defined in said Preparations.

PREPARATION W d,l-N-Acetyl-3-hydroxy-5-(5-phenyl-2-pentyl)aniline

A solution of 2.4 g. (9.5 mmole) d,l-3-hydroxy-5-(5-penyl-2-pentyl)aniline in 24 ml. pyridine and 24 ml. acetic anhydride is stirred at room temperature for 45 minutes. The reaction mixture is poured onto 200 ml. each of water and ethyl acetate. After stirring for 10 minutes, the organic layer is separated and washed successively with water (4×100 ml.), brine (1×100 ml.), dried (MgSO₄), filtered and concentrated to yield 3.5 g. of crude d,l-N-acetyl-3-acetoxy-5-(5-phenyl-2-pentyl)aniline. A solution of d,l-N-acetyl-3-acetoxy-5-(5-phenyl-2-pentyl)aniline and 1 g. potassium carbonate in 100 ml. methanol is stirred at room temperature for one hour, filtered, concentrated and dissolved in ethyl acetate. The organic solution is washed with water, dried (MgSO₄) and concentrated to an oil which is crystallized from hexane to yield 1.5 g. d,l-N-acetyl-3-hydroxy-5-(5-phenyl-2-pentyl)aniline, m.p. 128°–130° C.

m/e - 297 (m+)

$^1$H MNR (60 MHz) $\delta_{CDCl_3}^{TMS}$ (ppm): 8.64 (bs, 1H, —NH), 7.12, 6.58 and 6.45 (bs, 1H variable, ArOH), 2.19–2.78 (m, 3H, Ar—CH and Ar—CH₂), 2.05 (s, 3H, CH₃—C(=O)—), 1.3–1.78 (m, 4H, (CH₂)₂), 1.12 (d, 3H, —C—CH₃).

PREPARATION X d,1-3-Benzyloxy-5-(5-phenyl-2-pentyl)aniline

To a stirred solution of 1.2 g. d,1-N-acetyl-3-hydroxy-5-(5-phenyl-2-pentyl)aniline (4.03 mmole) in 50 ml. tetrahydrofuran is added 193 mg. of 50% sodium hydride (4.03 mmole). After 30 minutes of stirring, 1.38 g, (8.06 mmole) of α-bromotoluene is added and stirring continued for 16 hours. The reaction mixture is then filtered, 1 ml. of acetic acid added to the filtrate which is then concentrated and chromatographed (silica gel, benzene/ether [2:1] as eluent) to yield 1.43 g. d,1-N-acetyl-3-benzyloxy-5-(5-phenyl-2-pentyl)aniline as an oil.

m/e—387 (m+)

$^1$H NMR (60 MHz) $\delta_{CDCl_3}^{TMS}$ (ppm): 7.88 (bs, 1H, N—H), 7.38, 7.20, 6.84, 6.59 (bs, 5H, 6H, 1H, 1H, aromatic), 5.0 (s, 2H, —O—CH₂Ar), 2.21–2.98 (m, 3H, Ar—CH and Ar—CH₂), 2.07 (s, 3H, CH₃—C(=O)—N), 1.30–1.69 (m, 4H, —(CH₂)₂), 1.15 (d, 3H, CH₃—C—Ar).

A solution of 1.4 g. d,1-N-acetyl-3-benzyloxy-5-(5-phenyl-2-pentyl)aniline, 14 ml. 20% potassium hydroxide, 14 ml. methanol and 10 ml. 2-propanol is heated at reflux on a steam bath for 4 days. After cooling, water and ethyl acetate are added and the mixture stirred for 10 minutes. The organic phase is separated and the aqueous phase extracted again with ethyl acetate. The organic solutions are combined, dried (MgSO₄), concentrated in vacuo and chromatographed (35 g. silica gel, benzene/ether [3:1] as eluent) to yield d,1-3-benzyloxy-5-(5-phenyl-2-pentyl)aniline as an oil.

m/e - 345 (m+)

$^1$H NMR (60 MHz) $\delta_{CDCl_3}^{TMS}$ (ppm): 7.32 (bs, 5H, aromatic), 7.13 (bs, 5H, aromatic), 6.01–6.33 (m, 3H, aromatic), 4.95 (s, 2H, ArCH$_2$O), 3.48 (bs, 2H variable, NH$_2$), 2.17–2.88 (m, 3H, Ar—CH and Ar—CH$_2$), 1.32–1.76 (m, 4H, (CH$_2$)$_2$), 1.14 (d, 3H, —C—CH$_3$).

Following the procedures of Preparations W and X, the 3-hydroxy-5-(Z-W)-anilines of Preparation V are converted to 3-benzyloxy-5-(Z-W)anilines wherein Z and W are as defined in Preparation V.

PREPARATION Y d,1-3-Methoxy-5-(5-phenyl-2-pentyl)aniline

The procedures of Preparations W and X are repeated but using methyl bromide in place of α-bromotoluene to give the title product.

Similarly, the compound of Preparation V are reacted with methyl bromide or ethyl bromide to give compounds having the formula

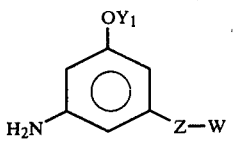

wherein Z and W are as defined in Preparation V and Y$_1$ is methyl or ethyl.

PREPARATION Z 3,5-Diethoxyaniline

A mixture of 3-ethoxy-5-hydroxynitrobenzene (8.7 g.), diethyl sulfate (9.1 g), potassium carbonate (7.4 g) and toluene (200 ml) is heated at reflux for four hours. The toluene is removed by steam distillation and the residue cooled. The solid product 3,5-diethoxy nitrobenzene is recovered by filtration and dried.

The solid (11 g.) is dissolved in glacial acetic acid (100 ml.) and water (100 ml). Tin (1 g.) is added, followed by a solution of stannous chloride (7 g.) in concentrated hydrochloric acid (70 ml.). The mixture is stirred vigorously and held at 40° C. for six hours. It is then made alkaline with sodium hydroxide and extracted with ether (3×100 ml.). The combined extracts are dried (Na$_2$SO$_4$) and evaporated to give the product. It is purified by vacuum distillation.

PREPARATION AA (2-Halophenyl)cycloalkanols

The procedure of Huitric et al., *J. Org. Chem.*, 23, 715–9 (1962) is employed but using the appropriate cycloalkylene oxide and p-halo (Cl or F) phenyl lithium reactants to produce the following compounds.

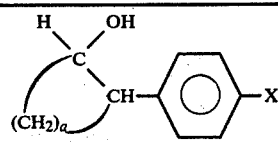

| a | X | a | X |
|---|---|---|---|
| 2 | Cl | 2 | F |
| 3 | Cl | 3 | F |

-continued

| a | X | a | X |
|---|---|---|---|
| 5 | Cl | 5 | F |

PREPARATION BB (4-Halophenyl)cyclohexanols

A. 3- and 4-(4-Fluorophenyl)cyclohexanols

A benzene solution containing equimolar amounts of 4-fluorostyrene and 2-methoxybutadiene and hydroquinone (1% by weight based on diene) is heated in a sealed tube at 150° C. for 10 hours. The reaction vessel is cooled, the contents removed and concentrated to give 1-methoxy-4-(and 5)-4-(fluorophenyl)cycloheptene which are separated by distillation in vacuo. Hydrolysis of the ether with 3% hydrochloric acid affords 3- and 4-(4-fluorophenyl)cyclohexanones.

Sodium borohydride reduction of the ketones according to the procedure of Example 31 affords the hydroxy compounds.

In like manner, the corresponding 3- and 4-(4-chlorophenyl)cyclohexanols are prepared from 4-chlorostyrene.

B. 2-(4-Fluorophenyl)cyclohexanol

This compound is prepared from cyclohexane oxide and p-fluorophenyl lithium according to the procedure of Huitric et al., *J. Org. Chem.*, 27, 715–9 (1962), for preparing 2-(4-chlorophenyl)cyclohexanol.

PREPARATION CC

Alkylation of 3,5-Dihydroxyphenylmercaptan

A solution of 3,5-dihydroxyphenylmercaptan (3.5 g., 0.01 mole) in absolute ethanol (50 ml.) is made just alkaline with sodium ethoxide. The appropriate bromide of formula Br-(alk$_2$)$_n$-W (0.01 mole) is added and the mixture refluxed for 3 hours. It is then concentrated under reduced pressure and the residue extracted with ether. Evaporation of the ether affords the product.

The following compounds are thus prepared:

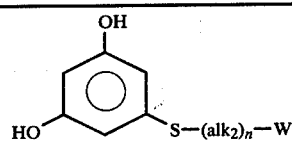

| n | (alk$_2$) | W |
|---|---|---|
| 1 | —CH(CH$_3$)(CH$_2$)$_6$— | H |
| 1 | —CH(CH$_3$)CH(CH$_3$)(CH$_2$)$_4$— | CH$_3$ |
| 1 | —C(CH$_3$)$_2$(CH$_2$)$_5$— | CH$_3$ |
| 1 | —(CH$_2$)$_8$— | CH$_3$ |
| 1 | —(CH$_2$)$_4$— | CH$_3$ |
| 1 | —CH$_2$— | C$_6$H$_5$ |
| 1 | —(CH$_2$)$_2$— | C$_6$H$_5$ |
| 1 | —CH(CH$_3$)(CH$_2$)$_3$— | C$_6$H$_5$ |
| 1 | —CH$_2$— | C$_3$H$_5$ |
| 1 | —CH$_2$— | C$_5$H$_9$ |
| 1 | —CH$_2$— | C$_6$H$_{11}$ |
| 1 | —(CH$_2$)$_2$— | C$_5$H$_9$ |
| 1 | —(CH$_2$)$_5$— | C$_6$H$_{11}$ |
| 1 | —(CH$_2$)$_4$— | C$_5$H$_9$ |
| 1 | —(CH$_2$)$_3$CH(C$_2$H$_5$)— | C$_6$H$_{11}$ |

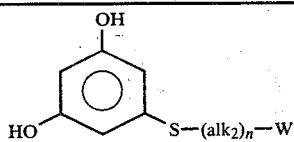

| n | (alk₂) | W |
|---|---|---|
| 1 | —(CH₂)₇— | C₅H₉ |
| 1 | —(CH₂)₄—C₇H₁₃ | |
| 1 | —(CH₂)₂— | C₇H₁₃ |
| 1 | —(CH₂)₅— | C₄H₇ |
| 1 | —(CH₂)₅— | C₃H₅ |
| 1 | —(CH₂)— | 2-piperidyl |
| 1 | —(CH₂)₃— | 4-piperidyl |
| 1 | —(CH₂)— | 2-pyridyl |
| 1 | —(CH₂)₃— | 3-pyridyl |
| 1 | —(CH₂)₄— | 2-pyridyl |
| 1 | —CH(CH₃)(CH₂)₂— | 2-pyridyl |
| 1 | —CH(CH₃)(CH₂)₃— | 4-pyridyl |
| 1 | —CH(C₂H₅)(CH₂)₂— | 4-piperidyl |
| 1 | —(CH₂)₄— | 4-FC₆H₄ |
| 1 | —CH(CH₃)(CH₂)₂— | 4-ClC₆H₄ |
| 1 | —CH(CH₃)(CH₂)₃— | 4-FC₆H₄ |
| 0 | — | C₆H₅ |
| 0 | — | 4-FC₆H₄ |
| 0 | — | 4-ClC₆H₄ |
| 0 | — | C₃H₅ |
| 0 | — | C₅H₉ |
| 0 | — | C₆H₁₁ |
| 0 | — | C₇H₁₃ |
| 0 | — | 4-pyridyl |
| 0 | — | 2-piperidyl |
| 0 | — | 2-pyridyl |
| 0 | — | 2-(C₆H₅)C₃H₄ |
| 0 | — | 4-(C₆H₅)C₆H₁₀ |
| 0 | — | 3-(C₆H₅)C₇H₁₂ |
| 0 | — | CH₃ |

PREPARATION DD d,1-5-Phenyl-2-Pentanol Mesylate

To a stirred solution of 5-phenyl-2-pentanol (482 g.; 2.94 moles) in tetrahydrofuran (2250 ml.) at 0° C. is added methanesulfonyl chloride (300 ml.) at such a rate that the internal temperature does not rise above 10° C. (total addition time 4.5 hours). After addition is complete, the reaction mixture is allowed to warm to room temperature and stirring is continued for an additional hour. The reaction mixture is filtered and the supernate concentrated to a light yellow oil (2800 g.) which is dissolved in chloroform (2 l.) and washed with water (4×1 l.), brine (1×1 l.), charcoal treated (50 g.) dried (MgSO₄), filtered through diatomaceous earth and concentrated to a light orange oil (687 g., 95% yield). This material is suitable for use without further purification.

¹H NMR (60 MHz) $\delta_{CDCl_3}^{TMS}$ (ppm): 7.23 (s, 5H, aromatic), 4.53–5.13 (m, 1H, —CH—O—), 2.93 (s, 3H, O—SO₂—CH₃), 2.42–2.93 (m, 2H, —CH₂C₆H₅), 1.50–1.92 (m, 4H, —(CH₂)₂—), 1.23 (s, 3H, O—CH—CH₃).

Similarly, the following mesylates are prepared from appropriate alcohols:

4-phenybutanol mesylate, a yellow oil.
m/e - 228 (m⁺)

¹H NMR (60 MHZ) $\delta_{CDCl_3}^{TMS}$ (ppm): 7.22 (bs, 5H, aromatic), 4.08–4.34 (m, 2H, —CH₂—O—), 3.93 (s, 3H, SO₂CH₃), 2.40–2.82 (m, 2H, —CH₂C₆H₅), 1.51–1.93 (m, 4H, —(CH₂)₂—).

1-2-octanol mesylate, a colorless oil.
$[\alpha]_D^{25} = -9.695°$ (C - 2.6, CHCl₃)

¹H NMR (60 MHz) $\delta_{CDCl_3}^{TMS}$ (ppm): 4.79 (bg, 1H, —CH—O—), 2.97 (s, 3H, S—CH₃), 1.40 (d, 3H, CH₃—CH), 0.87 (t, 3H, CH₃—CH₂), 1.0–2.0 (m, 10 H, —(CH₂)₅—).

d-2-octanol mesylate.
$[\alpha]_D^{25} = +9.238°$ (C=2.8, CHCl₃)
¹H NMR, identical to the 1-form.

I claim:

1. A compound having the formula:

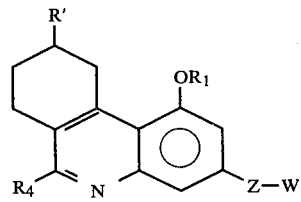

wherein R' is selected from the group consisting of hydroxy; alkanoyloxy having from one to five carbon atoms; hydroxymethyl; oxo, methylene and alkylenedioxy having from two to four carbon atoms;

R₁ is selected from the group consisting of hydrogen, benzyl, benzoyl, alkanoyl having from one to five carbon atoms and —CO—(CH₂)ₚ—NR₂R₃ wherein p is 0 or an integer from 1 to 4; each of R₂ and R₃ when taken individually is selected from the group consisting of hydrogen and alkyl having from one to four carbon atoms; R₂ and R₃ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

R₄ is selected from the group consisting of hydrogen, alkyl having from 1 to 6 carbon atoms and —(CH₂-)z—C₆H₅ wherein z is an integer from 1 to 4;

Z is selected from the group consisting of (a) alkylene having from one to nine carbon atoms;

(b) -(alk₁)ₘ-X-(alk₂)ₙ—wherein each of (alk₁) and (alk₂) is alkylene having from one to nine carbon atoms, with the proviso that the summation of carbon atoms in (alk₁) plus (alk₂) is not greater than nine; each of m and n is 0 or 1; X is selected from the group consisting of O, S, SO and SO₂; and W is selected from the group consisting of hydrogen, methyl, pyridyl, piperidyl,

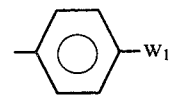

wherein W₁ is selected from the group consisting of hydrogen, fluoro and chloro; and

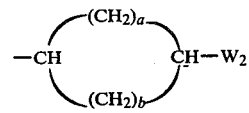

wherein W₂ is selected from the group consisting of hydrogen and

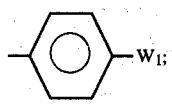

a is an integer from 1 to 5 b is 0 or an integer from 1 to 5; with the proviso that the sum of a and b is not greater than 5.

2. A compound according to claim 1 wherein R' is alkylenedioxy; $R_1$ is hydrogen; $R_4$ is methyl or hydrogen; Z is -(alk$_1$)$_m$-O-(alk$_2$)$_n$- and W is hydrogen or phenyl.

3. A compound according to claim 2 wherein R' is ethylenedioxy; Z is -O-(alk$_2$)$_n$-; W is phenyl and $R_4$ is hydrogen.

4. The compound according to claim 3, wherein Z is —O—CH(CH$_3$)(CH$_2$)$_3$—.

5. A compound according to claim 2 wherein R' is ethylenedioxy; Z is -O-(alk$_2$)$_n$- and each of $R_4$ and W is hydrogen.

6. The compound according to claim 5 wherein Z is —O—CH(CH$_3$) (CH$_2$)$_5$—.

7. A process for producing analgesia in a mammal which comprises administering to the mammal an analgesic producing quantity of a compound selected from the group consisting of those having the formula

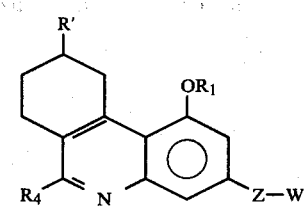

and the pharmaceutically acceptable acid addition salts thereof,
wherein
$R_1$ is selected from the group consisting of hydrogen, benzoyl, alkanoyl having from one to five carbon atoms and —CO—(Ch$_2$)$_p$—NR$_2$R$_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;
$R_4$ is selected from the group consisting of hydrogen, alkyl having from 1 to 6 carbon atoms and —(CH$_2$)$_z$—C$_6$H$_5$ wherein z is an integer from 1 to 4;
$R_5$ is selected from the group consisting of hydrogen, methyl and ethyl;
$R_6$ is selected from the group consisting of hydrogen, —(CH$_2$)$_y$—carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms and —(CH$_2$)$_x$—C$_6$H$_5$ wherein x is an integer from 1 to 4; and CO(CH$_2$)$_{x-1}$—C$_6$H$_5$;
Z is selected from the group consisting of
(a) alkylene having from one to nine carbon atoms;
(b) —(alk$_1$)$_m$—X—(alk$_2$)$_n$—wherein each of (alk$_1$) and (alk$_2$) is alkylene having from one to nine carbon atoms, with the proviso that the summation of carbon atoms in (alk$_1$) plus (alk$_2$) is not greater than nine; each of m and n is 0 or 1; X is selected from the group consisting of O, S, SO and SO$_2$; and W is selected from the group consisting of hydrogen, methyl, pyridyl, piperidyl,

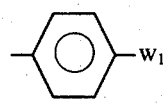

wherein W$_1$ is selected from the group consisting of hydrogen, fluoro and chloro; and

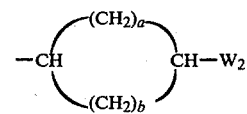

wherein W$_2$ is selected from the group consisting of hydrogen and

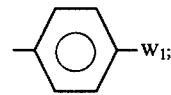

a is an integer from 1 to 5 and b is 0 or an integer from 1 to 5; with the proviso that the sum of a and b is not greater than 5; and
R' is selected from the group consisting of hydroxy, alkanoyloxy having 1 to 5 carbon atoms, hydroxymethyl, oxo, alkylene dioxy having from 2 to 4 carbon atoms and methylene.

8. A pharmaceutical composition in unit dosage form suitable for use as an analgesic, comprising a pharmaceutical carrier and, as active ingredient, from 0.01 to 50 mg. of a compound selected from the group consisting of those having the formula

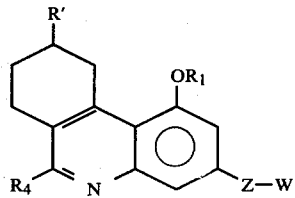

and the pharmaceutically-acceptable acid addition salts thereof, wherein
$R_1$ is selected from the group consisting of hydrogen, benzoyl, alkanoyl having from one to five carbon atoms and —CO—(CH$_2$)$_p$—NR$_2$R$_3$ wherein p is 0 or an integer from 1 to 4; each of $R_2$ and $R_3$ when taken individually is selected from the group consisting of hydrogen and alkyl having from one to four carbon atoms; $R_2$ and $R_3$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

$R_4$ is selected from the group consisting of hydrogen, alkyl having from 1 to 6 carbon atoms and $-(CH_2)_z-C_6H_5$ wherein z is an integer from 1 to 4;

$R_5$ is selected from the group consisting of hydrogen, methyl and ethyl;

$R_6$ is selected from the group consisting of hydrogen, $-(CH_2)_y-$carbalkoxy having from one to four carbon atoms in the alkoxy group and wherein y is 0 or an integer from 1 to 4, carbobenzyloxy, formyl, alkanoyl having from two to five carbon atoms, alkyl having from one to six carbon atoms and $-(CH_2)_x-C_6H_5$ wherein x is an integer from 1 to 4; and $CO(CH_2)_{x-1}C_6H_5$;

Z is selected from the group consisting of (a) alkylene having from one to nine carbon atoms;

(b) $-(alk_1)_m-X-(alk_2)_n-$ wherein each of $(alk_1)$ and $(alk_2)$ is alkylene having from one to nine carbon atoms, with the proviso that the summation of carbon atoms, in $(alk_1)$ plus $(alk_2)$ is not greater than nine; each of m and n is 0 or 1; X is selected from the group consisting of O, S, SO, and $SO_2$; and W is selected from the group consisting of hydrogen, methyl, pyridyl, piperidyl,

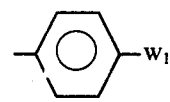

wherein $W_1$ is selected from the group consisting of hydrogen, fluoro and chloro; and

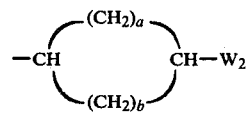

wherein $W_2$ is selected from the group consisting of hydrogen and

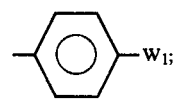

a is an integer from 1 to 5 and b is 0 or an integer from 1 to 5; with the proviso that the sum of a and b is not greater than 5; and R' is selected from the group consisting of hydroxy, alkanoyloxy having from 1 to 5 carbon atoms, hydroxymethyl, oxo, alkylene dioxy having from 2 to 4 carbon atoms and methylene.

* * * * *

UNITED STATES PATENT AND TRADEMARK OFFICE
CERTIFICATE OF CORRECTION

PATENT NO. : 4,380,542
DATED : April 19, 1983
INVENTOR(S) : MICHAEL R. JOHNSON

It is certified that error appears in the above-identified patent and that said Letters Patent is hereby corrected as shown below:

Col. 3, line 57, "$HR_2R_3$" should read -- $NR_2R_3$ --;

Col. 40, line 3, "[33-" should read -- [3- --;

Col. 64, line 26, "2.0" should read -- 2.08 --;

Col. 95, line 36, "Example ☐ " should read -- Example 58 --;

Col. 121, line 44, that portion of the formula reading "$-(Ch_2)_p-$" should read -- $-(CH_2)_p-$ --;

Col. 121, lines 59-66, delete definition of $R_6$;

Col. 123, lines 7-17, delete definition of $R_6$.

Signed and Sealed this

Twentieth Day of September 1983

[SEAL]

Attest:

Attesting Officer

GERALD J. MOSSINGHOFF
Commissioner of Patents and Trademarks